United States Patent
Jorand-Lebrun et al.

(10) Patent No.: US 10,314,841 B2
(45) Date of Patent: Jun. 11, 2019

(54) SUBSTITUTED PYRAZOLES AS IRAK INHIBITORS

(71) Applicant: Merck Patent GmbH, Darmstadt (DE)

(72) Inventors: Catherine Jorand-Lebrun, Arlington, MA (US); Reinaldo Jones, Lowell, MA (US)

(73) Assignee: Merck Patent GmbH, Darmstadt (DE)

( * ) Notice: Subject to any disclaimer, the term of this patent is extended or adjusted under 35 U.S.C. 154(b) by 202 days.

(21) Appl. No.: 15/101,446

(22) PCT Filed: Jan. 9, 2015

(86) PCT No.: PCT/US2015/010752
§ 371 (c)(1),
(2) Date: Jun. 3, 2016

(87) PCT Pub. No.: WO2015/106058
PCT Pub. Date: Jul. 16, 2015

(65) Prior Publication Data
US 2018/0169094 A1    Jun. 21, 2018

Related U.S. Application Data

(60) Provisional application No. 61/925,418, filed on Jan. 9, 2014.

(51) Int. Cl.
| | |
|---|---|
| *A61K 31/4155* | (2006.01) |
| *C07D 403/02* | (2006.01) |
| *A61K 31/506* | (2006.01) |
| *C07D 401/14* | (2006.01) |
| *C07D 405/14* | (2006.01) |
| *C07D 413/14* | (2006.01) |
| *C07D 403/14* | (2006.01) |
| *C07D 451/04* | (2006.01) |
| *A61P 37/00* | (2006.01) |
| *A61P 19/02* | (2006.01) |
| *A61P 29/00* | (2006.01) |

(52) U.S. Cl.
CPC ............ *A61K 31/506* (2013.01); *A61P 19/02* (2018.01); *A61P 29/00* (2018.01); *A61P 37/00* (2018.01); *C07D 401/14* (2013.01); *C07D 403/14* (2013.01); *C07D 405/14* (2013.01); *C07D 413/14* (2013.01); *C07D 451/04* (2013.01); *Y02A 50/414* (2018.01)

(58) Field of Classification Search
CPC ................... A61K 31/4155; C07D 403/02
USPC ............. 514/406; 544/333; 548/365.1
See application file for complete search history.

(56) References Cited

U.S. PATENT DOCUMENTS

2001/0044445 A1   11/2001   Bamaung et al.

FOREIGN PATENT DOCUMENTS

| | | |
|---|---|---|
| WO | 2010112210 A1 | 10/2010 |
| WO | 2014008992 A1 | 1/2014 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Hackam, et al. JAMA, 296(14), 2006, 1731-1732.*
Berge et al., Pharmaceutical Salts, J. Pharma Sciences, 1977, 66(1): 1-19.
Buckley et al., Bioorg Med Chem Lett., 2008, 18(12): 3656-3660.
Cao et al. Science, 1996, 271(5252): 1128-31.
Cohen P., Current Opinion in Cell Biology, 2009, 21: 317-324.
Foster A.B., Advances in Drug Research, 1985, 14: 1-39.
Gillette et al., Biochemistry, 1994, 33: 2927-2937.
Hanzlik et al., J. Org. Chem., 1990, 55: 3992-3997.
Higuchi and Stella, vol. 14 of the A.C.S. Symposium Series, American Chemical Society (1975).
Hughes D.L., Organic Reactions (New York), 1992, 42: 335-656.
Jarman et al., Carcinogenesis, 1995, 16(4): 683-688.
Li et al., Proc. Natl. Acad. Sci. USA, 2002, 99(8): 5567-5572.
Miyaura and Suzuki, Chem. Rev., 1995, 95: 2457-2483.
Muzio et al., Science, 1997, 278(5343): 1612-1615.

(Continued)

*Primary Examiner* — Douglas M Willis
(74) *Attorney, Agent, or Firm* — Millen White Zelano and Branigan, PC; John Sopp

(57) ABSTRACT

The present invention provides compounds of Formula (II) for the treatment of cancer, rheumatoid arthritis and other diseases.

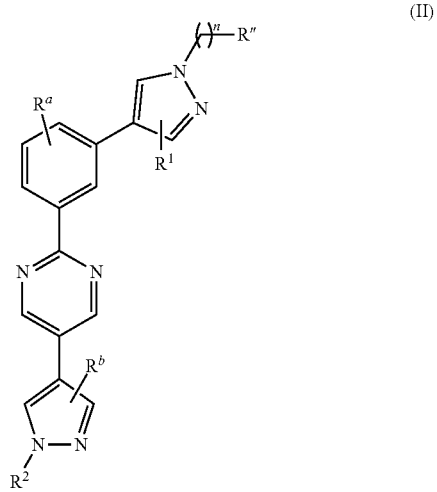

11 Claims, No Drawings

(56) References Cited

OTHER PUBLICATIONS

The Periodic Table of the Elements, CAS version, Handbook of Chemistry and Physics, 75th Ed.
Organic Chemistry, Thomas Sorrell, University Science Books, Sausalito,1999.
March's Advanced Organic Chemistry, 5th Ed., Ed.: Smith, M.B. and March, J., John Wiley & Sons, New York: 2001.
Reider et al., J. Org. Chem., 1987, 52(15): 3326-3334.
Reynolds and Kassiou, Current Organic Chemistry, 2009, 13(16): 1610-1632.
Ringwood and Li, Cytokine, 2008, 42(1): 1-7.
E.B. Roche, Pergamon Press: New York (1987), pp. 14-21.
Takahiro and Toshiaki, Tetrahedron Lett., 2005, 46: 3573-3577.
Tyle P., Pharmaceutical Research, 1986 3(6): 318-326.
Wesche et al., J. Biol. Chem., 1999, 274(27): 19403-19410.
Theodora W. Greene and Peter G. M. Wuts in "Protective Groups in Organic Synthesis", Wiley Interscience, 3rd Edition 1999.
Philip J. Kocienski, in "Protecting Groups", Georg Thieme Verlag Stuttgart, New York, 1994.

\* cited by examiner

SUBSTITUTED PYRAZOLES AS IRAK INHIBITORS

FIELD

The present invention provides for pyrimidine pyrazolyl derivatives of Formula (I) or Formula (II) as IRAK inhibitors and their use in the treatment of cancer, and other diseases related to IRAK overexpression, including rheumatoid arthritis, systemic lupus erythematosus or lupus nephritis.

BACKGROUND

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides compounds of Formula (I) and Formula (II). In another aspect, the invention provides compounds of Formula (I) and Formula (II) which are suitable for the treatment and/or prevention of disorders related to IRAK. In another aspect, the invention provides compounds which are able to modulate, especially inhibit the activity or function of IRAK in disease states in mammals, especially in humans.

According to another aspect of the invention are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) or Formula (II) which are selective for IRAK-4 and/or IRAK-1.

According to another aspect the invention provides a kit or a set comprising at least one compound of Formula (I) or Formula (II), preferably in combination with immunomodulating agents. Preferably, the kit consists of separate packs of:

(a) an effective amount of a compound of the formula (I) or formula (II) and/or pharmaceutically usable derivatives, solvates, salts, hydrates and stereoisomers thereof, including mixtures thereof in all ratios, and
(b) an effective amount of a further medicament active ingredient.

According to another aspect the invention provides a process for the synthesis of compounds of Formulae (I) and related Formulae.

DETAILED DESCRIPTION OF THE INVENTION

In certain aspects, the invention provides a compound of Formula (I)

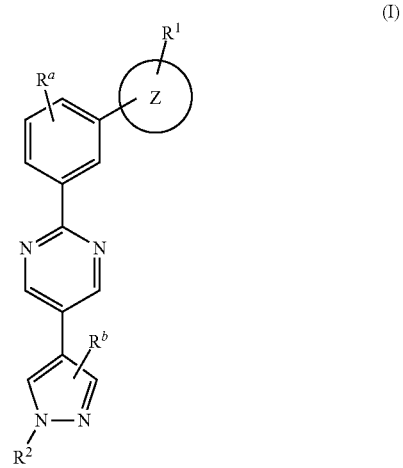

wherein
Ring Z is;

wherein
X is O, S or N; Y is C or N; and T is C or N; or
Ring Z is a pyridine or a pyridazine group;
$R^1$ is absent or $R^1$ is A or Q-R;
$R^a$ is absent or $R^a$ is $OR^3$, $CF_3$, Hal, $NO_2$;
$R^b$ is absent or $R^b$ is A or COR;
$R^2$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, each of which is optionally substituted;
each Q is a linear or branched alkylene, having 1 to 6 carbon atoms wherein 1-5 H atoms may be replaced by a grouped independently selected from $OR^3$, Hal, $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S,
each A is a linear or branched alkyl having 1 to 10 carbon atoms wherein 1 to 7 H atoms may be replaced by a group independently selected from —$OR^3$, Hal, $NHSO_2A$, $SO_2A$, SOA, $N(R^3)_2$, and wherein 1, 2 or 3 non-adjacent —$CH_2$— groups may be replaced by a group independently selected from —CO—, $NR^3$ and/or —O—,
each Hal is F, Cl, Br or I,
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
and
each $R^3$ is H or $C_1$-$C_6$-alkyl wherein 1 H atom may be replaced by a group selected from OH, O—$C_1$-$C_6$-alkyl, and Hal.
and pharmaceutically acceptable derivatives, solvates, tautomers, salts, hydrates and stereoisomers thereof, including mixtures thereof in all ratios.
In certain embodiments, Ring Z is

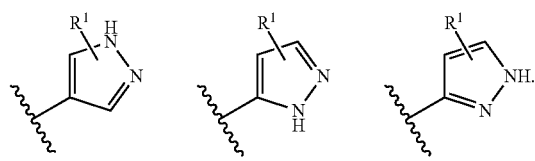

In one aspect, the present invention provides a compound of Formula (II)

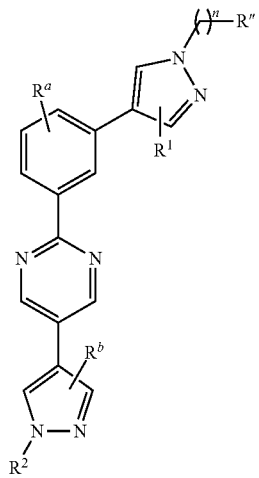

wherein
R" is H, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, each of which is optionally substituted;
$R^1$ is absent or $R^1$ is A or Q-R;
$R^a$ is absent or $R^a$ is $OR^3$, $CF_3$, Hal, $NO_2$;
$R^b$ is absent or $R^b$ is A or COR;
$R^2$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur, each of which is optionally substituted;
each Q is independently a linear or branched alkylene, having 1 to 6 carbon atoms wherein 1-5 H atoms may be replaced by a groupe independently selected from $OR^3$, Hal, $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S,
each A is independently a linear or branched alkyl having 1 to 10 carbon atoms wherein 1 to 7 H atoms may be replaced by a group independently selected from —$OR^3$, Hal, $NHSO_2A$, $SO_2A$, SOA, $N(R^3)_2$, and wherein 1, 2 or 3 non-adjacent —$CH_2$— groups may be replaced by a group independently selected from —CO—, $NR^3$ and/or —O—,
each Hal is independently F, Cl, Br or I,
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
each $R^3$ is H or $C_1$-$C_6$-alkyl wherein 1 H atom may be replaced by a group selected from OH, O—$C_1$-$C_6$-alkyl, and Hal; and n is 0 or 1;
and pharmaceutically acceptable derivatives, solvates, tautomers, salts, hydrates and stereoisomers thereof, including mixtures thereof in all ratios.

In certain embodiments, R" is H.

In certain embodiments, R" is optionally substituted $C_{1-6}$ aliphatic. In certain embodiments, R" is optionally substituted $C_{3-10}$ aryl. In certain embodiments, R" is an optionally substituted 3-8 membered saturated or partially unsaturated carbocyclic ring. In certain embodiments, R" is an optionally substituted 3-7 membered heterocylic ring having 1-4 heteroatoms independently selected from nitrogen, oxygen, or sulfur. In certain embodiments, R" is an optionally substituted 5-6 membered monocyclic heteroaryl ring having 1-4 heteroatoms independently selected from nitrogen, oxygen, or sulfur.

In certain embodiments, R" is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, R" is phenyl, cyclopropyl, cyclobutyl, cyclopentyl, cyclohexyl, cycloheptyl, furanyl, furazanyl, imidazolidinyl, imidazolinyl, imidazolyl, 1H-indazolyl, indolenyl, isoxazolyl, morpholinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl, each of which is optionally substituted.

In certain embodiments, R" is methyl, ethyl, propyl, i-propyl, butyl, s-butyl, t-butyl, straight or branched pentyl, or straight or branched hexyl; each of which is optionally substituted.

In certain embodiments, R" is

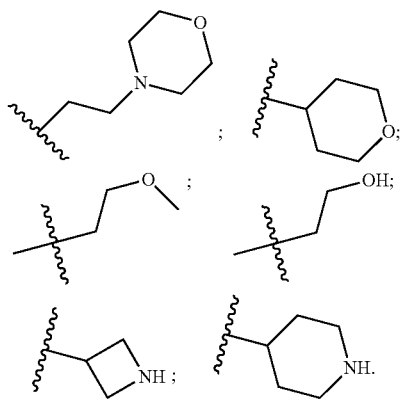

In certain embodiments of formula I or formula II, $R^1$ is absent.

In certain embodiments of formula I or formula II, $R^a$ is absent.

In certain embodiments of formula I or formula II, $R^b$ is absent.

In certain embodiments of formula I or formula II, $R^2$ is optionally substituted $C_{1-6}$ aliphatic. In certain embodiments, $R^2$ is optionally substituted $C_{3-10}$ aryl. In certain embodiments of formula I or formula II, $R^2$ is an optionally substituted 3-8 membered saturated or partially unsaturated carbocyclic ring. In certain embodiments of formula I or formula II, $R^2$ is an optionally substituted 3-7 membered heterocylic ring having 1-4 heteroatoms independently selected from nitrogen, oxygen, or sulfur. In certain embodiments of formula I or formula II, $R^2$ is an optionally substituted 5-6 membered monocyclic heteroaryl ring having 1-4 heteroatoms independently selected from nitrogen, oxygen, or sulfur.

In certain embodiments of formula I or formula II, $R^2$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments of formula I or formula II, $R^2$ is phenyl, cyclopropyl, cyclobutyl, cyclopentyl, cyclohexyl, cycloheptyl, furanyl, furazanyl, imidazolidinyl, imidazolinyl, imidazolyl, 1H-indazolyl, indolenyl, isoxazolyl, morpholinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl, each of which is optionally substituted.

In certain embodiments of formula I or formula II, $R^2$ is methyl, ethyl, propyl, i-propyl, butyl, s-butyl, t-butyl, straight or branched pentyl, or straight or branched hexyl; each of which is optionally substituted.

In certain embodiments of formula I or formula II, $R^2$ is optionally substituted with A, OA, COA, CN, Hal, $NO_2$, $OR^3$, SOA, $SO_2A$, $CO(NR^3)_2$, COHet, $OR^3$, $Het^1$, $CH_2Het^1$, $NH_2$, NHCOA, NHSO2A, $OCH_2Cyc^1$, $SO_2A$ and/or —SA (=NH)(=O).

In certain embodiments, each Q is independently a linear or branched alkylene, having 1 to 6 carbon atoms wherein 1-5 H atoms may be replaced by a group independently selected from $OR^3$, Hal, $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from N, O and S, each A is independently a linear or branched alkyl or alkene, having 1 to 10 carbon atoms wherein 1 to 7 H atoms may be replaced by a group independently selected from —$OR^3$, Hal, $NHSO_2A$, $SO_2A$, SOA, $N(R^3)_2$, CN and wherein 1, 2 or 3 non-adjacent —$CH_2$— groups may be replaced by a group independently selected from —CO—, $NR^3$ and/or —O—, each Hal is independently F, Cl, Br or I, each $R^3$ is independently H or $C_1$-$C_6$-alkyl wherein 1 H atom may be replaced by a group selected from OH, O—$C_1$-$C_6$-alkyl, Hal, and Het1.

each $Het^1$ is independently a five- or six membered saturated monocyclic heterocycle, which contains 1-3N- and/or O-atoms, which optionally is monosubstituted by A, each $Cyc^1$ is independently cycloalkyl with 3-7 atoms.

In certain embodiments of formula I or formula II, $R^2$ is

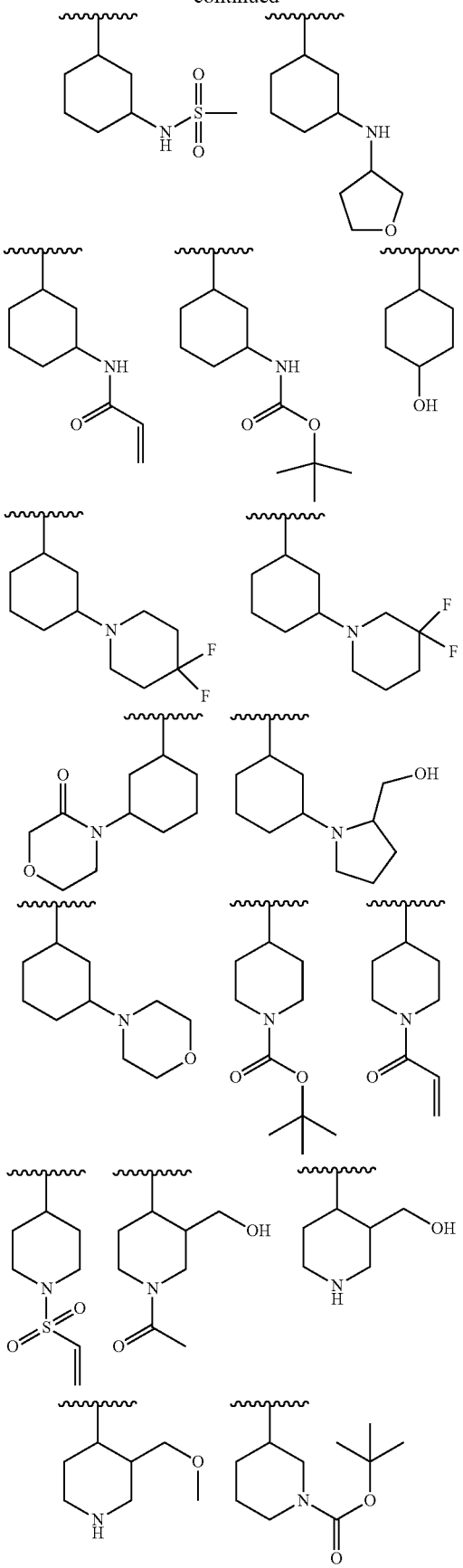

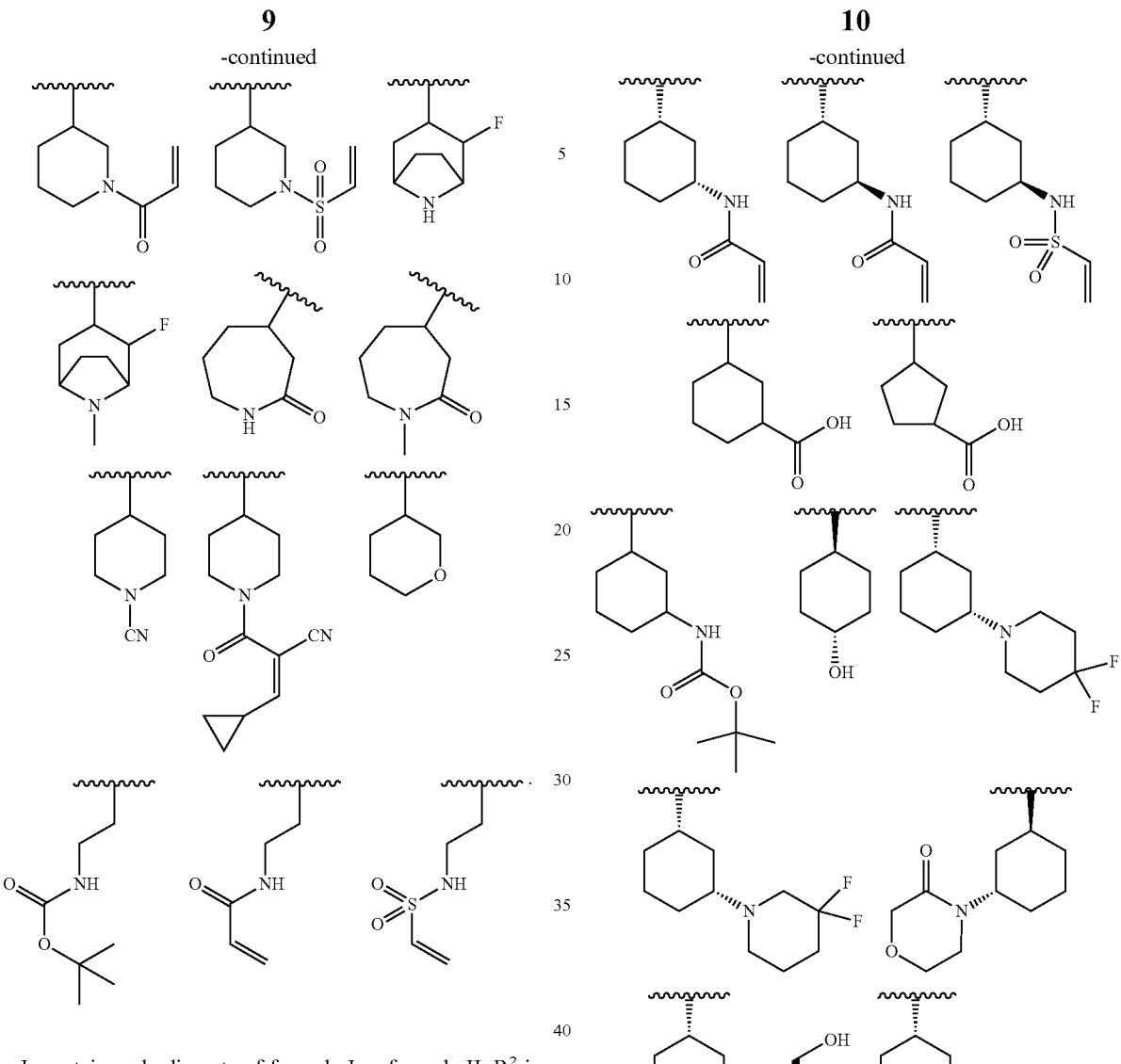
In certain embodiments of formula I or formula II, R² is
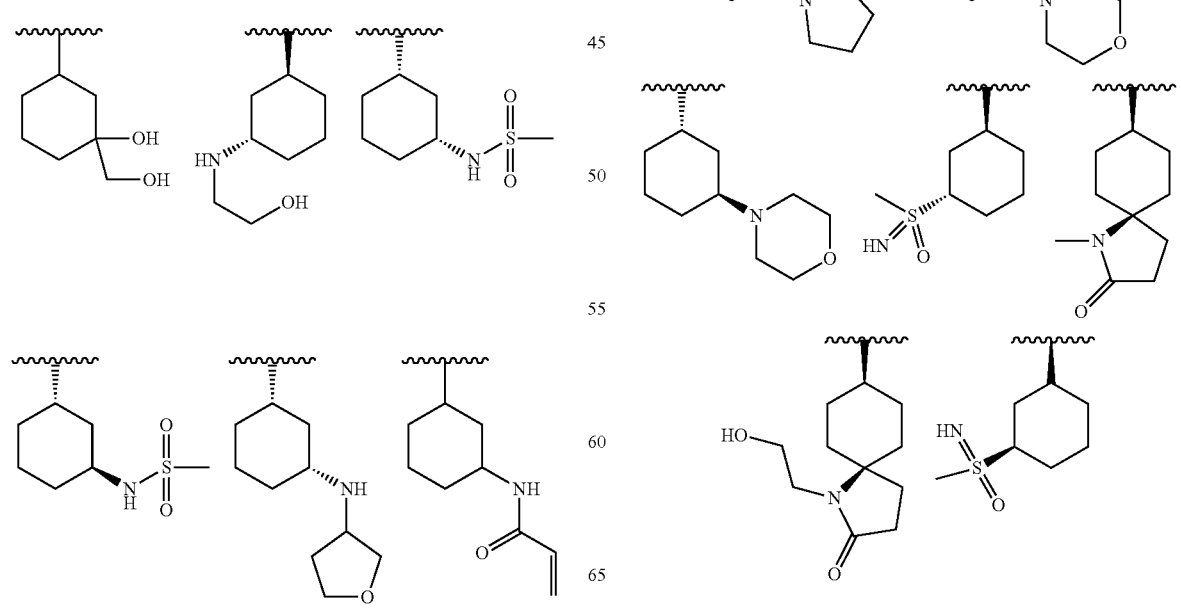

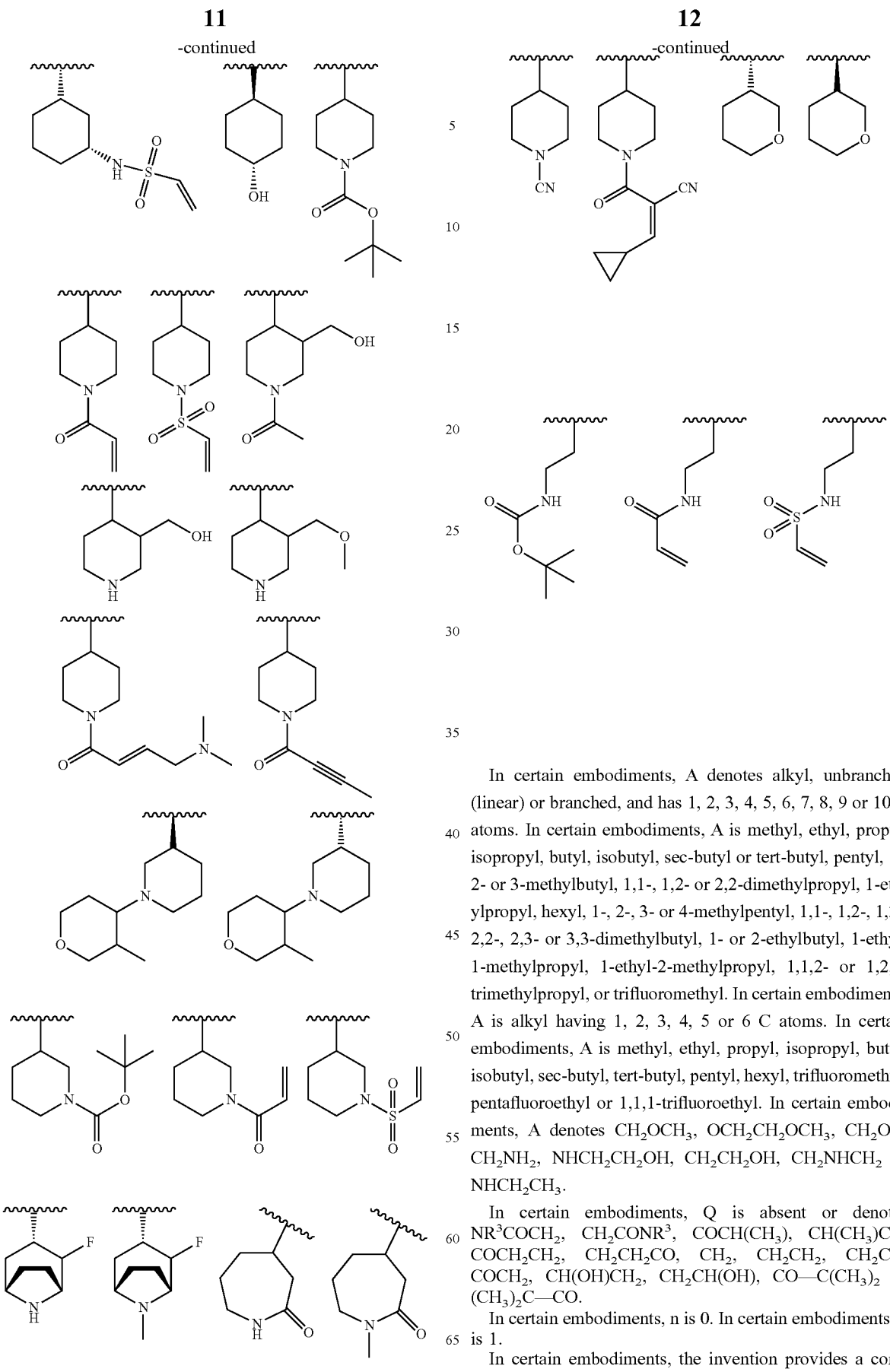

In certain embodiments, A denotes alkyl, unbranched (linear) or branched, and has 1, 2, 3, 4, 5, 6, 7, 8, 9 or 10 C atoms. In certain embodiments, A is methyl, ethyl, propyl, isopropyl, butyl, isobutyl, sec-butyl or tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, or trifluoromethyl. In certain embodiments, A is alkyl having 1, 2, 3, 4, 5 or 6 C atoms. In certain embodiments, A is methyl, ethyl, propyl, isopropyl, butyl, isobutyl, sec-butyl, tert-butyl, pentyl, hexyl, trifluoromethyl, pentafluoroethyl or 1,1,1-trifluoroethyl. In certain embodiments, A denotes $CH_2OCH_3$, $OCH_2CH_2OCH_3$, $CH_2OH$, $CH_2NH_2$, $NHCH_2CH_2OH$, $CH_2CH_2OH$, $CH_2NHCH_2$ or $NHCH_2CH_3$.

In certain embodiments, Q is absent or denotes $NR^3COCH_2$, $CH_2CONR^3$, $COCH(CH_3)$, $CH(CH_3)CO$, $COCH_2CH_2$, $CH_2CH_2CO$, $CH_2$, $CH_2CH_2$, $CH_2CO$, $COCH_2$, $CH(OH)CH_2$, $CH_2CH(OH)$, $CO-C(CH_3)_2$ or $(CH_3)_2C-CO$.

In certain embodiments, n is 0. In certain embodiments, n is 1.

In certain embodiments, the invention provides a compound below in Table 1:

TABLE 1
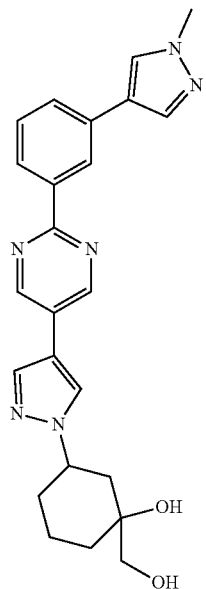 [SMILES: Cn1cc(-c2cccc(-c3ncc(-c4cnn(C5CCCC(O)(CO)C5)c4)cn3)c2)cn1]
1
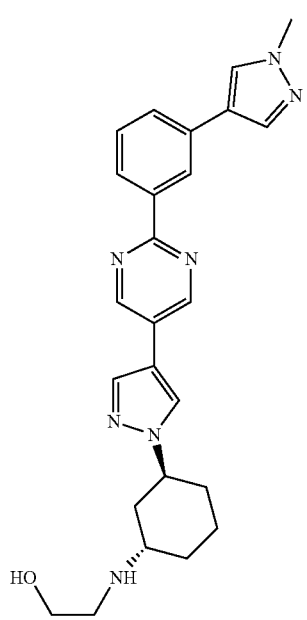 [SMILES: Cn1cc(-c2cccc(-c3ncc(-c4cnn([C@H]5CCC[C@H](NCCO)C5)c4)cn3)c2)cn1]
2
TABLE 1-continued
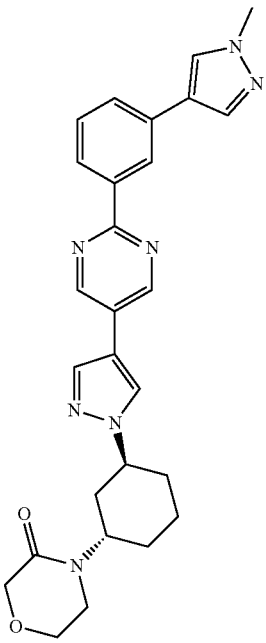 [SMILES: Cn1cc(-c2cccc(-c3ncc(-c4cnn([C@H]5CCC[C@H](N6CCOCC6=O)C5)c4)cn3)c2)cn1]
3
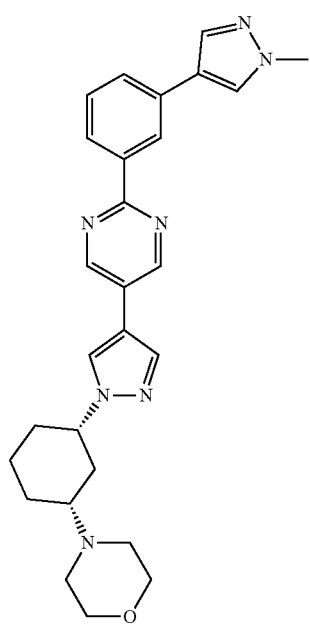 [SMILES: Cn1cc(-c2cccc(-c3ncc(-c4cnn([C@H]5CCC[C@@H](N6CCOCC6)C5)c4)cn3)c2)cn1]
4

TABLE 1-continued
5
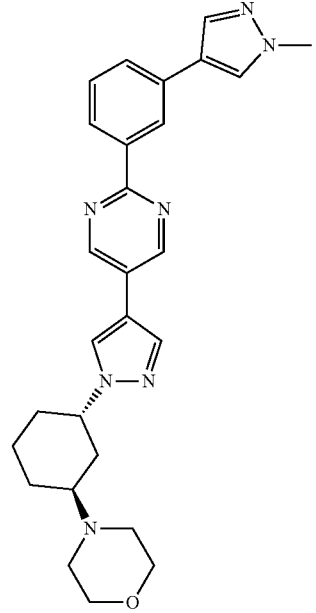 [SMILES: Cn1cc(-c2cccc(-c3ncc(-c4cnn([C@H]5CCC[C@H](N6CCOCC6)C5)c4)cn3)c2)cn1]
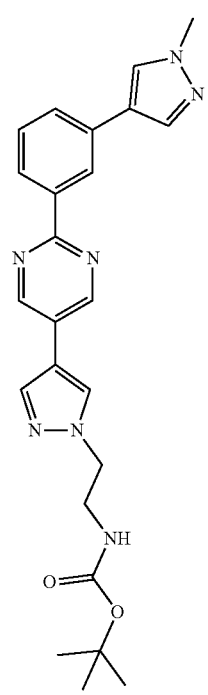 [SMILES: Cn1cc(-c2cccc(-c3ncc(-c4cnn(CCNC(=O)OC(C)(C)C)c4)cn3)c2)cn1]
TABLE 1-continued
7
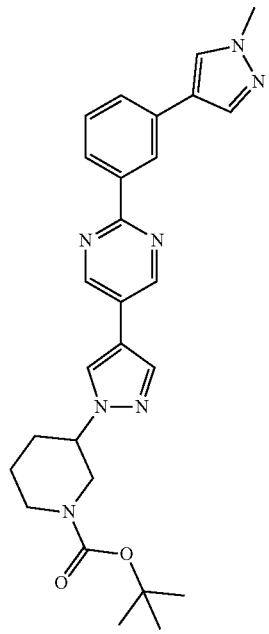 [SMILES: Cn1cc(-c2cccc(-c3ncc(-c4cnn(C5CCCN(C(=O)OC(C)(C)C)C5)c4)cn3)c2)cn1]
8
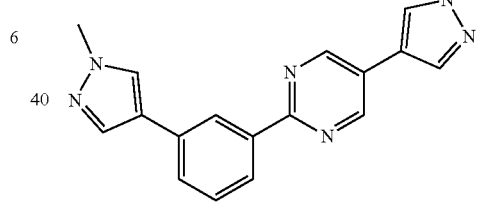
9
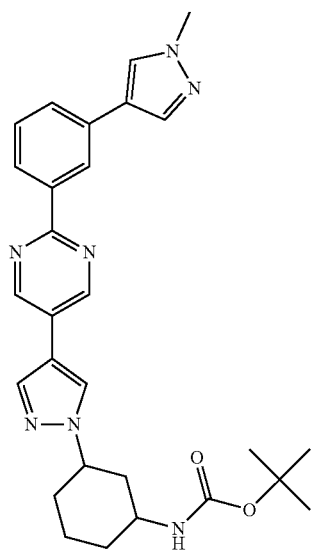 [SMILES: Cn1cc(-c2cccc(-c3ncc(-c4cnn(C5CCCC(NC(=O)OC(C)(C)C)C5)c4)cn3)c2)cn1]

TABLE 1-continued
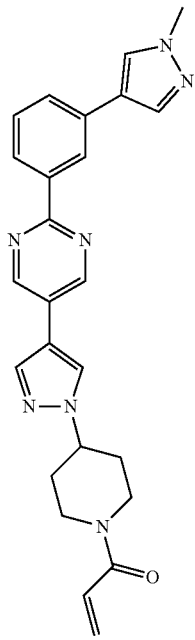 [SMILES: C=CC(=O)N1CCC(n2cc(-c3cnc(-c4cccc(-c5cnn(C)c5)c4)nc3)cn2)CC1]
10
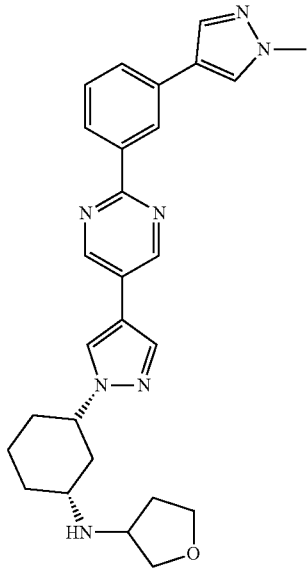
12
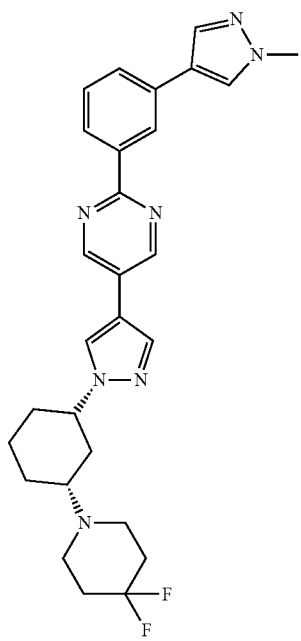
11
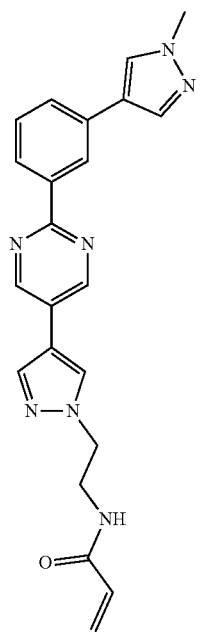 [SMILES: C=CC(=O)NCCn1cc(-c2cnc(-c3cccc(-c4cnn(C)c4)c3)nc2)cn1]
13

TABLE 1-continued
14
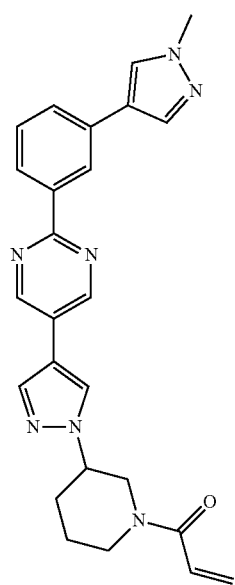 [SMILES: C=CC(=O)N1CCCC(n2cc(-c3cnc(-c4cccc(-c5cnn(C)c5)c4)nc3)cn2)C1]
16
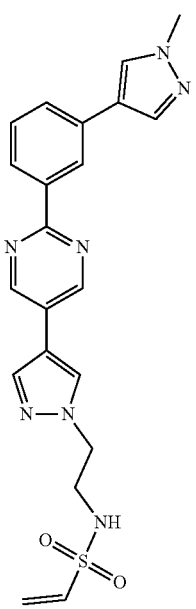
15
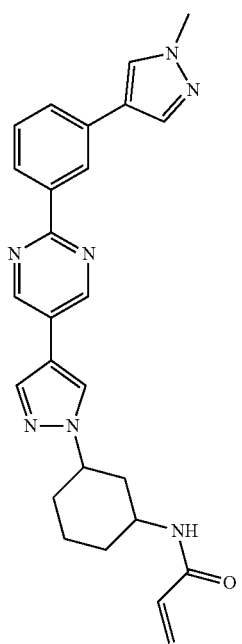 [SMILES: C=CC(=O)NC1CCCC(n2cc(-c3cnc(-c4cccc(-c5cnn(C)c5)c4)nc3)cn2)C1]
17
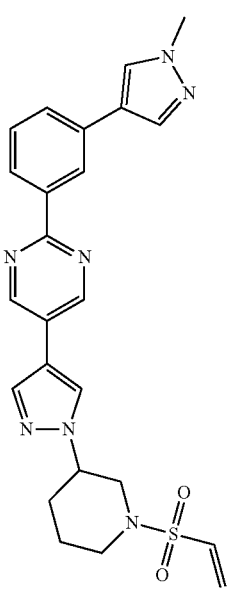 [SMILES: C=CS(=O)(=O)N1CCCC(n2cc(-c3cnc(-c4cccc(-c5cnn(C)c5)c4)nc3)cn2)C1]

TABLE 1-continued
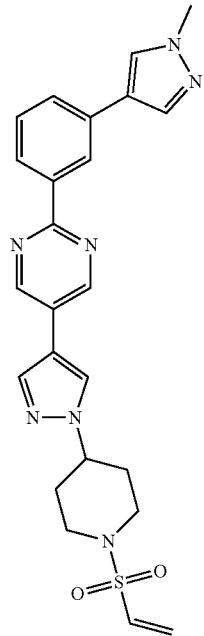 [SMILES: C=CS(=O)(=O)N1CCC(n2cc(-c3cnc(-c4cccc(-c5cnn(C)c5)c4)nc3)cn2)CC1]
18
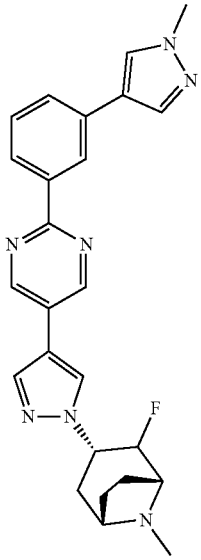
20
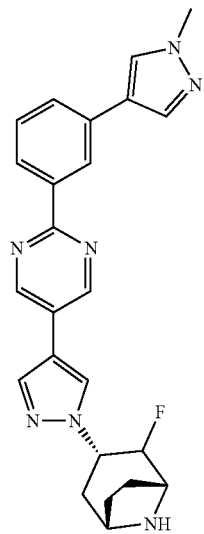 [SMILES: Cn1cc(-c2cccc(-c3ncc(-c4cnn([C@H]5C[C@@H]6CC[C@@H](N6)C5F)c4)cn3)c2)cn1]
19
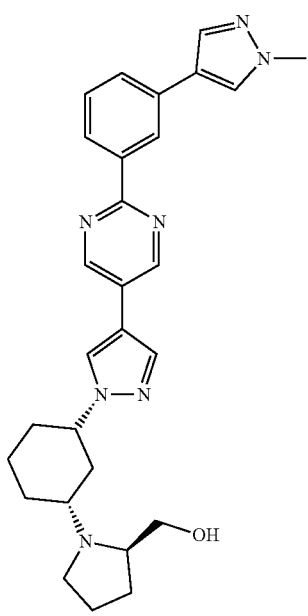
21

TABLE 1-continued
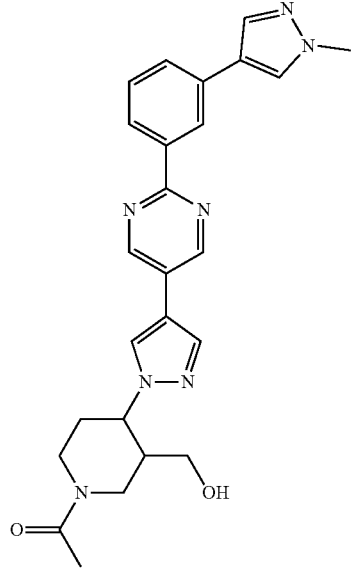 [SMILES: CC(=O)N1CCC(n2cc(-c3cnc(-c4cccc(-c5cnn(C)c5)c4)nc3)cn2)C(CO)C1]
22
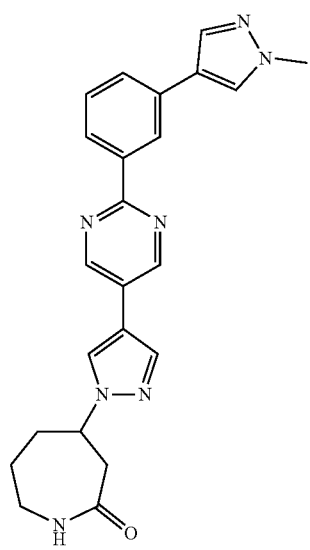 [SMILES: Cn1cc(-c2cccc(-c3ncc(-c4cnn(C5CCCNC(=O)C5)c4)cn3)c2)cn1]
23
TABLE 1-continued
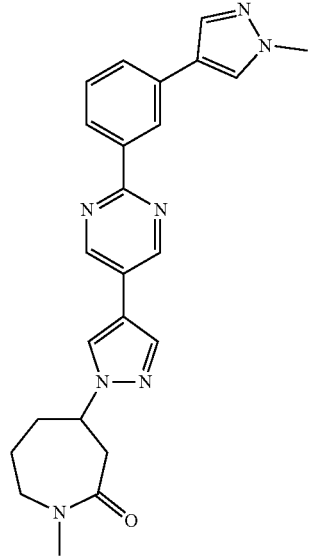 [SMILES: CN1CCCC(n2cc(-c3cnc(-c4cccc(-c5cnn(C)c5)c4)nc3)cn2)CC1=O]
24
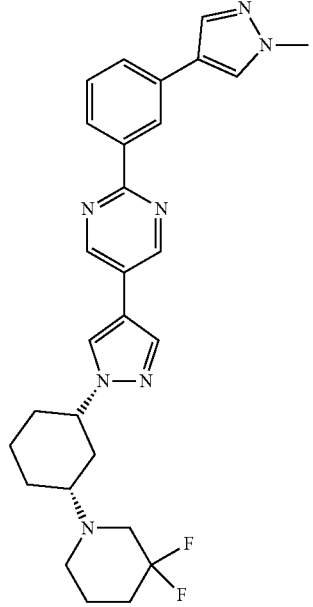
25

TABLE 1-continued
26
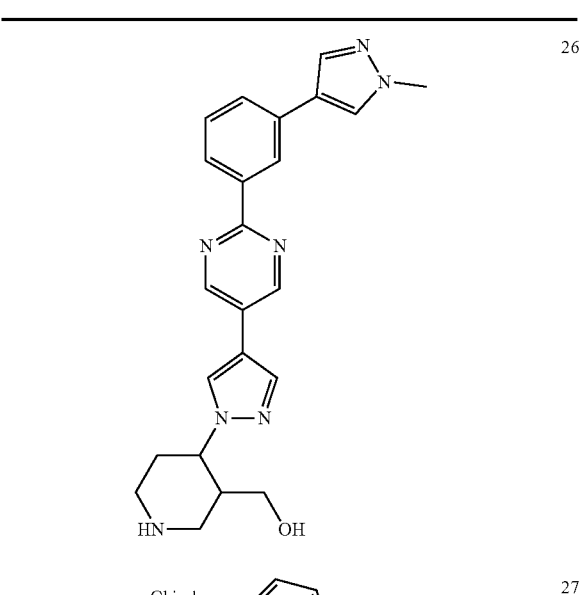
27
Chiral
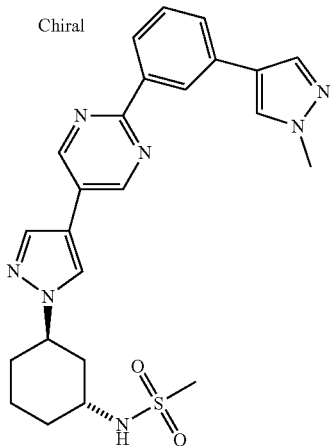 [SMILES: Cn1cc(-c2cccc(-c3ncc(-c4cnn([C@@H]5CCC[C@@H](NS(C)(=O)=O)C5)c4)cn3)c2)cn1]
28
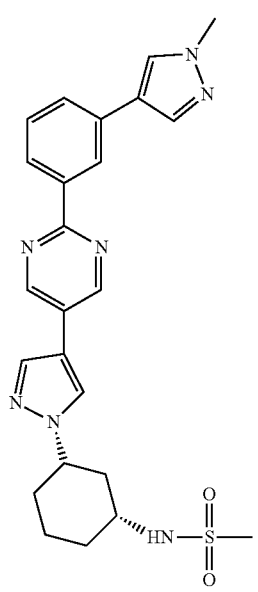
TABLE 1-continued
29
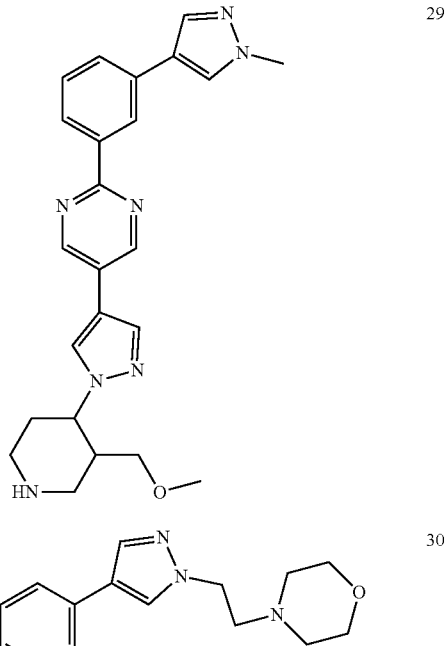
30
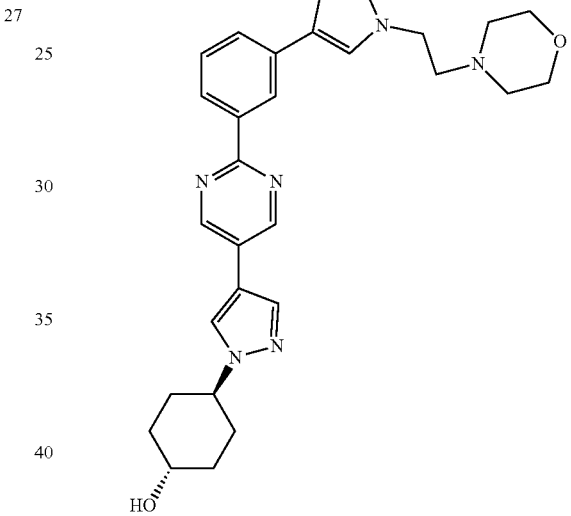
31
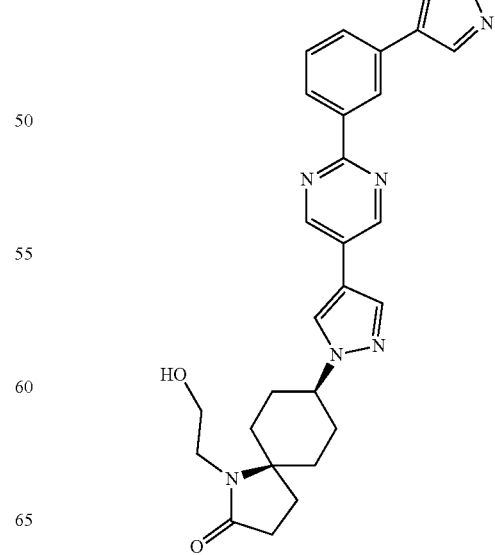

TABLE 1-continued
32 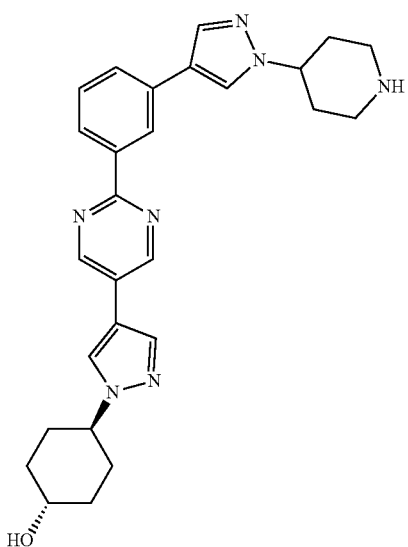 [SMILES: O[C@H]1CC[C@H](n2cc(-c3cnc(-c4cccc(-c5cnn(C6CCNCC6)c5)c4)nc3)cn2)CC1]
33 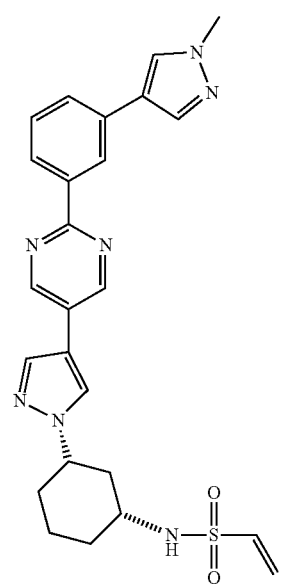
34 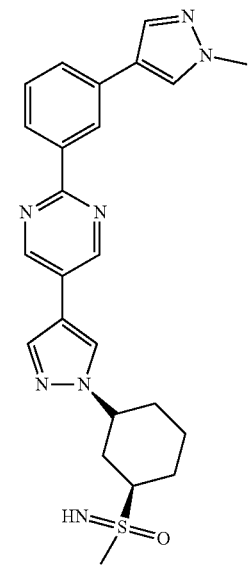
35 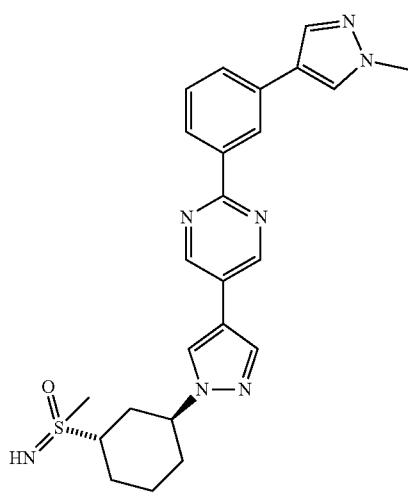 [SMILES: Cn1cc(-c2cccc(-c3ncc(-c4cnn([C@H]5CCC[C@H](S(C)(=N)=O)C5)c4)cn3)c2)cn1]
36 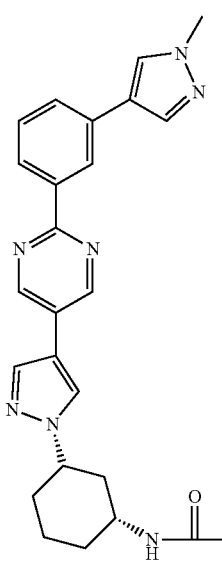

TABLE 1-continued
37
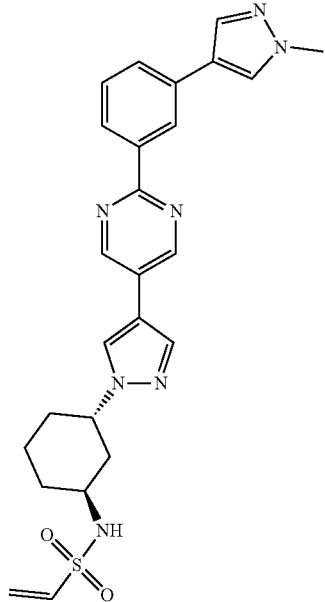 [SMILES: C=CS(=O)(=O)N[C@H]1CCC[C@H](n2cc(-c3cnc(-c4cccc(-c5cnn(C)c5)c4)nc3)cn2)C1]
38
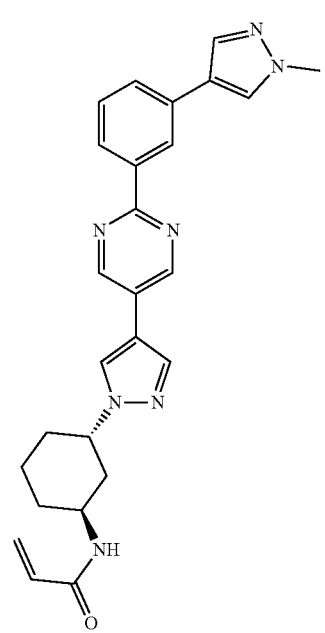 [SMILES: C=CC(=O)N[C@H]1CCC[C@H](n2cc(-c3cnc(-c4cccc(-c5cnn(C)c5)c4)nc3)cn2)C1]
TABLE 1-continued
39 Chiral
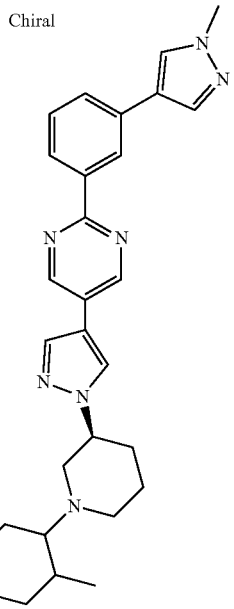
40 Chiral
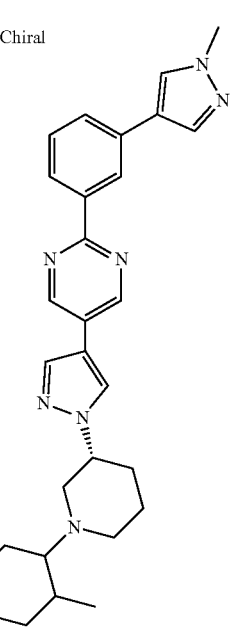

TABLE 1-continued
41
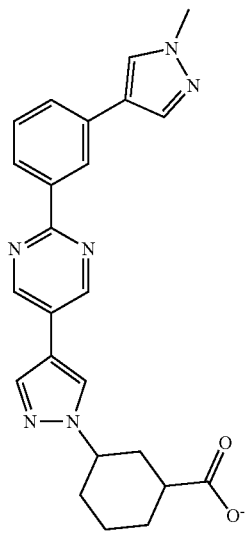 [SMILES: Cn1cc(-c2cccc(-c3ncc(-c4cnn(C5CCCC(C(=O)[O-])C5)c4)cn3)c2)cn1]
43
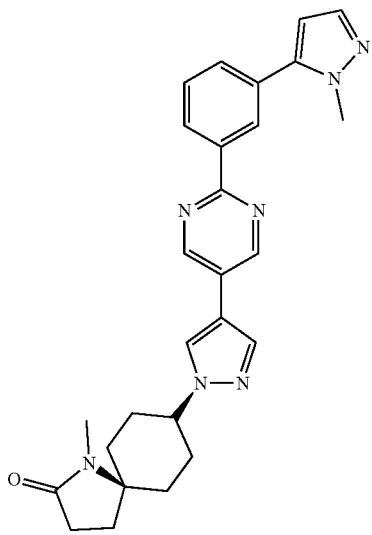
42
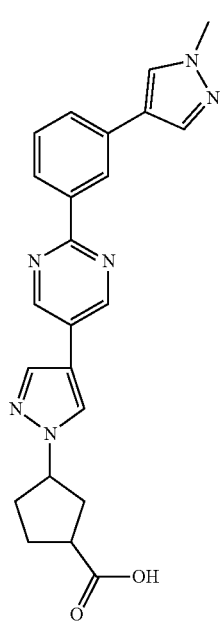 [SMILES: Cn1cc(-c2cccc(-c3ncc(-c4cnn(C5CCC(C(=O)O)C5)c4)cn3)c2)cn1]
44
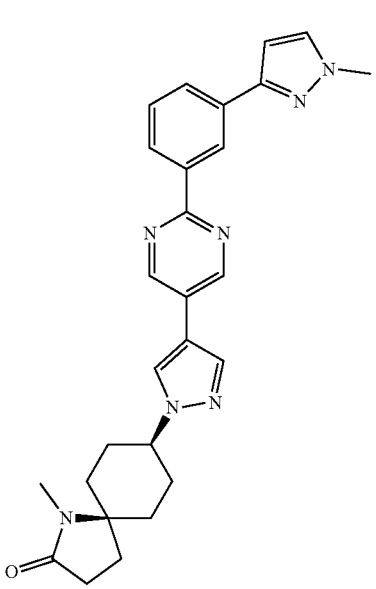 [SMILES: Cn1ccc(-c2cccc(-c3ncc(-c4cnn([C@H]5CC[C@]6(CCC(=O)N6C)CC5)c4)cn3)c2)n1]

TABLE 1-continued

45

46

47

48

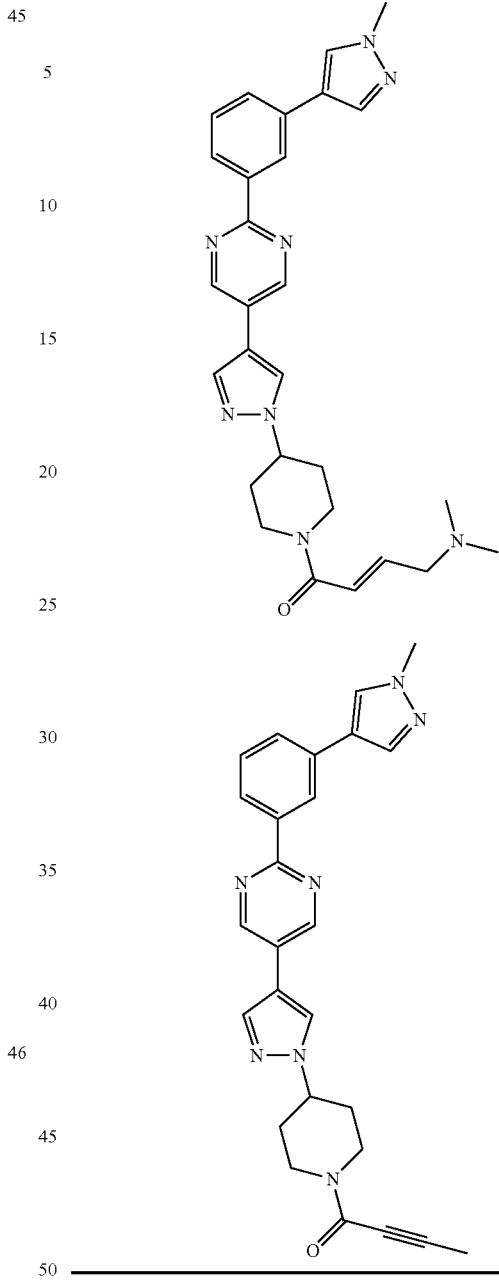

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl. "$C_1$-$C_6$-alkyl" or "$C_1$-$C_6$-alkyl group" denotes a linear or branched alkyl chain having 1 to 6 carbon atoms. "$C_1$-$C_6$-alkyl" or "$C_1$-$C_3$-alkyl" may also include halo-alkyl. Halo-alkyl contains 1 to 10 halogen atoms, preferably 1 to 3 halogen atoms. Halo-alkyl contains for example a group —$CF_3$, —$CHF_2$ or —$CH_2F$.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —($CH_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

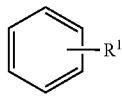

refers to at least

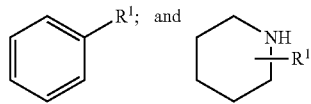

refers to at least

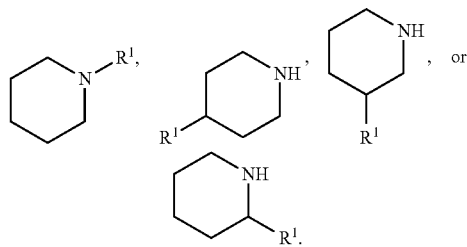

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°—(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S) R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°, —SC(S)SR°, —(CH$_2$)$_{0-4}$OC(O)NR°$_2$; —C(O)N(OR)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted"

group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,
—OH, protected hydroxy, alkoxy, oxo, thiooxo,
—NO$_2$, —CN, CF$_3$, N$_3$,
—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino,
—O— alkyl, —O— alkenyl, —O— alkynyl, —O— cycloalkyl, —O-aryl, —O-heteroaryl, —O— heterocyclic,
—C(O)— alkyl, —C(O)— alkenyl, —C(O)— alkynyl, —C(O)— carbocyclyl, —C(O)-aryl, —C(O)-heteroaryl, —C(O)-heterocyclyl,
—CONH$_2$, —CONH— alkyl, —CONH— alkenyl, —CONH— alkynyl, —CONH-carbocyclyl, —CONH-aryl, —CONH-heteroaryl, —CONH-heterocyclyl,
—OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl,
—NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH— heteroaryl, —NHC(O)NH-heterocyclyl, NHC(S)NH$_2$, —NHC(S)NH— alkyl, —NHC(S)NH-alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH-alkenyl, —NHC(NH)NH— alkenyl, —NHC(NH)NH— carbocyclyl, —NHC(NH)NH-aryl, —NHC(NH)NH-heteroaryl, —NHC(NH)NH-heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl,
—C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl,
—S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl,
—NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

A "leaving group" denotes a chemical moiety which can be removed or replaced by another chemical group.

Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

Synthesis

The following abbreviations refer to the abbreviations used below:

Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), DIEA (di-isopropyl ethylamine), DMA (dimethyl acetamide), DMSO (Dimethyl Sulfoxide), DMF (N,N-Dimethylformamide), Dppf (1,1'-bis (diphenyl phosphino ferrocene)), EtOAc (Ethyl acetate), EtOH (Ethanol), g (gram), cHex (Cyclohexane), HATU (N-[(Dimethylamino) (3H-[1,2,3]triazolo[4,5-b]pyridin-3-yloxy)methylene]-N-methylmethanaminiumhexafluoro phosphate), HPLC (High Performance Liquid Chromatography), hr (hour), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), mp (melting point), MS (Mass Spectrometry), MW (microwave), NMR (Nuclear Magnetic Resonance), O/N (overnight), PBS (Phosphate Buffered Saline), $PPh_3$ (triphenylphosphine), RT (room temperature), TEA (Triethyl amine), TFA (Trifluoroacetic acid), THF (Tetrahydrofuran), TLC (Thin Layer Chromatography), oTol (ortho-tolyl), UV (Ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999.

Depending on the nature of $R^1$, $R^2$, $R^a$, and $R^b$ different synthetic strategies may be selected for the synthesis of compounds of Formula (I). In the process illustrated in the following schemes, $R^1$, $R^2$, $R^a$, and $R^b$ are as above defined in the description unless otherwise mentioned.

Compounds of formula (I) wherein $R^1$, $R^2$, $R^a$, $R^b$ and Z are as above defined can be prepared by Suzuki-Miyura coupling reaction between a compound of Formula (II), wherein $R^1$, $R^a$ and Z are as above defined and X is an halogen (preferably bromine or iodine) or a triflate group, and a boronic acid or ester of Formula (III) wherein $R^2$ and $R^b$ are as above defined and R is H or an alkyl group as outlined in Scheme 1. General protocols for such coupling are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an aryl halide of Formula (II) and a boronic acid or ester of Formula (III) are heated in a suitable solvent, such as THF, toluene, DMF or dioxane, in the presence or absence of water as a co-solvent, in the presence of a base, such as $Cs_2CO_3$, $K_2CO_3$, CsF, and with an appropriate catalyst such as but not limited to dichlorobis(triphenylphosphine)palladium(II), $Pd(PPh_3)_4$ or 1,1'-bis(diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation.

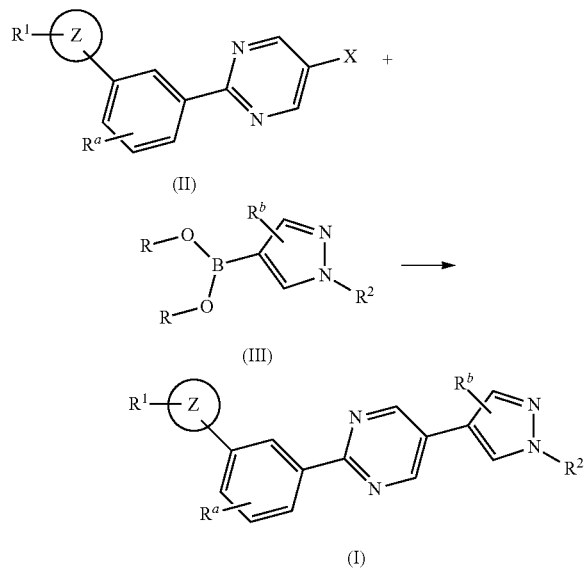

Scheme 1

Generally, compounds of Formula (IIa), wherein R$^1$, R$^a$ and Z are as above defined and X is bromine, can be obtained as outlined in Scheme 2. Compounds of Formula (IV), wherein R$^1$ and Z are as above defined and R is H or an alkyl group can be coupled with a compound of Formula (V), wherein R$^a$ is as above defined, by a Suzuki-Miyura coupling reaction to give a compound of general formula (VI) wherein R$^1$, R$^a$ and Z are as above defined. General protocols for such coupling are given below in the Examples: in a typical procedure, the aryl halide of Formula (V) and the boronic acid or ester of Formula (IV) are heated in a suitable solvent, such as THF, toluene, DMF or dioxane, in the presence or absence of water as a co-solvent, in the presence of a base, such as Cs$_2$CO$_3$, K$_2$CO$_3$, CsF, and with an appropriate catalyst such as but not limited to dichlorobis(triphenylphosphine)palladium(II), Pd(PPh$_3$)$_4$ or 1,1'-bis(diphenylphosphino)ferrocenedichloro palladium(II), Pd(OAc)$_2$, Pd$_2$(dba)$_3$, Pd(Cl)$_2$(PPh$_3$)$_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation. Compounds of Formula (VI), wherein R$^1$, R$^a$ and Z are as above defined, can be converted in compounds of Formula (VII), wherein R$^1$, R$^a$ and Z are as above defined, by reaction with an appropriate source of boron, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron in the presence of a suitable catalyst, such as but not limited to 1,1'bis(diphenylphosphino)ferrocenedichloro palladium(II), dichlorobis(triphenylphosphine)palladium(II), Pd(PPh$_3$)$_4$, Pd(OAc)$_2$, Pd$_2$(dba)$_3$, Pd(Cl)$_2$(PPh$_3$)$_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

The compounds of Formula (VII), wherein R$^1$, R$^a$ and Z are as above defined, can be reacted with 5-bromo-2-iodopyrimidine to give the compounds of Formula (IIa), wherein R$^1$, R$^a$ and Z are as above defined, by a Suzuki-Miyura coupling reaction. General protocols for such coupling are given below in the Examples: in a typical procedure, the 5-bromo-2-iodopyrimidine and the boronic acid or ester (xx) are heated in a suitable solvent, such as THF, toluene or dioxane, in the presence or absence of water as a co-solvent, in the presence of a base, such as Cs$_2$CO$_3$, K$_2$CO$_3$, CsF, and with an appropriate catalyst such as but not limited to dichlorobis(triphenylphosphine)palladium(II), Pd(PPh$_3$)$_4$ or 1,1'-bis(diphenylphosphino)ferrocenedichloro palladium(II), Pd(OAc)$_2$, Pd$_2$(dba)$_3$, Pd(Cl)$_2$(PPh$_3$)$_2$ or Pd/C in the presence or absence of an additional ligand, such as but not limited to P(tBu)$_3$, P(oTol)$_3$, PPh$_3$, BINAP. This coupling reaction can be carried out at a temperature between about 20° C. to about 150° C., preferably at about 120° C., for a few minutes to a few hours, possibly under microwave irradiation.

Scheme 2

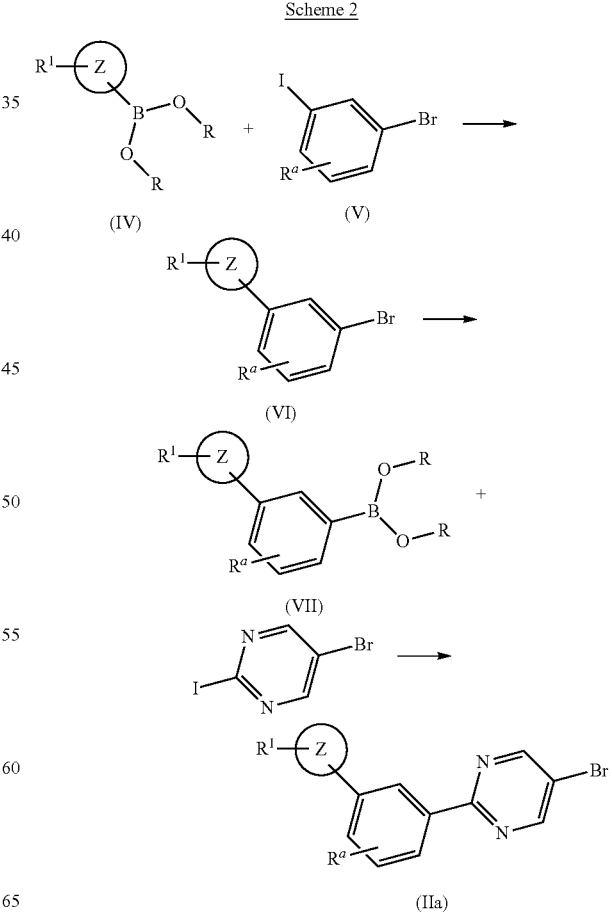

Alternatively, compounds of formula (I) wherein $R^1$, $R^2$, $R^a$, $R^b$ and Z are as above defined can be prepared by Suzuki-Miyura coupling reaction between a compound of Formula (VIII), wherein $R^1$, $R^a$ and Z are as above defined and R is H or an alkyl group, and a compound of Formula (IX) wherein $R^2$ and $R^b$ are as above defined and X is an halogen (preferably bromine or iodine) or a triflate group as outlined in Scheme 3. General protocols for such coupling are given below in the Examples, using conditions and methods well known to those skilled in the art to perform such coupling (see for example Miyaura, N.; Suzuki, A. Chem. Rev. 1995, 95, 2457; Takahiro I. and Toshiaki M., Tetrahedron Lett. 2005, 46, 3573-3577). In a typical procedure, an aryl halide of Formula (II) and a boronic acid or ester of Formula (III) are heated in a suitable solvent, such as THF, toluene or dioxane, in the presence or absence of water as a co-solvent, in the presence of a base, such as $Cs_2CO_3$, $K_2CO_3$, CsF, and with an appropriate catalyst such as but not limited to dichlorobis(triphenylphosphine)palladium(II), $Pd(PPh_3)_4$ or 1,1'-bis(diphenylphosphino)ferrocenedichloro palladium(II), $Pd(OAc)_2$, $Pd_2(dba)_3$, $Pd(Cl)_2(PPh_3)_2$ or Pd/C in the presence or absence of an additional ligand, such as but not limited to $P(tBu)_3$, $P(oTol)_3$, $PPh_3$, BINAP. This coupling reaction can be carried out at a temperature between about 20° C. to about 150° C., preferably at about 120° C., for a few minutes to a few hours, possibly under microwave irradiation. Compounds of Formula (VIII), wherein $R^1$, $R^a$ and Z are as above defined and R is H or an alkyl group, can be prepared from compounds of Formula II, wherein $R^1$, $R^a$ and Z are as above defined and X is an halogen (preferably bromine or iodine) or a triflate group, by reaction with an appropriate diboron derivative, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron, in the presence of a suitable catalyst, such as but not limited to 1,1'bis(diphenylphosphino)ferrocenedichloro palladium(II), dichlorobis(triphenylphosphine)palladium(II), $Pd(PPh_3)_4$, $Pd(OAc)_2$, $Pd_2(dba)_3$, $Pd(Cl)_2(PPh_3)_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

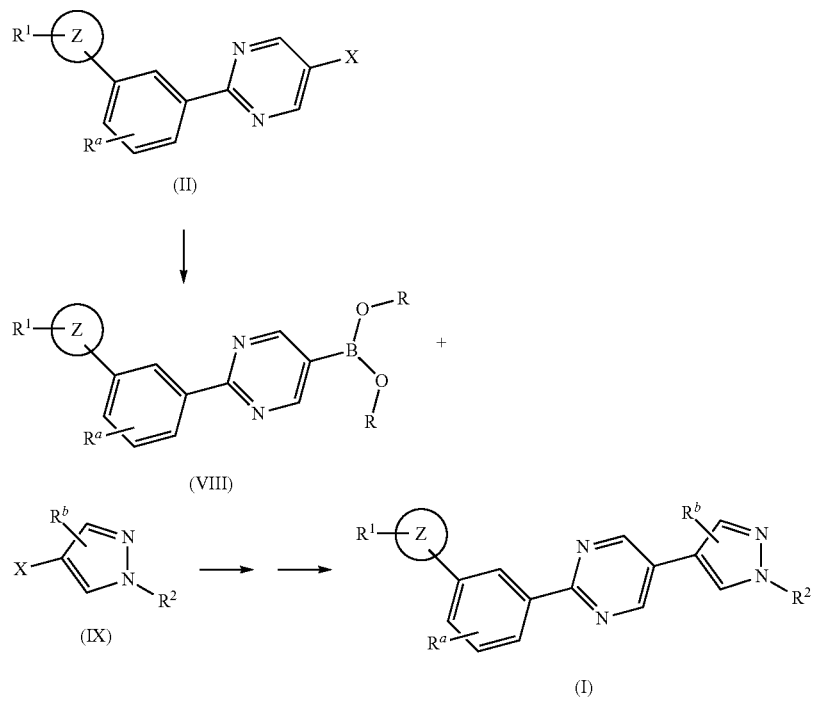

Scheme 3

Alternatively, compounds of Formula I, wherein $R^1$, $R^2$, $R^a$, $R^b$ and Z are as above defined, can be prepared as depicted in Scheme 4. A 2-aminopyrimidine of Formula (X), wherein X is an halogen (preferably iodine or bromine) or a trifluoromethanesulfonate group, is coupled with a boronic acid derivative of Formula (III), wherein $R^2$, $R^b$ are as above defined and R is H or an alkyl group to give a compound of general formula (XI) wherein $R^2$ and $R^b$ are as above defined under Suzuki-Miyaura conditions, well known to those skilled in the art to perform such couplings, as described above.

General protocols for such coupling are given below in the Examples, using conditions and methods well known to those skilled in the art to perform such couplings. The resulting 2-aminopyridine of Formula (XI), wherein $R^2$ and $R^b$ are as above defined, can be converted to a 2-iodopyrimidine of Formula (XII), wherein $R^2$ and $R^b$ are as above defined, for example by reaction with a suitable source of iodine, such as but not limited to diiodomethane, iodine, N-iodosuccinimide, in the presence of an alkyl nitrite such as but not limited to tert-butyl nitrite or iso-pentyl nitrite, in the presence of copper (I) iodide, in a suitable solvent, such as but not limited to THF or dioxane, at a temperature between about 20° C. to about 150° C., preferably at about 80-100° C., for a few hours.

Compounds of Formula (XIV), wherein $R^2$, $R^a$, and $R^b$ are as above defined, can be obtained by coupling of a compound of Formula (XII), wherein $R^2$ and $R^b$ are as above defined, with a boronic acid derivative of Formula (XIII), wherein $R^a$ is as above defined and R is H or an alkyl group, under Suzuki-Miyaura conditions, well known to those skilled in the art to perform such couplings, as described above.

Conversion of compounds of Formula (XIV), wherein $R^2$, $R^a$, and $R^b$ are as above defined, to compounds of Formula (XV), wherein $R^2$, $R^a$, and $R^b$ are as above defined, can be accomplished using similar conditions as described above for the conversion of an aromatic or heteroaromatic amine into an aromatic or heteroaromatic iodide, for example by reaction with a suitable source of iodine, such as but not limited to diiodomethane, iodine, N-iodosuccinimide, in the presence of an alkyl nitrite such as but not limited to tert-butyl nitrite or iso-pentyl nitrite, in the presence of copper (I) iodide, in a suitable solvent, such as but not limited to THF or dioxane, at a temperature between about 20° C. to about 150° C., preferably at about 80-100° C., for a few hours. Finally, compounds of Formula I, wherein $R^1$, $R^2$, $R^a$, $R^b$ and Z are as above defined, can be obtained by coupling of a compound of Formula (XV), wherein $R^2$, $R^a$, and $R^b$ are as above defined, with a boronic acid derivative of Formula (IV), wherein $R^1$ and Z are as above defined and R is H or an alkyl group, under Suzuki-Miyaura conditions, well known to those skilled in the art to perform such couplings, as described above.

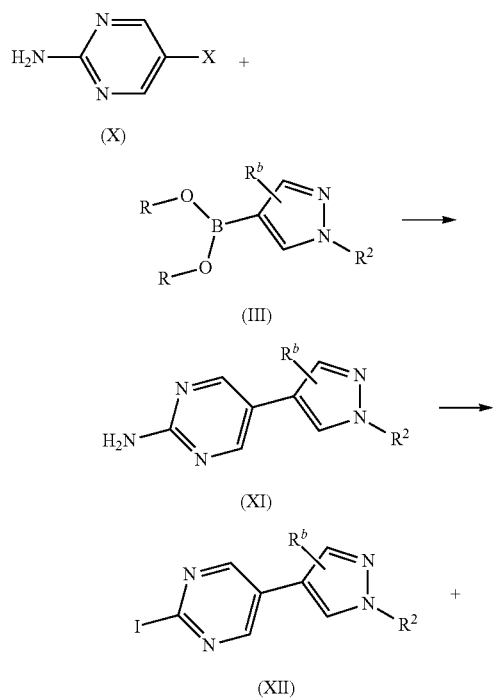

Scheme 4

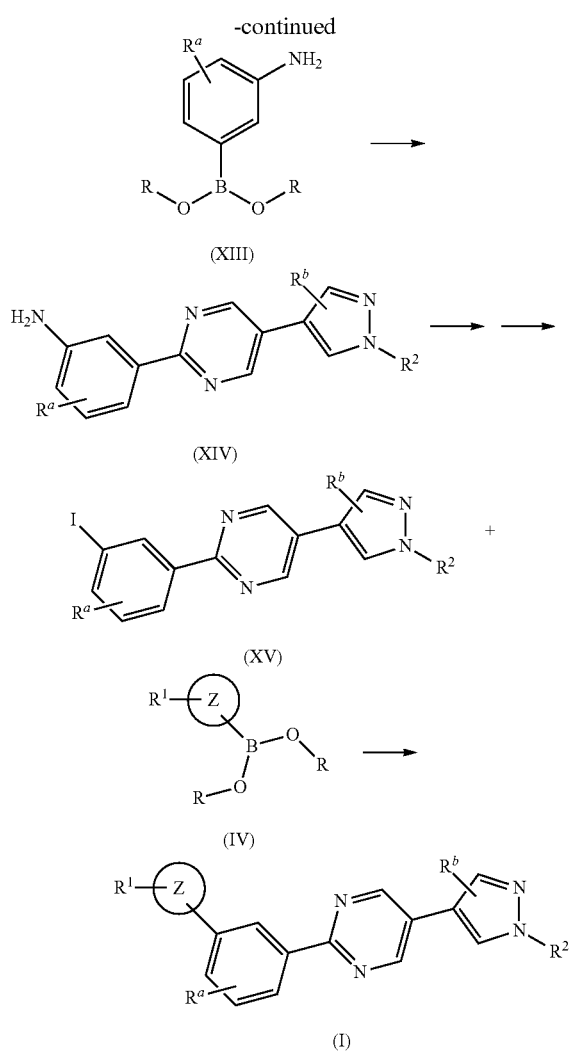

Alternatively, compounds of Formula I, wherein $R^1$, $R^2$, $R^a$, $R^b$ and Z are as above defined, can be prepared as depicted in Scheme 5. Aryl iodides of Formula (XV), wherein $R^2$, $R^a$ and $R^b$ are as above defined, can be converted to compounds of Formula (XVI), wherein $R^2$, $R^a$ and $R^b$ are as above defined and R is H or an alkyl group, by reaction with an appropriate diboron derivative, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron, in the presence of a suitable catalyst, such as but not limited to 1,1'bis(diphenylphosphino)ferrocenedichloro palladium(II), dichlorobis(triphenylphosphine)palladium(II), Pd(PPh$_3$)$_4$, Pd(OAc)$_2$, Pd$_2$(dba)$_3$, Pd(Cl)$_2$(PPh$_3$)$_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to about 150° C., preferably at about 120° C., for a few minutes to a few hours, possibly under microwave irradiation.

Compounds of Formula I, wherein $R^1$, $R^2$, $R^a$, $R^b$ and Z are as above defined, can be obtained by coupling of a compound of Formula (XVI), wherein $R^2$, $R^a$ and $R^b$ are as above defined and R is H or an alkyl group, with a compound of Formula (XVII), wherein $R^1$ and Z are as above defined, under Suzuki-Miyaura conditions, well known to those skilled in the art to perform such couplings, as described above.

Scheme 5

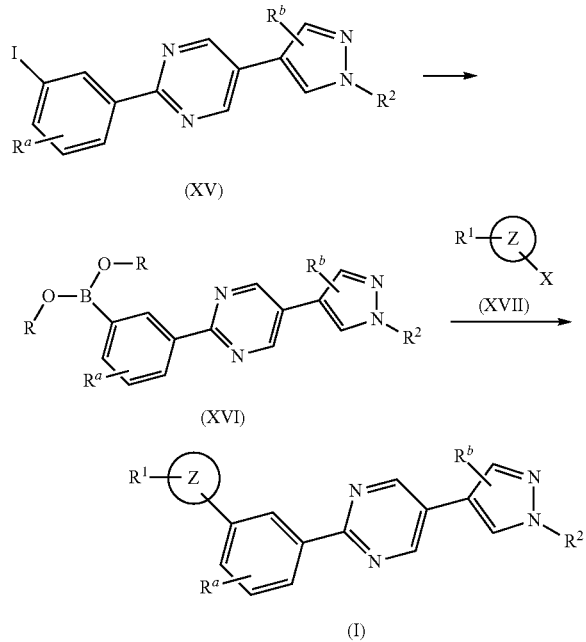

(I)

Alternatively, compounds of formula (I) wherein $R^1$, $R^2$, $R^a$, $R^b$ and Z are as above defined can be prepared by Suzuki-Miyura coupling reaction between a compound of Formula (XII), wherein $R^2$ and $R^b$ are as above defined, and a compound of Formula (VII) wherein $R^1$, $R^a$ and Z are as above defined and R is H or an alkyl group as outlined in Scheme 6. The reaction can be carried out using the general conditions described above. General protocols for such coupling are given below in the Examples, using conditions and methods well known to those skilled in the art to perform such couplings.

Scheme 6

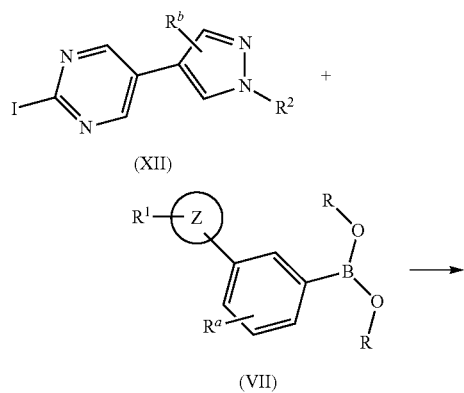

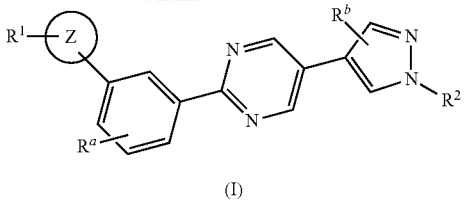

(I)

Alternatively, compounds of Formula (I), wherein $R^1$, $R^2$, $R^a$, $R^b$ and Z are as above defined, can be prepared as depicted in Scheme 7 from compounds of Formula (Ib), wherein $R^1$, $R^a$, $R^b$ and Z are as above defined, prepared following one of the routes described above, by reaction with a compound of Formula (XVIII), wherein $R^2$ is as above defined, but not H and LG is a leaving group, such as bromine, chlorine, alkylsulfonate or any other suitable leaving group known to those skilled in the art. General protocols for such transformation are given below in the Examples, using conditions and methods well known to those skilled in the art. In a typical procedure, a compound of Formula (Ia) is treated with a base, such as but not limited to NaH, $K_2CO_3$, $Cs_2CO_3$, LDA, LHMDS, preferably NaH, and with a compound of Formula (XVIII), in a suitable solvent like THF, dioxane, DMF, DMA, at a temperature between −20° C. to about 150° C., for a time between a few minutes to a few hours.

Alternatively, as depicted in Scheme 7, compounds of Formula (I), wherein $R^1$, $R^2$, $R^a$, $R^b$ and Z are as above defined, can be prepared from compounds of Formula (Ib), wherein $R^1$, $R^a$, $R^b$ and Z are as above defined, prepared following one of the routes described above, by reaction with an alcohol of Formula (XIX), wherein $R^2$ is as above defined, but not H, using conditions well known to those skilled in the art for a Mitsunobu reaction (see for example Hughes, D. L. *Organic Reactions* (New York), 1992, 42, 335-656; Reynolds, A. J.; Kassiou, M. *Current Organic Chemistry*, 2009, 13 (16); 1610-1632). Typically, the reaction takes place in the presence of a phosphine, such as but not limited to $P(tBu)_3$, $PPBu_3$, $P(oTol)_3$, $PPh_3$, in the presence of an azadicarboxylate, such as but not limited to diethylazadicarboxylate, diisopropylazadicarboxylate, Tetramethylazodicarboxamide, in a solvent such as THF, dioxane, DCM, DCE, at a temperature between −20° C. to about 150° C., preferably at room temperature, for a time between a few minutes to a few hours.

Scheme 7

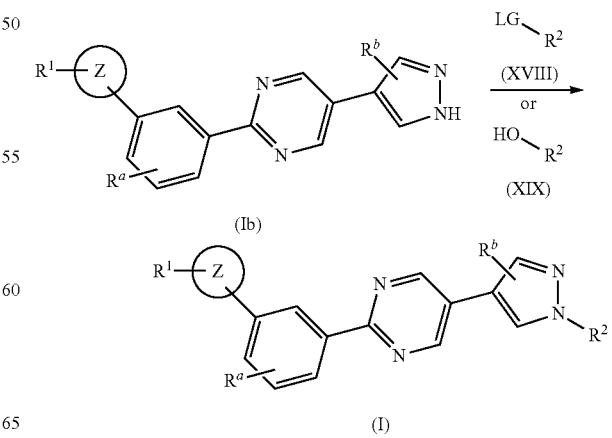

Compounds of formula (III) wherein $R^2$ and $R^b$ are as above defined and R is H or an alkyl group can be prepared from compounds of formula (IX) wherein $R^2$ and $R^b$ are as above defined and X is an halogen (preferably iodine or bromine) or a trifluoromethanesulfonate group by reaction with an appropriate source of boron, such as but not limited to bis(pinacolato)diboron, bis(catecholate)diboron, bis(diethyl-D-tartrate glycolato)diboron, bis(hexyleneglycolato)diboron, bis(neopentylglycolato)diboron, preferably bis(pinacolato)diboron in the presence of a suitable catalyst, such as but not limited to 1,1'bis(diphenylphosphino)ferrocenedichloropalladium(II), dichlorobis(triphenylphosphine)palladium(II), Pd(PPh$_3$)$_4$, Pd(OAc)$_2$, Pd$_2$(dba)$_3$, Pd(Cl)$_2$(PPh$_3$)$_2$, preferably 1,1'bis(diphenylphosphino)ferrocenedichloro palladium(II), in the presence of a suitable base such as but not limited to potassium acetate, cesium fluoride, potassium carbonate, preferably potassium acetate, in the presence of a solvent such as but not limited to THF, dioxane, DCE, DMF, preferably THF or dioxane, at a temperature between about 20° C. to ab out 150° C., preferably at about 120° C., for a few minutes to a few hours, possibly under microwave irradiation as depicted in scheme 8.

Scheme 8

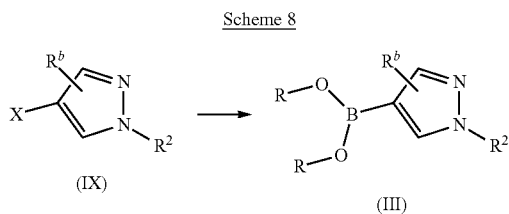

Compounds of formula (IX) wherein $R^2$ and $R^b$ are as above defined and X is a halogen can be obtained by alkylation or Misunobu reaction of a pyrazole of general formula (XX) as depicted in scheme 9 using similar conditions as the one described above for transformation of Scheme 7.

Scheme 9

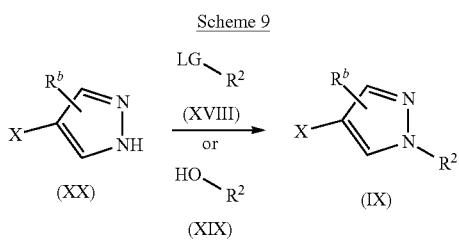

Alternatively, the alkylation or Mitsunobu reaction can take place on boronic intermediate (IIIa) wherein $R^b$ is as above defined and R is H or an alkyl group as depicted in scheme 10.

Scheme 10

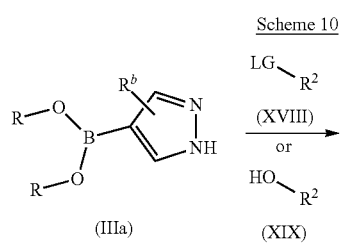

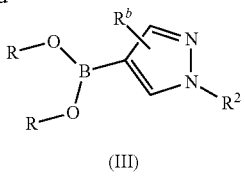

Compounds of this invention can be isolated in association with solvent molecules by crystallization from an appropriate solvent or by evaporation of an appropriate solvent.

The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C.

Compounds of the formula (I) and related formulae can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, further-more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

The formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called pro-drug compounds.

The term "prodrug derivatives" is taken to mean compounds of the formula I which have been modified with, for example, alkyl or acyl groups, sugars or oligopeptides and which are rapidly cleaved in the organism to form the active compounds.

Preferably "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press:

New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The formula (I) and related formulae also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

Methods of Use

The present invention furthermore relates to a method for treating a subject suffering from a IRAK related disorder, comprising administering to said subject an effective amount of a compound of formula I and related formulae. The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality. The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

Preferably, disorders associated with IRAK are selected from Rheumatoid Arthritis Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Crohn's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, Cancer.

Preferred compounds of formula (I), and related formulae exhibit a IC50 for the binding to IRAK of less than about 5 μM, preferably less than about 1 μM and even more preferably less than about 0.100 μM.

Compounds according to formula (I), and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula (I), and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I), and related formulae which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), and related formulae, which contain an acid center, with a suitable base. Both types of salts may be formed or interconverted using ion-exchange resin techniques.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

In the following the present invention shall be illustrated by means of some examples, which are not construed to be viewed as limiting the scope of the invention.

EXPERIMENTAL

In the following the present invention shall be illustrated by means of some examples, which are not construed to be viewed as limiting the scope of the invention.

General:

$^1$H-NMR spectra were acquired on a Bruker Avance III 400 or a Bruker DPX-300 MHz. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), qt (quintuplet) or brs (broad).

Mass spectra were obtained on Agilent 1200 Series mass spectrometers from Agilent Technologies, using either Atmospheric Chemical Ionization (APCI) or Electrospray Ionization (ESI). Column: XBridge C8, 3.5 µm, 4.6×50 mm; Solvent A: water+0.1% TFA; Solvent B: ACN+0.1% TFA; Flow: 2 mL/min; Gradient: 0 min: 5% B, 8 min: 100% B, 8.1 min: 100% B, 8.5 min: 5% B, 10 min 5% B or a LC/MS Waters ZMD (ESI). HPLC data were obtained using Agilent 1100 series HPLC from Agilent technologies using a column (XBridge C8, 3.5 µm, 4.6×50 mm) and two mobile phases (mobile phase A: water+0.1% TFA; mobile phase B: ACN+ 0.1% TFA). The flow rate was 2 mL/min. The gradient method was: 0 min: 5% B; 8 min: 100% B; 8.1 min: 100% B; 8.5 min: 5% B; 10 min 5% B, unless otherwise indicated.

The microwave reactions were conducted using Biotage Initiator Microwave Synthesizer or a single mode microwave reactor Emrys™ Optimiser using standard protocols that are known in the art.

The compounds of the invention were prepared from readily available starting materials by several synthetic approaches, using both solution-phase and solid-phase chemistry protocols or mixed solution and solid phase protocols. Examples of synthetic pathways are described below in the examples. Unless otherwise stated, compounds of the invention obtained as a racemic mixture can be separated to provide an enantiomerically enriched mixture or a pure enantiomer.

The commercially available starting materials used in the following experimental description were purchased from Aldrich or Sigma or ABCR unless otherwise reported. SPE cartridges were purchased from IST and used following supplier recommendations.

Example 1: [2-(4-{2-[3-(1-Methyl-1H-pyrazol-4-yl)-phenyl]-pyrimidin-5-yl}-pyrazol-1-yl)-ethyl]-carbamic acid tert-butyl ester (6)

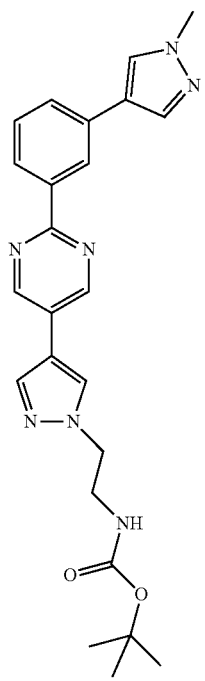 [SMILES: Cn1cc(-c2cccc(-c3ncc(-c4cnn(CCNC(=O)OC(C)(C)C)c4)cn3)c2)cn1]

Step 1: 4-(3-Bromo-phenyl)-1-methyl-1H-pyrazole

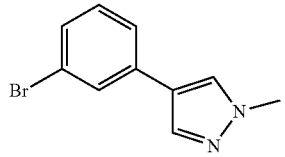

1-Bromo-3-iodobenzene (2.93 mL; 22.98 mmol; 1.00 eq.) was dissolved in DMF (40.00 mL) and then 1-Methyl-4-(4,4,5,5-tetramethyl-[1,3,2]dioxaborolan-2-yl)-1H-pyrazole (5.02 g; 24.12 mmol; 1.05 eq.) was added in one portion followed by a solution of NaHCO3 (2.32 g; 27.57 mmol; 1.20 eq.) in water (26 mL) dropwise. The reaction was degassed with nitrogen and bis(triphenylphosphine)palladium(II) chloride (80.64 mg; 0.11 mmol; 0.01 eq.) was added. The reaction mixture was stirred at 90° C. overnight. LCMS at 21 hr indicated the reaction was complete. The reaction mixture was cooled to room temperature, diluted with water (200 mL) and extracted with ethyl acetate (3×80 mL). The combined organic phase was washed with water (2×75 mL) and brine (1×75 mL); dried (Na2SO4); filtered; and concentrated to a golden oil. The oil was purified via flash chromatography (ethyl acetate/hexanes) to yield 4.83 g (89%) of 4-(3-Bromo-phenyl)-1-methyl-1H-pyrazole as a golden oil. HPLC: 99% purity. MS (ESI+): 237, 239.

Step 2: 5-Bromo-2-[3-(1-methyl-1H-pyrazol-4-yl)-phenyl]-pyrimidine

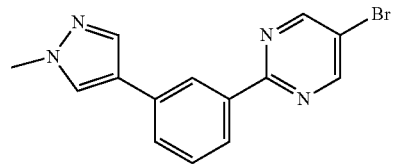 [SMILES: Cn1cc(-c2cccc(-c3ncc(Br)cn3)c2)cn1]

4-(3-Bromo-phenyl)-1-methyl-1H-pyrazole (4.82 aq; 20.33 mmol; 1.00 eq.) was dissolved in 1,4-dioxane (75.00 mL), then bis(pinacolato)diboron, (5.68 g; 22.36 mmol; 1.10 eq.) was added followed by potassium acetate (4.99 g; 50.82 mmol; 2.50 eq.). The mixture was degassed before adding tetrakis(triphenylphosphine)palladium (234.92 mg; 0.20 mmol; 0.01 eq.). The reaction mixture was heated at 100° C. overnight. After 13 hr the reaction was cooled to room temperature and a solution of K2CO3 (8.43 g; 60.99 mmol; 3.00 eq.) in water (25.00 mL) was added. The reaction mixture was stirred for 15 min while bubbling N2 through the solution. 5-Bromo-2-iodo-pyrimidine (6.37 g; 22.36 mmol; 1.10 eq.) in dioxane (10 mL) was added followed by Tetrakis(triphenylphosphine) palladium (234.92 mg; 0.20 mmol; 0.01 eq.). The reaction mixture was stirred at 100° C. under N2 atmosphere. LCMS at 21 hr indicated the reaction was complete. The reaction was cooled to room temperature, added to water (500 mL), and extracted with ethyl acetate (2×250 mL). The organic layer was filtered through a celite plug; washed with water (1×250 mL) and brine (1×100 mL); dried (Na2SO4); filtered; and concentrated to provide an orange solid. The solid was recrystallized in n-butanol (40 mL) to provide 2.75 g (43%) of 5-Bromo-2-[3-(1-methyl- 1H-pyrazol-4-yl)-phenyl]-pyrimidine as a light tan solid. HPLC: 98% purity. MS (ESI+): 315, 317.

Step 3: [2-(4-Iodo-pyrazol-1-yl)-ethyl]-carbamic acid tert-butyl ester

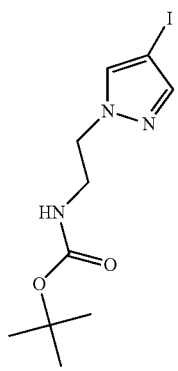 [SMILES: CC(C)(C)OC(=O)NCCn1cc(I)cn1]

In a 20 mL reaction vial with a magnetic stirbar a mixture of toluene-4-sulfonic acid 2-tert-butoxycarbonylamino-ethyl ester (640.00 mg; 2.03 mmol; 1.00 eq.), 4-Iodo-1H-pyrazole (393.62 mg; 2.03 mmol; 1.00 eq.) and cesium carbonate (991.76 mg; 3.04 mmol; 1.50 eq.) in DMA (5.00 mL) was heated at 100° C. for 1 h under N2 atmosphere. LCMS indicated the reaction was complete. The stirring reaction was diluted with EtOAc (50 mL) and washed with water (2×20 mL) and brine (1×20 mL). The organic layer was dried over Na2SO4, filtered, and concentrated under high vacuum to provide 548 mg (80%) of [2-(4-Iodo-pyrazol-1-yl)-ethyl]-carbamic acid tert-butyl ester as an off-white solid. MS (ESI+): 338.

Step 4: [2-(4-{2-[3-(1-Methyl-1H-pyrazol-4-yl)-phenyl]-pyrimidin-5-yl}-pyrazol-1-yl)-ethyl]-carbamic acid tert-butyl ester (6)

In a 40 mL reaction vial a mixture of 5-bromo-2-[3-(1-methyl-1H-pyrazol-4-yl)-phenyl]-pyrimidine (444.39 mg; 1.41 mmol; 1.00 eq.), 4,4,5,5,4',4',5',5'-octamethyl-[2,2']bi[[1,3,2]dioxaborolanyl] (0.39 g; 1.55 mmol; 1.10 eq.), potassium; acetate (0.21 g; 2.11 mmol; 1.50 eq.) and trans-dichlorobis(tricyclohexylphosphine)palladium(II) (10.41 mg; 0.01 mmol; 0.01 eq.) was prepared in 1,4-dioxane (10.50 mL) and heated at 100° C. LCMS at 15 hr indicated the reaction was complete. The reaction was cooled to room temperature and [2-(4-Iodo-pyrazol-1-yl)-ethyl]-carbamic acid tert-butyl ester (522.93 mg; 1.55 mmol; 1.10 eq.) in 1,4-dioxane (2.0 mL), and K2CO3 (0.58 g; 4.23 mmol; 3.00 eq.) in water (3.50 mL) were added under N2 atmosphere. Nitrogen was bubbled through the solution for 10 min and then trans-dichlorobis(tricyclohexylphosphine)palladium (II) (10.41 mg; 0.01 mmol; 0.01 eq.) was added. The mixture heated at 100° C. and stirred over night.

LCMS at 18 hr indicated the reaction was complete. The reaction was cooled to room temperature, diluted with ethyl acetate (20 mL) and water (5 mL), and filtered through celite. The layers were separated. The organic layer was concentrated and then purified via flash chromatography (ethyl acetate) to provide 300 mg (48%) of [2-(4-{2-[3-(1-Methyl-1H-pyrazol-4-yl)-phenyl]-pyrimidin-5-yl}-pyrazol-1-yl)-ethyl]-carbamic acid tert-butyl ester as an off-white solid. HPLC: 97% purity. MS (ESI+): 446. ¹HNMR (400 MHz, DMSO-d6) δ 9.16 (s, 2H), 8.54 (d, 1H), 8.41 (s, 1H), 8.26 (s, 1H), 8.23 (dd, 1H), 8.16 (s, 1H), 7.92 (s, 1H), 7.72 (dd, 1H), 7.52 (t, 1H), 6.99 (t, 1H), 4.21 (t, 2H), 3.38 (q, 2H), 1.37 (s, 9H).

Example 2: 3-(4-{2-[3-(1-Methyl-1H-pyrazol-4-yl)-phenyl]-pyrimidin-5-yl}-pyrazol-1-yl)-piperidine-1-carboxylic acid tert-butyl ester (7)

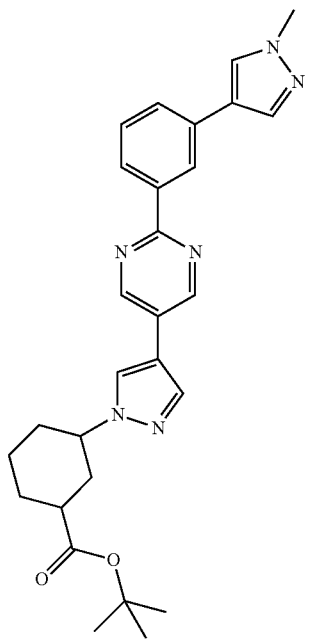 [SMILES: Cn1cc(-c2cccc(-c3ncc(-c4cnn(C5CCCC(C(=O)OC(C)(C)C)C5)c4)cn3)c2)cn1]

Step 1: 3-(4-Iodo-pyrazol-1-yl)-piperidine-1-carboxylic acid tert-butyl ester

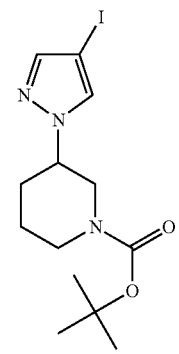 [SMILES: CC(C)(C)OC(=O)N1CCCC(n2cc(I)cn2)C1]

In a 20 mL reaction vial with a magnetic stirbar a mixture of 3-(toluene-4-sulfonyloxy)-piperidine-1-carboxylic acid tert-butyl ester (1.12 g; 3.15 mmol; 1.00 eq.), 4-Iodo-1H-pyrazole (611.20 mg; 3.15 mmol; 1.00 eq.) and cesium carbonate (1.54 g; 4.73 mmol; 1.50 eq.) in DMA (5.00 mL) was heated at 100° C. for 1 h under N2 atmosphere. LCMS at 1 hr indicated the reaction was complete. The reaction was diluted with ethyl acetate (50 mL) and washed with water (2×20 mL) and brine (1×20 mL). The organic layer was dried over Na2SO4, filtered, and concentrated to yield 920 mg (77%) of 3-(4-Iodo-pyrazol-1-yl)-piperidine-1-carboxylic acid tert-butyl ester as a colorless oil. MS (ESI+): 378.

Step 2: 3-(4-{2-[3-(1-Methyl-1H-pyrazol-4-yl)-phenyl]-pyrimidin-5-yl}-pyrazol-1-yl)-piperidine-1-carboxylic acid tert-butyl ester (7)

In a 40 mL reaction vial a mixture of intermediate 5-Bromo-2-[3-(1-methyl-1H-pyrazol-4-yl)-phenyl]-pyrimidine (315.17 mg; 1.00 mmol; 1.00 eq.) from example 1, 4,4,5,5,4',4',5',5'-octamethyl-[2,2']bi[[1,3,2]dioxaborolanyl] (279.33 mg; 1.10 mmol; 1.10 eq.), potassium acetate (147.21 mg; 1.50 mmol; 1.50 eq.) and trans-dichlorobis(tricyclohexylphosphine)palladium(II), (7.38 mg; 0.01 mmol; 0.01 eq.) was prepared in 1,4-dioxane (10.50 mL) and heated at 100° C. LCMS at 15 hr indicated the reaction was complete. The reaction was cooled to room temperature and then 3-(4-Iodo-pyrazol-1-yl)-piperidine-1-carboxylic acid tert-butyl ester (414.94 mg; 1.10 mmol; 1.10 eq.) from step 1 in 1,4-dioxane (2.0 mL), and K2CO3 (0.41 g; 3.00 mmol; 3.00 eq.) in water (3.50 mL) were added all under N2 atmosphere. Nitrogen was bubbled through the solution for 10 min and then trans-dichlorobis(tricyclohexylphosphine)palladium(II) (7.38 mg; 0.01 mmol; 0.01 eq.) was added. The mixture heated at 100° C. and stirred over night. LCMS at 18 hr indicated the reaction was complete. The reaction was cooled to room temperature and diluted with ethyl acetate (20 mL) and water (5 mL) and filtered through celite. The layers were separated. The organic layer was concentrated and purified via flash chromatography (ethyl acetate) to provide 290 mg of 3-(4-{2-[3-(1-Methyl-1H-pyrazol-4-yl)-phenyl]-pyrimidin-5-yl}-pyrazol-1-yl)-piperidine-1-carboxylic acid tert-butyl ester as an off-white solid. HPLC: 99% purity. MS (ESI+): 486. $^1$H NMR (400 MHz, DMSO-d6) δ 9.17 (d, 2H), 8.61-8.51 (m, 2H), 8.26 (s, 1H), 8.23 (dd, 1H), 8.19 (s, 1H), 7.93 (s, 1H), 7.72 (dd, 1H), 7.52 (t, 1H), 4.34-4.10 (m, 1H), 3.90 (s, 3H), 3.86 (s, 1H), 2.91 (t, 1H), 2.26-2.13 (m, 1H), 2.12-1.98 (m, 1H), 1.83 (d, 1H), 1.56 (t, 1H), 1.42 (s, 9H).

Example 3: 4-(4-{2-[3-(1-Methyl-1H-pyrazol-4-yl)-phenyl]-pyrimidin-5-yl}-pyrazol-1-yl)-piperidine-1-carboxylic acid tert-butyl ester (8)

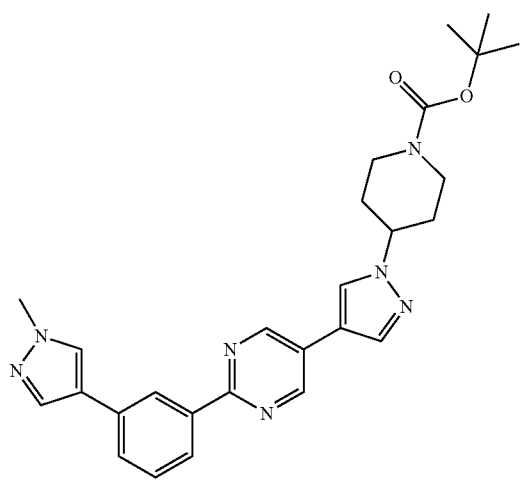 [SMILES: Cn1cc(-c2cccc(-c3ncc(-c4cnn(C5CCN(C(=O)OC(C)(C)C)CC5)c4)cn3)c2)cn1]

Step 1: 4-(4-Iodo-pyrazol-1-yl)-piperidine-1-carboxylic acid tert-butyl ester

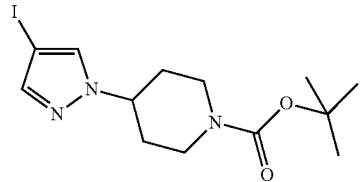 [SMILES: CC(C)(C)OC(=O)N1CCC(n2cc(I)cn2)CC1]

In a 20 mL reaction vial with a magnetic stirbar a mixture of 4-(toluene-4-sulfonyloxy)-piperidine-1-carboxylic acid tert-butyl ester (1.08 g; 3.04 mmol; 1.00 eq.), 4-Iodo-1H-pyrazole (589.37 mg; 3.04 mmol; 1.00 eq.) and cesium carbonate (1.48 g; 4.56 mmol; 1.50 eq.) in DMA (7.00 mL) was heated at 100° C. for 1 h under N2 atmosphere. LCMS at 1 hr showed indicated the reaction was complete. The reaction was diluted with ethyl acetate (50 mL) and washed with water (2×20 mL) and brine (1×20 mL). The organic layer was dried over Na2SO4, filtered, and concentrated to provide 1.06 g (92%) of 4-(4-Iodo-pyrazol-1-yl)-piperidine-1-carboxylic acid tert-butyl ester as a colorless oil. MS (ESI+): 378.

Step 2: 4-(4-{2-[3-(1-Methyl-1H-pyrazol-4-yl)-phenyl]-pyrimidin-5-yl}-pyrazol-1-yl)-piperidine-1-carboxylic acid tert-butyl ester (8)

In a 40 mL reaction vial a mixture of 5-Bromo-2-[3-(1-methyl-1H-pyrazol-4-yl)-phenyl]-pyrimidine (535.79 mg; 1.70 mmol; 1.00 eq.) from example 1, 4,4,5,5,4',4',5',5'-Octamethyl-[2,2']bi[[1,3,2]dioxaborolanyl] (474.87 mg; 1.87 mmol; 1.10 eq.), potassium; acetate (250.26 mg; 2.55 mmol; 1.50 eq.) and trans-dichlorobis(tricyclohexylphosphine) palladium(II) (12.55 mg; 0.02 mmol; 0.01 eq.) was prepared in 1,4-dioxane (10.50 mL) and heated at 100° C. LCMS at indicated the reaction was complete. The reaction was cooled to room temperature and then 4-(4-Iodo-pyrazol-1-yl)-piperidine-1-carboxylic acid tert-butyl ester (705.40 mg; 1.87 mmol; 1.10 eq.) in dioxane (2 mL) from step 1, and K2CO3 (0.70 g; 5.10 mmol; 3.00 eq.) in water (3.50 mL) were added under N2 atmosphere. Nitrogen was bubbled through the solution for 10 min and then trans-dichlorobis(tricyclohexylphosphine)palladium(II) (12.55 mg; 0.02 mmol; 0.01 eq.) was added. The mixture heated at 100° C. and stirred overnight. LCMS at 18 hr indicated the reaction was complete. The reaction was cooled to room temperature; diluted with EA (20 mL) and water (5 mL); and filtered through celite. The layers were separated and the organic layer was concentrated. Purified via flash chromatography (ethyl acetate) to provide 518 mg (63%) of 4-(4-{2-[3-(1-Methyl-1H-pyrazol-4-yl)-phenyl]-pyrimidin-5-yl}-pyrazol-1-yl)-piperidine-1-carboxylic acid tert-butyl ester as an off-white solid. HPLC: 100% purity. MS (ESI+): 486. $^1$H NMR (400 MHz, DMSO-d6) δ 9.17 (d, 2H), 8.59-8.50 (m, 2H), 8.26 (s, 1H), 8.23 (dd, 1H), 8.15 (s, 1H), 7.92 (s, 1H), 7.75-7.67 (m, 1H), 7.52 (t, 1H), 4.45 (td, 1H), 4.08 (d, 3H), 3.90 (s, 3H), 2.96 (s, 3H), 2.14-2.04 (m, 2H), 1.83 (qd, 2H), 1.44 (d, 9H).

Example 4: [3-(4-{2-[3-(1-Methyl-1H-pyrazol-4-yl)-phenyl]-pyrimidin-5-yl}-pyrazol-1-yl)-cyclohexyl]-carbamic acid tert-butyl ester (9)

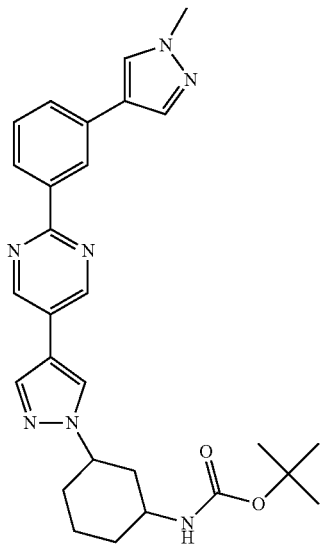 [SMILES: Cn1cc(-c2cccc(-c3ncc(-c4cnn(C5CCCC(NC(=O)OC(C)(C)C)C5)c4)cn3)c2)cn1]

Step 1: [3-(4-Iodo-pyrazol-1-yl)-cyclohexyl]-carbamic acid tert-butyl ester

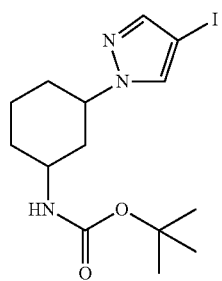 [SMILES: CC(C)(C)OC(=O)NC1CCCC(n2cc(I)cn2)C1]

In a 20 mL reaction vial with a magnetic stirbar a mixture of toluene-4-sulfonic acid 3-tert-butoxycarbonylamino-cyclohexyl ester (1.02 g; 2.76 mmol; 1.00 eq.), 4-Iodo-1H-pyrazole (535.50 mg; 2.76 mmol; 1.00 eq.) and cesium carbonate (1.35 g; 4.14 mmol; 1.50 eq.) in DMA (5.00 mL) was heated at 100° C. for 1 h under N2 atmosphere. LCMS at 1 hr indicated the reaction was complete. The reaction was diluted with ethyl acetate (50 mL) and washed with water (2×20 mL) and brine (1×20 mL). The organic layer was dried over Na2SO4, filtered, and concentrated to yield a brown solid. The solid was triturated with ethyl acetate to provide 922 mg (85%) of [3-(4-Iodo-pyrazol-1-yl)-cyclohexyl]-carbamic acid tert-butyl ester as an off-white solid. MS (ESI+): 392.

Step 2: [3-(4-{2-[3-(1-Methyl-1H-pyrazol-4-yl)-phenyl]-pyrimidin-5-yl}-pyrazol-1-yl)-cyclohexyl]-carbamic acid tert-butyl ester (9)

In a 40 mL reaction vial a mixture of 5-Bromo-2-[3-(1-methyl-1H-pyrazol-4-yl)-phenyl]-pyrimidine (95.18 mg; 0.30 mmol; 1.00 eq.) from example 1, 4,4,5,5,4',4',5',5'-Octamethyl-[2,2']bi[[1,3,2]dioxaborolanyl] (84.36 mg; 0.33 mmol; 1.10 eq.), potassium; acetate (44.46 mg; 0.45 mmol; 1.50 eq.) and trans-dichlorobis(tricyclohexylphosphine) palladium(II) (2.23 mg; 0.00 mmol; 0.01 eq.) was prepared in 1,4-dioxane (6.00 mL) and heated at 100° C. LCMS at 15 hr indicated the reaction was complete. The reaction was cooled to room temperature and then [3-(4-Iodo-pyrazol-1-yl)-cyclohexyl]-carbamic acid tert-butyl ester (129.97 mg; 0.33 mmol; 1.10 eq.) from step 1 in dioxane (2 mL), and K2CO3 (0.13 g; 0.91 mmol; 3.00 eq.) in water (2.00 mL) were added all under N2 atmosphere. Nitrogen was bubbled through the solution for 10 min and then trans-dichlorobis (tricyclohexylphosphine)palladium(II) (2.23 mg; 0.00 mmol; 0.01 eq.) was added. The mixture heated at 100° C. and stirred over night. After 18 hr the reaction was cooled to room temperature; diluted with ethyl acetate (20 mL) and water (5 mL); and filtered through celite. The layers were separated and the organic layer was concentrated. The crude was purified via flash chromatography (ethyl acetate) to provide 68 mg (45%) of [3-(4-{2-[3-(1-Methyl-1H-pyrazol-4-yl)-phenyl]-pyrimidin-5-yl}-pyrazol-1-yl)-cyclohexyl]-carbamic acid tert-butyl ester as a yellow solid. HPLC: 99.7% purity. MS (ESI+): 500. $^1$H NMR (400 MHz, DMSO-d6) δ 9.17 (d, 2H), 8.54 (d, 1H), 8.49 (s, 1H), 8.26 (s, 1H), 8.25-8.19 (m, 1H), 8.13 (s, 1H), 7.92 (s, 1H), 7.75-7.67 (m, 1H), 7.52 (t, 1H), 6.93 (d, 1H), 4.37-4.23 (m, 1H), 3.90 (s, 3H), 3.46 (s, 1H), 2.22 (d, 1H), 2.05 (d, 1H), 1.84 (t, 2H), 1.73-1.58 (m, 2H), 1.41 (d, 8H), 1.21 (dt, 1H).

Example 5: 1-[4-(4-{2-[3-(1-Methyl-1H-pyrazol-4-yl)-phenyl]-pyrimidin-5-yl}-pyrazol-1-yl)-piperidin-1-yl]-propenone (10)

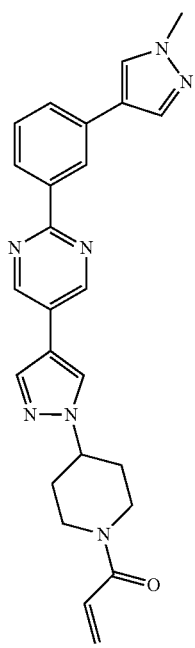 [SMILES: C=CC(=O)N1CCC(n2cc(-c3cnc(-c4cccc(-c5cnn(C)c5)c4)nc3)cn2)CC1]

71

Step 1: 2-[3-(1-Methyl-1H-pyrazol-4-yl)-phenyl]-5-(1-piperidin-4-yl-1H-pyrazol-4-yl)-pyrimidine trifluoroacetate

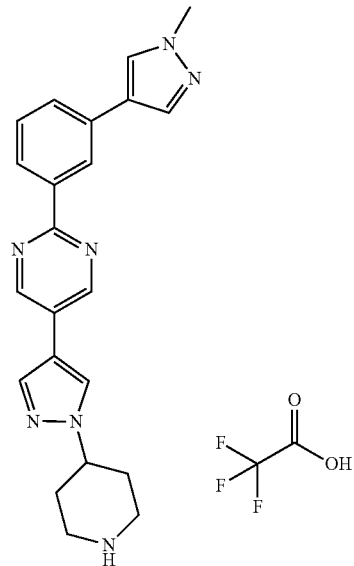 [SMILES: Cn1cc(-c2cccc(-c3ncc(-c4cnn(C5CCNCC5)c4)cn3)c2)cn1 ; O=C(O)C(F)(F)F]

4-(4-{2-[3-(1-Methyl-1H-pyrazol-4-yl)-phenyl]-pyrimidin-5-yl}-pyrazol-1-yl)-piperidine-1-carboxylic acid tert-butyl ester (512.00 mg; 1.05 mmol; 1.00 eq.) from example 3 was suspended in DCM (4.00 mL) and treated with anhydrous trifluoroacetic acid (1.00 mL). The homogeneous reaction was stirred at room temperature for 2 hr. The reaction was concentrated; chased with toluene; and then lyophilized from acetonitrile/water (3:1). The material was carried forward assuming 100% yield. MS (ESI+): 386.

Step 2: 1-[4-(4-{2-[3-(1-Methyl-1H-pyrazol-4-yl)-phenyl]-pyrimidin-5-yl}-pyrazol-1-yl)-piperidin-1-yl]-propenone (10)

In a 20 mL scintillation vial with magnetic stir bar 2-[3-(1-Methyl-1H-pyrazol-4-yl)-phenyl]-5-(1-piperidin-4-yl-1H-pyrazol-4-yl)-pyrimidine trifluoroacetate (259.73 mg; 0.52 mmol; 1.00 eq.) from step 1 was dissolved in DMF (2.00 mL) and DIPEA (362.30 µl; 2.08 mmol; 4.00 eq.). To the stirring homogeneous solution was then added acryloyl chloride (63.37 µl; 0.78 mmol; 1.50 eq.). The reaction was stirred at room temperature overnight. The resulting milky solution was concentrated and then stirred in 1:1 EA/MeOH (3 mL) for 5 min. The solids were filtered; washed with ethyl acetate; and dried to provide 137 mg (60%) of 1-[4-(4-{2-[3-(1-Methyl-1H-pyrazol-4-yl)-phenyl]-pyrimidin-5-yl}-pyrazol-1-yl)-piperidin-1-yl]-propenone as a white solid. HPLC: 96.5% purity. MS (ESI+): 440. $^1$H NMR (400 MHz, DMSO-d6) δ 9.17 (d, 2H), 8.61-8.51 (m, 2H), 8.31-8.20 (m, 2H), 8.16 (s, 1H), 7.92 (s, 1H), 7.77-7.67 (m, 1H), 7.52 (t, 1H), 6.88 (dd, 1H), 6.15 (dd, 1H), 5.72 (dt, 1H), 4.55 (ddt, 2H), 4.21 (d, 1H), 3.90 (s, 2H), 2.89 (q, 1H), 2.22-2.08 (m, 2H), 1.95-1.76 (m, 2H).

72

Example 6: N-[2-(4-{2-[3-(1-Methyl-1H-pyrazol-4-yl)-phenyl]-pyrimidin-5-yl}-pyrazol-1-yl)-ethyl]-acrylamide (13)

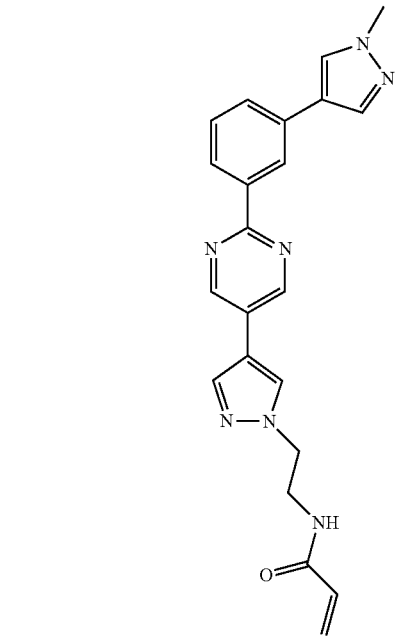 [SMILES: C=CC(=O)NCCn1cc(-c2cnc(-c3cccc(-c4cnn(C)c4)c3)nc2)cn1]

Step 1: 2-(4-{2-[3-(1-Methyl-1H-pyrazol-4-yl)-phenyl]-pyrimidin-5-yl}-pyrazol-1-yl)-ethylamine trifluoroacetate

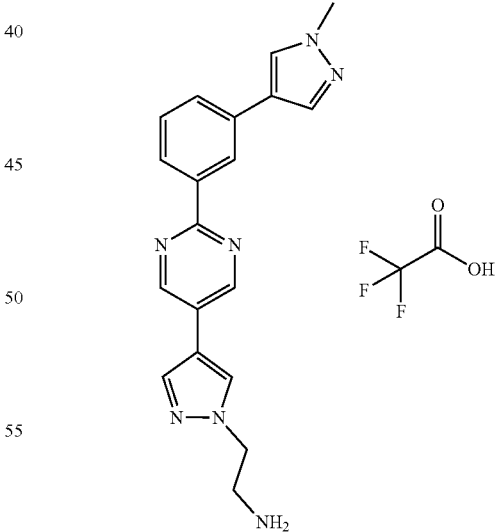

[2-(4-{2-[3-(1-Methyl-1H-pyrazol-4-yl)-phenyl]-pyrimidin-5-yl}-pyrazol-1-yl)-ethyl]-carbamic acid tert-butyl ester (291.00 mg; 0.65 mmol; 1.00 eq.) from example 1 was suspended in DCM (4.00 mL) and treated with anhydrous trifluoroacetic acid (1.00 mL). The homogeneous reaction was stirred at room temperature for 2 hr. The reaction was concentrated; chased with toluene; and then lyophilized from ACN/water (3:1). The material was carried forward assuming 100% yield. MS (ESI+): 346.

Step 2: N-[2-(4-{2-[3-(1-Methyl-1H-pyrazol-4-yl)-phenyl]-pyrimidin-5-yl}-pyrazol-1-yl)-ethyl]-acrylamide (13)

In a 20 mL scintillation vial with magnetic stir bar 2-(4-{2-[3-(1-Methyl-1H-pyrazol-4-yl)-phenyl]-pyrimidin-5-yl}-pyrazol-1-yl)-ethylamine trifluoroacetate (147.02 mg; 0.32 mmol; 1.00 eq.) from step 1 was dissolved in DMF (2.00 mL) and DIPEA (222.96 µl; 1.28 mmol; 4.00 eq.). To the stirring homogeneous solution was then added acryloyl chloride (34.76 mg; 0.38 mmol; 1.20 eq.). The reaction was stirred at room temperature overnight.

The reaction was partially concentrated and directly purified via prep HPLC. Lyophilization of the combined clean fractions afforded 62 mg (49%) of N-[2-(4-{2-[3-(1-Methyl-1H-pyrazol-4-yl)-phenyl]-pyrimidin-5-yl}-pyrazol-1-yl)-ethyl]-acrylamide as a white solid. HPLC: 99.7% purity. MS (ESI+): 400. $^1$H NMR (400 MHz, DMSO-d6) δ 9.16 (d, 2H), 8.54 (d, 1H), 8.45 (s, 1H), 8.27 (d, 2H), 8.23 (dd, 1H), 8.18 (s, 1H), 7.92 (s, 1H), 7.74-7.69 (m, 1H), 7.52 (t, 1H), 6.27-6.06 (m, 2H), 5.61 (dd, 1H), 4.29 (t, 2H), 3.90 (s, 3H), 3.60 (q, 2H).

Example 7: 1-[3-(4-{2-[3-(1-Methyl-1H-pyrazol-4-yl)-phenyl]-pyrimidin-5-yl}-pyrazol-1-yl)-piperidin-1-yl]-propenone (14)

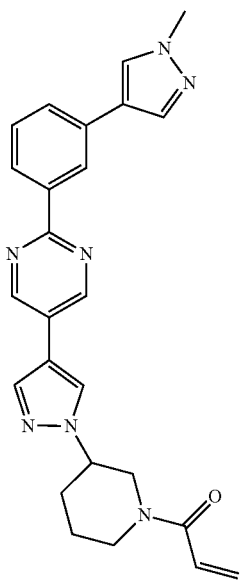 [SMILES: C=CC(=O)N1CCCC(n2cc(-c3cnc(-c4cccc(-c5cnn(C)c5)c4)nc3)cn2)C1]

Step 1: 2-[3-(1-Methyl-1H-pyrazol-4-yl)-phenyl]-5-(1-piperidin-3-yl-1H-pyrazol-4-yl)-pyrimidine trifluoroacetate

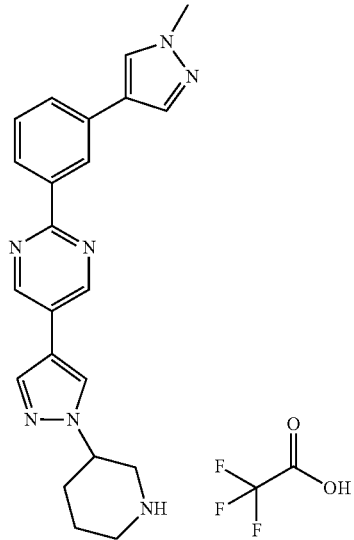 [SMILES: Cn1cc(-c2cccc(-c3ncc(-c4cnn(C5CCCNC5)c4)cn3)c2)cn1 ; O=C(O)C(F)(F)F]

3-(4-{2-[3-(1-Methyl-1H-pyrazol-4-yl)-phenyl]-pyrimidin-5-yl}-pyrazol-1-yl)-piperidine-1-carboxylic acid tert-butyl ester (280.00 mg; 0.58 mmol; 1.00 eq.) from example 2 was suspended in DCM (4.00 mL) and treated with anhydrous trifluoroacetic acid (1.00 mL). The homogeneous reaction was stirred at room temperature for 2 hr and then concentrated; chased with toluene; and lyophilized from ACN/water (3:1). The material was carried forward assuming 100% yield. MS (ESI+): 386.

Step 2: 1-[3-(4-{2-[3-(1-Methyl-1H-pyrazol-4-yl)-phenyl]-pyrimidin-5-yl}-pyrazol-1-yl)-piperidin-1-yl]-propenone (14)

In a 20 mL scintillation vial with magnetic stir bar 2-[3-(1-Methyl-1H-pyrazol-4-yl)-phenyl]-5-(1-piperidin-3-yl-1H-pyrazol-4-yl)-pyrimidine trifluoroacetate (144.85 mg; 0.29 mmol; 1.00 eq.) from step 1 was dissolved in DMF (2.00 mL) and DIPEA (202.05 µl; 1.16 mmol; 4.00 eq.). To the stirring homogeneous solution was then added acryloyl chloride (35.34 µl; 0.43 mmol; 1.50 eq.). The reaction was stirred at room temperature overnight. The reaction was partially concentrated and directly purified via prep HPLC. Lyophilization of the combined clean fractions afforded 87 mg (68%) of 1-[3-(4-{2-[3-(1-Methyl-1H-pyrazol-4-yl)-phenyl]-pyrimidin-5-yl}-pyrazol-1-yl)-piperidin-1-yl]-propenone as a white solid. HPLC: 100% purity. MS (ESI+): 440. $^1$H NMR (400 MHz, DMSO-d6) δ 9.18 (d, 3H), 8.60-8.51 (m, 4H), 8.29-8.17 (m, 6H), 7.93 (s, 2H), 7.72 (dt, 2H), 7.52 (t, 2H), 6.86 (dd, 2H), 6.13 (t, 2H), 5.71 (t, 2H), 4.76-4.62 (m, 1H), 4.27 (q, 4H), 4.06 (d, 1H), 3.90 (s, 5H), 3.60 (t, 1H), 3.13 (dt, 2H), 2.95 (d, 1H), 2.31-2.06 (m, 4H), 1.88 (d, 2H), 1.57 (d, 2H).

Example 8: N-[3-(4-{2-[3-(1-Methyl-1H-pyrazol-4-yl)-phenyl]-pyrimidin-5-yl}-pyrazol-1-yl)-cyclohexyl]-acrylamide (15)

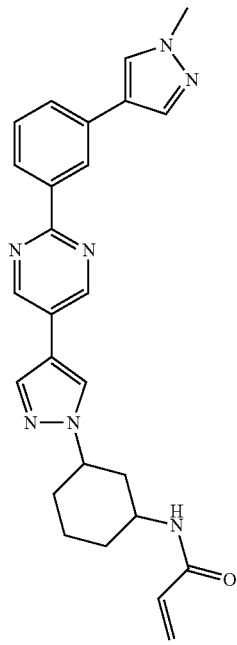 [SMILES: C=CC(=O)NC1CCCC(n2cc(-c3cnc(-c4cccc(-c5cnn(C)c5)c4)nc3)cn2)C1]

Step 1: 3-(4-{2-[3-(1-Methyl-1H-pyrazol-4-yl)-phenyl]-pyrimidin-5-yl}-pyrazol-1-yl)-cyclohexylamine trifluoroacetate

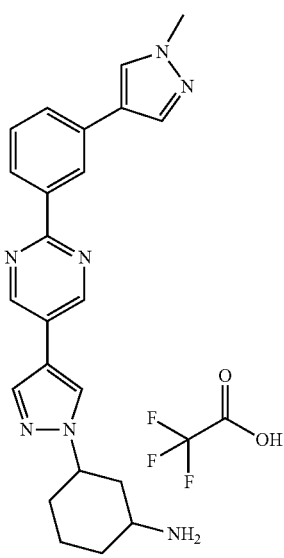

[3-(4-{2-[3-(1-Methyl-1H-pyrazol-4-yl)-phenyl]-pyrimidin-5-yl}-pyrazol-1-yl)-cyclohexyl]-carbamic acid tert-butyl ester (62.00 mg; 0.12 mmol; 1.00 eq.) from example 4 was suspended in DCM (4.00 mL) and treated with anhydrous trifluoroacetic acid (1.00 mL). The homogeneous reaction was stirred at room temperature for 2 hr and then concentrated; chased with toluene; and lyophilized from ACN/water (3:1). The material was carried forward assuming 100% yield. MS (ESI+): 400.

Step 2: N-[3-(4-{2-[3-(1-Methyl-1H-pyrazol-4-yl)-phenyl]-pyrimidin-5-yl}-pyrazol-1-yl)-cyclohexyl]-acrylamide (15)

In a 20 mL scintillation vial with magnetic stir bar 3-(4-{2-[3-(1-Methyl-1H-pyrazol-4-yl)-phenyl]-pyrimidin-5-yl}-pyrazol-1-yl)-cyclohexylamine trifluoroacetate (61.62 mg; 0.12 mmol; 1.00 eq.) from step 1 was dissolved in DMF (4.00 mL) and DIPEA (83.61 µl; 0.48 mmol; 4.00 eq.). To the stirring homogeneous solution was then added acryloyl chloride (14.62 µl; 0.18 mmol; 1.50 eq.). The reaction was stirred at room temperature overnight; and then partially concentrated, and directly purified via prep HPLC. Lyophilization of the combined clean fractions afforded 30 mg (55%) of N-[3-(4-{2-[3-(1-Methyl-1H-pyrazol-4-yl)-phenyl]-pyrimidin-5-yl}-pyrazol-1-yl)-cyclohexyl]-acrylamide as a white solid. HPLC: 100% purity. MS (ESI+): 454. $^1$H NMR (400 MHz, DMSO-d6) δ 9.17 (d, 2H), 8.52 (d, 2H), 8.26 (s, 1H), 8.25-8.20 (m, 1H), 8.15 (d, 2H), 7.92 (s, 1H), 7.74-7.69 (m, 1H), 7.52 (t, 1H), 6.22 (dd, 1H), 6.10 (dd, 1H), 5.59 (dd, 1H), 4.42-4.28 (m, 1H), 3.86 (s, 1H), 2.28 (d, 1H), 2.16-2.03 (m, 1H), 1.89 (d, 2H), 1.71 (q, 2H), 1.61-1.44 (m, 1H), 1.34-1.17 (m, 1H).

Example 9: Ethenesulfonic acid [2-(4-{2-[3-(1-methyl-1H-pyrazol-4-yl)-phenyl]-pyrimidin-5-yl}-pyrazol-1-yl)-ethyl]-amide (16)

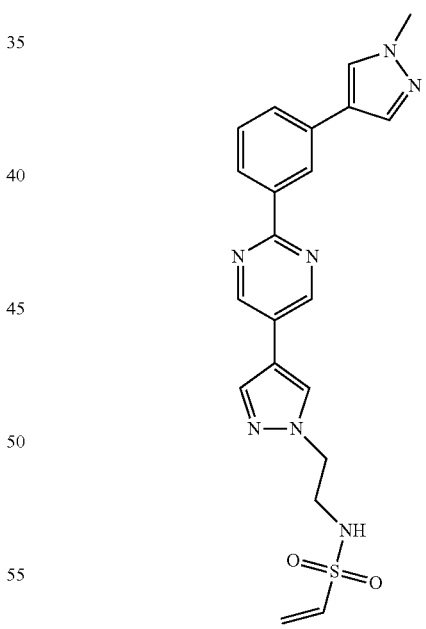

In a 20 mL scintillation vial with magnetic stir bar 2-(4-{2-[3-(1-Methyl-1H-pyrazol-4-yl)-phenyl]-pyrimidin-5-yl}-pyrazol-1-yl)-ethylamine trifluoroacetate (147.02 mg; 0.32 mmol; 1.00 eq.) from example 6 was dissolved in DMF (2.00 mL) and DIPEA (222.96 µl; 1.28 mmol; 4.00 eq.). To the stirring homogeneous solution was then added ethenesulfonyl chloride (37.67 µl; 0.38 mmol; 1.20 eq.). The reaction was stirred at room temperature overnight; partially concentrated; and directly purified via prep HPLC.

Lyophilization of the combined clean fractions afforded 48 mg (34%) of ethenesulfonic acid [2-(4-{2-[3-(1-methyl-1H-pyrazol-4-yl)-phenyl]-pyrimidin-5-yl}-pyrazol-1-yl)-ethyl]-amide as a white solid. HPLC: 97% purity. MS (ESI+): 436. $^1$H NMR (400 MHz, DMSO-d6) δ 9.18 (d, 2H), 8.60-8.42 (m, 2H), 8.26 (s, 1H), 8.23 (dd, 1H), 8.18 (s, 1H), 7.92 (s, 1H), 7.72 (dd, 1H), 7.55 (dt, 2H), 6.74-6.61 (m, 1H), 6.11-5.91 (m, 2H), 4.28 (t, 2H), 3.90 (s, 3H), 3.34 (t, 2H).

Example 10: 5-[1-(1-Ethenesulfonyl-piperidin-3-yl)-1H-pyrazol-4-yl]-2-[3-(1-methyl-1H-pyrazol-4-yl)-phenyl]-pyrimidine (17)

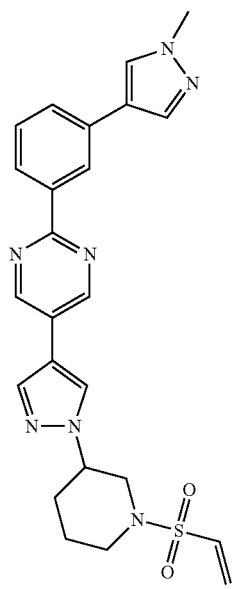 [SMILES: C=CS(=O)(=O)N1CCCC(n2cc(-c3cnc(-c4cccc(-c5cnn(C)c5)c4)nc3)cn2)C1]

In a 20 mL scintillation vial with magnetic stir bar 2-[3-(1-Methyl-1H-pyrazol-4-yl)-phenyl]-5-(1-piperidin-3-yl-1H-pyrazol-4-yl)-pyrimidine trifluoroacetate (144.85 mg; 0.29 mmol; 1.00 eq.) from example 7 was dissolved in DMF (2.00 mL) and DIPEA (202.05 µl; 1.16 mmol; 4.00 eq.). To the stirring homogeneous solution was then added ethenesulfonyl chloride (34.14 µl; 0.35 mmol; 1.20 eq.). The reaction was stirred at room temperature overnight; partially concentrated; and directly purified via prep HPLC. Lyophilization of the combined clean fractions afforded 38 mg (28%) of 5-[1-(1-Ethenesulfonyl-piperidin-3-yl)-1H-pyrazol-4-yl]-2-[3-(1-methyl-1H-pyrazol-4-yl)-phenyl]-pyrimidine as a white solid. HPLC: 100% purity. MS (ESI+): 476. $^1$HNMR (400 MHz, DMSO-d6) δ 9.17 (d, 2H), 8.61-8.50 (m, 2H), 8.30-8.15 (m, 3H), 7.93 (s, 1H), 7.76-7.67 (m, 1H), 7.52 (t, 1H), 6.88 (dd, 1H), 6.24-6.11 (m, 2H), 4.46 (tt, 1H), 3.90 (s, 3H), 3.87-3.78 (m, 1H), 3.54 (d, 1H), 3.00 (t, 1H), 2.81-2.70 (m, 1H), 2.21 (dd, 1H), 2.09-1.89 (m, 2H), 1.80-1.64 (m, 1H).

Example 11: 5-[1-(1-Ethenesulfonyl-piperidin-4-yl)-1H-pyrazol-4-yl]-2-[3-(1-methyl-1H-pyrazol-4-yl)-phenyl]-pyrimidine (18)

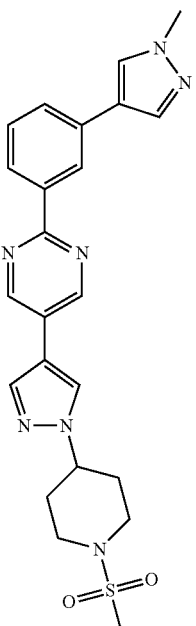

In a 20 mL scintillation vial with magnetic stir bar 2-[3-(1-Methyl-1H-pyrazol-4-yl)-phenyl]-5-(1-piperidin-4-yl-1H-pyrazol-4-yl)-pyrimidine trifluoroacetate (259.73 mg; 0.52 mmol; 1.00 eq.) from example 5 was dissolved in DMF (2.00 mL) and DIPEA (362.30 µl; 2.08 mmol; 4.00 eq.). To the stirring homogeneous solution was then added ethenesulfonyl chloride (61.22 µl; 0.62 mmol; 1.20 eq.). The reaction was stirred at room temperature overnight; partially concentrated; and directly purified via prep HPLC. Lyophilization of the combined clean fractions afforded 50 mg (20%) of 5-[1-(1-Ethenesulfonyl-piperidin-4-yl)-1H-pyrazol-4-yl]-2-[3-(1-methyl-1H-pyrazol-4-yl)-phenyl]-pyrimidine as a white solid. HPLC: 100% purity. MS (ESI+): 476. $^1$HNMR (400 MHz, DMSO-d6) δ 9.17 (s, 2H), 8.55 (d, 2H), 8.30-8.20 (m, 2H), 8.17 (s, 1H), 7.92 (s, 1H), 7.72 (dd, 1H), 7.52 (t, 1H), 6.88 (dd, 1H), 6.25-6.11 (m, 2H), 4.42 (ddd, 1H), 3.90 (s, 3H), 3.73-3.61 (m, 2H), 2.92 (td, 2H), 2.20 (dd, 2H), 2.03 (qd, 2H).

Example 12: 4-(4-{2-[3-(1-Methyl-1H-pyrazol-4-yl)-phenyl]-pyrimidin-5-yl}-pyrazol-1-yl)-piperidine-1-carbonitrile (45)

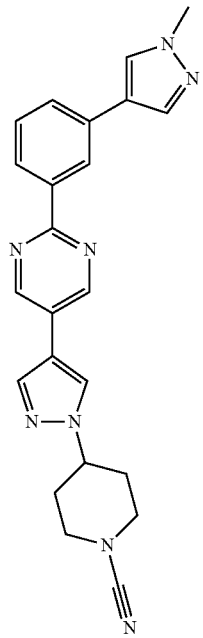 [SMILES: Cn1cc(-c2cccc(-c3ncc(-c4cnn(C5CCN(C#N)CC5)c4)cn3)c2)cn1]

Step 1: 2-[3-(1-Methyl-1H-pyrazol-4-yl)-phenyl]-5-(1-piperidin-4-yl-1H-pyrazol-4-yl)-pyrimidine hydrochloride

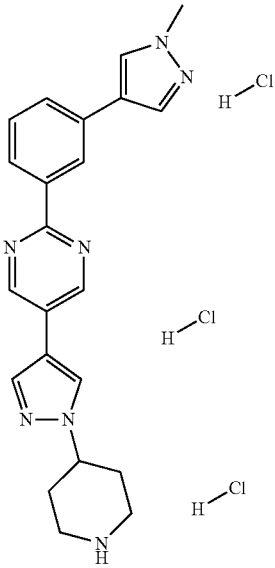

4-(4-{2-[3-(1-Methyl-1H-pyrazol-4-yl)-phenyl]-pyrimidin-5-yl}-pyrazol-1-yl)-piperidine-1-carboxylic acid tert-butyl ester (140.00 mg; 0.29 mmol; 1.00 eq.) from example 3 was suspended in MeOH and treated with 2.0M HCl in diethyl ether (3 mL). The reaction was stirred at room temperature. After 4 hr the reaction was diluted with diethyl ether (7 mL) and filtered. The solids were rinsed with Et2O (2×5 mL) and dried under high vacuum to afford 140 mg (98%) of 2-[3-(1-Methyl-1H-pyrazol-4-yl)-phenyl]-5-(1-piperidin-4-yl-1H-pyrazol-4-yl)-pyrimidine hydrochloride as a yellow solid. MS (ESI+): 386.

Step 2: 4-(4-{2-[3-(1-Methyl-1H-pyrazol-4-yl)-phenyl]-pyrimidin-5-yl}-pyrazol-1-yl)-piperidine-1-carbonitrile (33)

In a 20 mL reaction vial with magnetic stirbar was added 2-[3-(1-Methyl-1H-pyrazol-4-yl)-phenyl]-5-(1-piperidin-4-yl-1H-pyrazol-4-yl)-pyrimidine hydrochloride (3) (68.00 mg; 0.14 mmol; 1.00 eq.), DMF (3.0 mL), and DIPEA (95.74 µl; 0.55 mmol; 4.00 eq.). The cyanogen bromide, 3.0M in DCM (50.39 µl; 0.15 mmol; 1.10 eq.) was then added and the reaction was stirred at room temperature. After 2.5 hr the reaction was partially concentrated and directly purified via prep HPLC. Lyophilization of the combined clean fractions afforded 30 mg (53%) of 4-(4-{2-[3-(1-Methyl-1H-pyrazol-4-yl)-phenyl]-pyrimidin-5-yl}-pyrazol-1-yl)-piperidine-1-carbonitrile as a white solid. HPLC: 100% purity. MS (ESI+): 411. $^1$HNMR (400 MHz, DMSO-d6) δ 9.18 (s, 2H), 8.56 (s, 1H), 8.54 (s, 1H), 8.26 (s, 1H), 8.23 (d, 1H), 8.18 (s, 1H), 7.92 (s, 1H), 7.72 (d, 1H), 7.52 (t, 1H), 4.45 (td, 1H), 3.90 (s, 3H), 3.55 (dt, 2H), 3.26 (dd, 2H), 2.23-1.97 (m, 5H).

Example 13: (Z)-3-Cyclopropyl-2-[4-(4-{2-[3-(1-methyl-1H-pyrazol-4-yl)-phenyl]-pyrimidin-5-yl}-pyrazol-1-yl)-piperidine-1-carbonyl]-acrylonitrile (46)

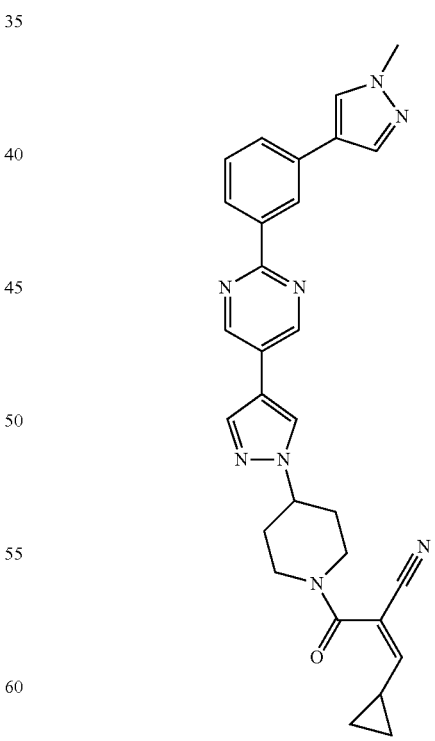

In a 20 mL reaction vial with magnetic stirbar was added 2-[3-(1-Methyl-1H-pyrazol-4-yl)-phenyl]-5-(1-piperidin-4-yl-1H-pyrazol-4-yl)-pyrimidine hydrochloride (3) (68.00 mg; 0.14 mmol; 1.00 eq.) from example 12, DMF (3.0 mL), and DIPEA (95.74 µl; 0.55 mmol; 4.00 eq.). The 2-Cyano-3-cyclopropyl-acrylic acid (20.73 mg; 0.15 mmol; 1.10 eq.) and Pybop (78.66 mg; 0.15 mmol; 1.10 eq.) were then added and the reaction was stirred at room temperature. After 2.5 hr the reaction was partially concentrated and directly purified via prep HPLC. Lyophilization of the combined clean fractions afforded 35 mg (50%) of (Z)-3-Cyclopropyl-2-[4-(4-{2-[3-(1-methyl-1H-pyrazol-4-yl)-phenyl]-pyrimidin-5-yl}-pyrazol-1-yl)-piperidine-1-carbonyl]-acrylonitrile as a white solid. HPLC: 96% purity. MS (ESI+): 505. H NMR (400 MHz, DMSO-d6) δ 9.17 (s, 2H), 8.60-8.49 (m, 2H), 8.26 (s, 1H), 8.23 (d, 1H), 8.17 (s, 1H), 7.92 (s, 1H), 7.72 (d, 1H), 7.52 (t, 1H), 6.67 (d, 1H), 4.58 (tt, 1H), 4.21 (bs, 2H), 3.90 (s, 3H), 3.19 (bs, 3H), 2.26-2.11 (m, 2H), 1.94 (dtt, 3H), 1.21 (dq, 2H), 0.95 (p, 2H).

Example 14: 1-Hydroxymethyl-3-(4-{2-[3-(1-methyl-1H-pyrazol-4-yl)-phenyl]-pyrimidin-5-yl}-pyrazol-1-yl)-cyclohexanol (1)

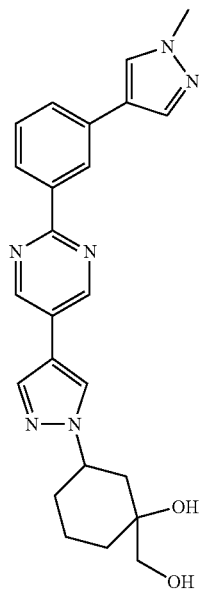 [SMILES: Cn1cc(-c2cccc(-c3ncc(-c4cnn(C5CCCC(O)(CO)C5)c4)cn3)c2)cn1]

Step 1: 3-(4-Bromo-pyrazol-1-yl)-cyclohexanone

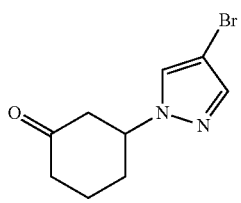 [SMILES: O=C1CCCC(n2cc(Br)cn2)C1]

Bismuth(III) trifluoromethanesulfonate (5.25 g; 7.92 mmol; 0.15 eq.) was added to a mixture of 4-Bromo-1H-pyrazole (8.00 g; 52.8 mmol; 1.0 eq.) and Cyclohex-2-enone (6.34 g; 63.3 mmol; 1.2 eq.) in DCM (80 mL) and the reaction mixture was stirred at RT for 30 h. It was filtered to remove bismuth trifluoromethanesulfonate. The filtrate was washed with saturated NaHCO$_3$ (2×150 mL) and brine solution (1×150 mL), dried over Na$_2$SO$_4$, filtrated and concentrated. The Crude was purified by flash chromatography on silica (Pet. Ether: EtOAc, 8:2) to give the title compound as a brown gum (8.5 g; 55.8%). 1H NMR (400 MH, CDCl3) δ: 8.02 (s, 1H), 7.55 (s, 1H), 4.69-4.65 (m, 1H), 2.88-2.84 (m, 1H), 2.82-2.64 (m, 1H), 2.37-2.33 (m, 1H), 2.30-2.27 (m, 1H), 2.10-2.03 (m, 2H), 1.86-1.83 (m, 1H), 1.68-1.66 (m, 1H).

Step 2: 2-[3-(1-Methyl-1H-pyrazol-4-yl)-phenyl]-5-(4,4,5,5-tetramethyl-[1,3,2]dioxaborolan-2-yl)-pyrimidine

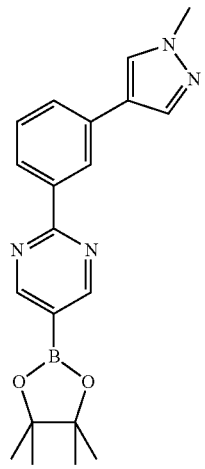 [SMILES: Cn1cc(-c2cccc(-c3ncc(B4OC(C)(C)C(C)(C)O4)cn3)c2)cn1]

A mixture of 5-bromo-2-[3-(1-methyl-1H-pyrazol-4-yl)phenyl]pyrimidine (700 mg; 2.22 mmol; 1.0 eq.), bis(pinacolato)diboron (508 mg; 2.00 mmol; 0.9 eq.), potassium acetate (436 mg; 4.44 mmol; 2.0 eq.) and (dppf)PdCl$_2$.CH$_2$Cl$_2$ (162 mg; 0.22 mmol; 0.10 eq.) in Dioxane (4 mL) was heated at 100° C. for 1 h in the MW. Reaction mixture was diluted with a saturated solution of NaHCO$_3$ and extracted with EtOAc (three times). Combined organic phases were washed with brine, dried over magnesium sulfate, filtered and concentrated to give the title compound as a dark oil (1 g, 89%) which was used in the next steps without further purification. $^1$H NMR (300 MHz, DMSO) δ 9.03 (s, 2H), 8.56 (s, 1H), 8.34-8.18 (m, 2H), 7.92 (s, 1H), 7.76 (d, J=7.6 Hz, 1H), 7.53 (t, J=7.7 Hz, 1H), 3.89 (s, 3H), 1.35 (s, 12H).

Step 3: 3-(4-{2-[3-(1-Methyl-1H-pyrazol-4-yl)-phenyl]-pyrimidin-5-yl}-pyrazol-1-yl)-cyclohexanone

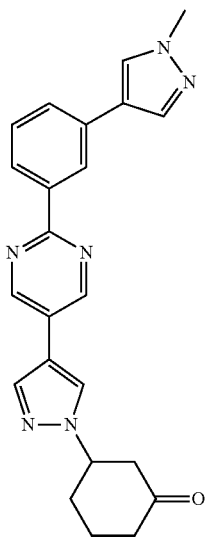 [SMILES: Cn1cc(-c2cccc(-c3ncc(-c4cnn(C5CCCC(=O)C5)c4)cn3)c2)cn1]

A solution of 3-(4-Bromo-pyrazol-1-yl)-cyclohexanone (900 mg; 3.12 mmol; 1.0 eq.), potassium carbonate (888 mg; 6.23 mmol; 2.0 eq.) and 2-[3-(1-Methyl-1H-pyrazol-4-yl)-phenyl]-5-(4,4,5,5-tetramethyl-[1,3,2]dioxaborolan-2-yl)-pyrimidine (1.3 g; 3.43 mmol; 1.1 eq.) in Dioxane-1,4 (36 mL) and Water (9 mL) was degassed for 15 min. 1,1'-Bis(diphenylphosphino)ferrocene]dichloropalladium(II).CH$_2$Cl$_2$ (131 mg; 0.16 mmol; 0.05 eq.) was then added and the reaction mixture was heated to 100° C. for 90 min. Dioxane was removed under reduced pressure, the residual suspension was diluted with water (100 mL) and extracted with ethylacetate (2×150 mL). Combined organic layers were dried over anhydrous Na$_2$SO$_4$, filtered and concentrated. Purification of the crude by flash chromatography on silica (DCM:MeOH, 9:1) afforded the title compound as a brown solid (590 mg; 44.2%). LC/MS: (max plot) 93%; (254 nm) 95%; Rt 3.75 min; 399.2 (M+1).

Step 4: 2-[3-(1-Methyl-1H-pyrazol-4-yl)-phenyl]-5-[1-(1-oxa-spiro[2.5]oct-5-yl)-1H-pyrazol-4-yl]-pyrimidine

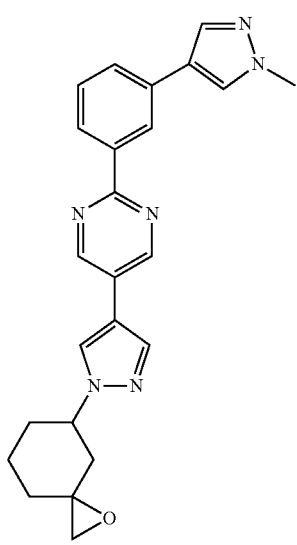 [SMILES: Cn1cc(-c2cccc(-c3ncc(-c4cnn(C5CCCC6(CO6)C5)c4)cn3)c2)cn1]

2-Methyl-propan-2-ol potassium (186 mg; 1.61 mmol; 1.2 eq.) was added at RT in one portion to a solution of 3-(4-{2-[3-(1-Methyl-1H-pyrazol-4-yl)-phenyl]-pyrimidin-5-yl}-pyrazol-1-yl)-cyclohexanone (580 mg; 1.35 mmol; 1.0 eq.) and Trimethylsulfoxonium iodide (359 mg; 1.60 mmol; 1.2 eq.) in DMSO (12 mL). The reaction mixture was stirred at RT for 15 h. It was then poured into ice water (100 mL), extracted with ethylacetate (2×150 mL), washed with brine solution (75 mL), dried over anhydrous sodium sulphate, filtrated and concentrated. Purification by flash chromatography on silica (DCM/MeOH, 9:1) afforded the title compound as an off white solid (450 mg; 0.64 mmol; 48%). LC/MS: Rt 3.97 min; 413.3 (M+1).

Step 5: 1-Hydroxymethyl-3-(4-{2-[3-(1-methyl-1H-pyrazol-4-yl)-phenyl]-pyrimidin-5-yl}-pyrazol-1-yl)-cyclohexanol A solution of 2-[3-(1-Methyl-1H-pyrazol-4-yl)-phenyl]-5-[1-(1-oxa-spiro[2.5]oct-5-yl)-1H-pyrazol-4-yl]-pyrimidine (150 mg; 0.21 mmol; 1.0 eq.) and NaHCO$_3$ (58 mg; 0.67 mmol; 3.1 eq.) in 1-Methyl-pyrrolidin-2-one (3 mL) and Water (1.5 mL) was heated at 130° C. for 14 h. The reaction mixture was then cooled to RT, diluted with water (50 mL) and extracted with DCM (2×75 mL). Combined organic layers were washed with brine solution (50 mL), dried over anhydrous Na$_2$SO$_4$, filtered and concentrated. Purification by preparative HPLC afforded the title compound as a white solid (20 mg, 21%). 1H NMR (400 MHz, DMSO) 9.15 (s, 2H), 8.52-8.51 (m, 1H), 8.50 (s, 1H), 8.25 (s, 1H), 8.20 (d, J=7.8 Hz, 1H), 8.10 (s, 1H), 7.91 (s, 1H), 7.69 (d, J=7.9 Hz, 1H), 7.50 (t, J=7.8 Hz, 1H), 4.68 (t, J=5.8 Hz, 1H), 4.54-4.48 (m, 1H), 4.28 (s, 1H), 3.88 (s, 3H), 3.21 (d, J=5.80 Hz, 2H), 2.03-2.01 (m, 1H), 1.87-1.85 (m, 2H), 1.80-1.74 (m, 1H), 1.68-1.63 (m, 2H), 1.44-1.40 (m, 2H). HPLC: (max plot) 98%; (254 nm) 98%; Rt 3.23 min. LC/MS: 431.0 (M+1).

Example 15: 2-[Trans-3-(4-{2-[3-(1-Methyl-1H-pyrazol-4-yl)-phenyl]-pyrimidin-5-yl}-pyrazol-1-yl)-cyclohexylamino]-ethanol (2)

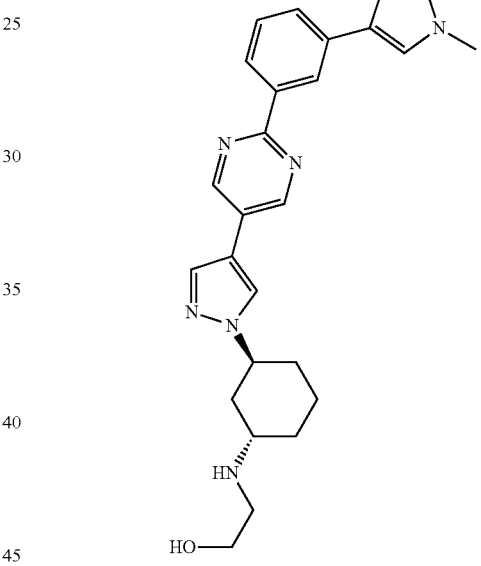

Step 1: 2-[Trans-3-(4-Bromo-pyrazol-1-yl)-cyclohexylamino]-ethanol

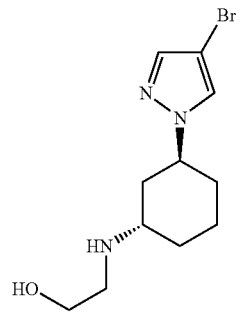

2-Amino-ethanol (0.46 g; 7.48 mmol; 1.44 eq.) was added in one portion to a solution of 3-(4-Bromo-pyrazol-1-yl)- cyclohexanone (1.50 g; 5.2 mmol; 1.0 eq.) in Ethanol (30 mL). After one hour the reaction mixture was cooled to 0° C. and sodium borohydride (0.45 g; 11.53 mmol; 2.22 eq.) was added portion wise over five minutes. The reaction mixture was stirred at RT for 2 more hrs before being poured into 1 N NaOH solution (200 mL). The mixture was extracted with DCM (2×250 mL), dried over anhydrous Na$_2$SO$_4$, filtered and concentrated to afford 2-[3-(4-Bromo-pyrazol-1-yl)-cyclohexylamino]-ethanol (1.4 g; 4.70 mmol; 90.5%) as 8:2 mixture of the cis and trans isomers. The two isomers were separated by preparative HPLC (XBridge C8(150×4.6) mm, 3.5 μm, Mobile Phase: A: 10 mM NH4HCO3 in H2O, B: ACN; Flow Rate: 0.8 mL/min). First eluting fraction (assigned as the trans isomer): 550 mg. 1H NMR (400 MHz, CDCl3) δ 7.47 (d, J=6.8 Hz, 2H), 4.20-4.12 (m, 1H), 3.86-3.83 (m, 2H), 3.08-3.03 (m, 3H), 2.56-2.53 (m, 1H), 2.16-2.05 (m, 2H), 2.04-2.02 (m, 1H), 1.89 (q, J=11.9 Hz, 1H), 1.76-1.66 (m, 1H), 1.49-1.43 (m, 2H). HPLC: (max plot) 98%; (220 nm) 97%; Rt 7.37 min. Second eluting fraction: 150 mg of a mixture of cis and trans isomers which was not further purified.

Step 2: 2-[Trans-3-(4-{2-[3-(1-Methyl-1H-pyrazol-4-yl)-phenyl]-pyrimidin-5-yl}-pyrazol-1-yl)-cyclohexylamino]-ethanol The title compound was obtained following procedure described for example 14, step 3, but starting from 2-[Trans-3-(4-Bromo-pyrazol-1-yl)-cyclohexylamino]-ethanol (120 mg; 0.41 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (168 mg; 0.45 mmol; 1.1 eq.) as a brown solid (75 mg, 41%). 1H NMR (400 MHz, DMSO) δ 9.15 (s, 2H), 8.52-8.51 (m, 1H), 8.50 (s, 1H), 8.25 (s, 1H), 8.20 (d, J=9.1 Hz, 1H), 8.11 (s, 1H), 7.91 (s, 1H), 7.70 (d, J=7.9 Hz, 1H), 7.50 (t, J=7.8 Hz, 1H), 4.48-4.47 (m, 1H), 4.25-4.21 (m, 1H), 3.88 (s, 3H), 3.45-3.41 (m, 2H), 2.66-2.56 (m, 3H), 2.32-2.28 (m, 1H), 2.06-2.03 (m, 1H), 1.92-1.89 (m, 1H), 1.84-1.81 (m, 1H), 1.66-1.62 (m, 1H), 1.54-1.40 (m, 2H), 1.03-1.00 (m, 1H). HPLC: (max plot) 100%; (254 nm) 100%; Rt 2.96 min. LC/MS: 444.2 (M+1).

Example 16: 4-[Trans-3-(4-{2-[3-(1-Methyl-1H-pyrazol-4-yl)-phenyl]-pyrimidin-5-yl}-pyrazol-1-yl)-cyclohexyl]-morpholin-3-one (3)

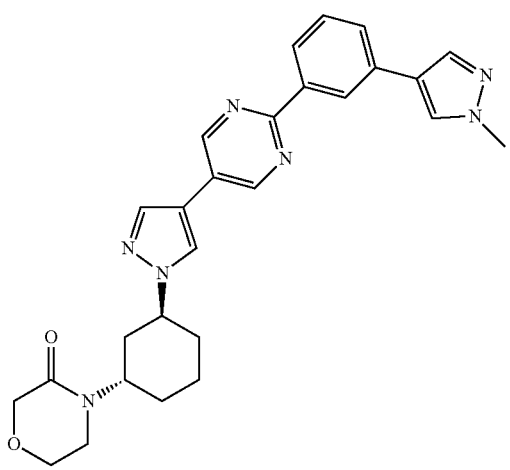 [SMILES: Cn1cc(-c2cccc(-c3ncc(-c4cnn([C@H]5CCC[C@H](N6CCOCC6=O)C5)c4)cn3)c2)cn1]

Step 1: 4-[(trans)-3-(4-Bromo-pyrazol-1-yl)-cyclohexyl]-morpholin-3-one

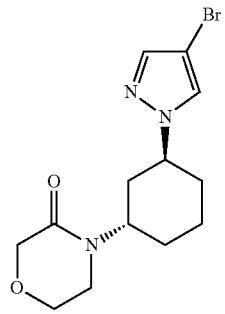 [SMILES: O=C1COCCN1[C@H]1CCC[C@H](n2cc(Br)cn2)C1]

Chloro-acetyl chloride (150 mg; 1.30 mmol; 1.10 eq.) was added dropwise over two min to a solution of 2-[Trans-3-(4-Bromo-pyrazol-1-yl)-cyclohexylamino]-ethanol (350 mg; 1.18 mmol; 1.0 eq.) in Ethyl-diisopropyl-amine (0.83 mL; 4.74 mmol; 4.0 eq.) and THF (10.5 mL) maintained at −30° C. The reaction solution was allowed to warm slowly to RT and stirred for 16 h. Then it was poured into a 1.5 N HCl solution (25 mL) and extracted with DCM (2×50 mL). Combined organic phases were washed with NaHCO$_3$ (saturated solution), dried over sodium sulfate, filtered and concentrated to give a brown residue which was redissolved in THF (10.5 mL). 2-Methyl-propan-2-ol sodium (2M Solution in THF) (2.50 mL; 24 mmol; 20 eq.) was added in one portion and the reaction solution was heated at 40° C. for 1 h. It was then cooled to RT, poured into 1.5N HCl solution (40 mL) and extracted with DCM (2×75 mL). Combined organic layers were dried over anhydrous Na$_2$SO$_4$, filtered and concentrated to afford the title compound as a dark brown oil (360 mg, 46%). LC/MS: 328.0 (M+1).

Step 2: 4-[Trans-3-(4-{2-[3-(1-Methyl-1H-pyrazol-4-yl)-phenyl]-pyrimidin-5-yl}-pyrazol-1-yl)-cyclohexyl]-morpholin-3-one The title compound was obtained following procedure described for example 14, step 3, but starting from 4-[Trans-3-(4-Bromo-pyrazol-1-yl)-cyclohexyl]-morpholin-3-one (300 mg; 0.45 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (186 mg; 0.49 mmol; 1.1 eq.) as a yellow solid (28 mg, 12%). 1H NMR (400 MHz, DMSO) δ 9.15 (s, 2H), 8.51 (s, 2H), 8.25 (s, 1H), 8.20 (d, J=7.8 Hz, 1H), 8.13 (s, 1H), 7.91 (s, 1H), 7.70 (d, J=7.7 Hz, 1H), 7.50 (t, J=7.8 Hz, 1H), 4.47-4.35 (m, 2H), 4.03 (s, 2H), 3.88 (s, 3H), 3.82-3.79 (m, 2H), 3.32-3.30 (m, 2H), 2.08-1.99 (m, 3H), 1.93-1.91 (m, 1H), 1.72-1.69 (m, 1H), 1.66-1.54 (m, 3H). HPLC: (max plot) 96%; (254 nm) 94%; Rt 3.57 min. LC/MS: 484.2 (M+1).

Example 17: 4-[Cis-3-(4-{2-[3-(1-Methyl-1H-pyrazol-4-yl)-phenyl]-pyrimidin-5-yl}-pyrazol-1-yl)-cyclohexyl]-morpholine (4)

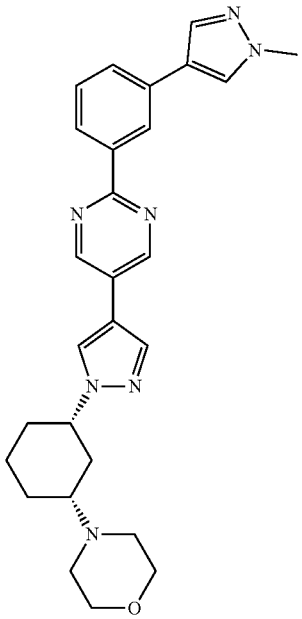 [SMILES: Cn1cc(-c2cccc(-c3ncc(-c4cnn([C@H]5CCC[C@@H](N6CCOCC6)C5)c4)cn3)c2)cn1]

Step 1: 4-[(Cis)-3-(4-Bromo-pyrazol-1-yl)-cyclohexyl]-morpholine and 4-[(trans)-3-(4-Bromo-pyrazol-1-yl)-cyclohexyl]-morpholine

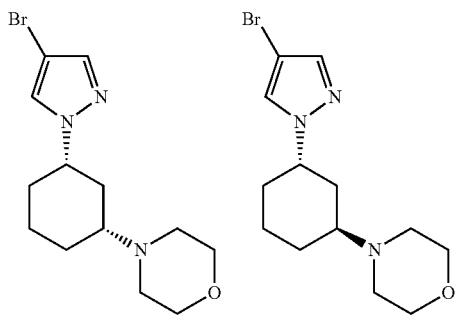

A solution of 3-(4-Bromo-pyrazol-1-yl)-cyclohexanone (1.50 g; 5.20 mmol; 1.0 eq.), Morpholine (0.55 mL; 6.23 mmol; 1.2 eq.) and acetic acid (1.50 mL) in DMF (7.50 mL) and THF (7.50 mL) was stirred overnight at RT. The reaction mixture was cooled to 0° C. before the addition of Sodium cyanoborohydride (0.52 g; 7.79 mmol; 1.50 eq.) and stirred at RT for 4 h. Solvents were removed under reduced pressure and water (100 mL) was added to the residue. The mixture was extracted with DCM (2×150 mL), the combined organic phases were then dried over anhydrous $Na_2SO_4$, filtered and concentrated to give the title compound as a (4:6) mixture of cis and trans isomers (650 mg, 37%). The two isomers were separated by Preparative HPLC (Column: XBridge C8 (150×4.6) mm, 3.5 µm, Mobile Phase: A: 10 mM $NH_4HCO_3$ in H2O, B: ACN; Flow Rate: 0.8 mL/min). First eluting fraction: 80 mg, Brown gum. Attributed as the Cis isomer based on NOE experiment by irradiation of 4, 12 proton. 1H NMR (400 MHz, CDCl3) δ: 7.44 (d, J=5.1 Hz, 2H), 4.14-4.10 (m, 1H), 3.80-3.78 (m, 4H), 2.77-2.67 (m, 5H), 2.42-2.39 (m, 1H), 2.13-2.10 (m, 1H), 2.04-2.00 (m, 2H), 1.80-1.64 (m, 2H), 1.44-1.34 (m, 2H). LC/MS: (max plot) 99%; (220 nm) 98%; Rt 4.66 min; 316 (M+1). Second eluting fraction: 120 mg, brown gum. Attributed as the Trans isomer based on NOE experiment by irradiation of 4.51 proton. 1H NMR (400 MHz, CDCl3) δ: 7.44 (s, 2H), 4.53-4.49 (m, 1H), 3.74-3.72 (m, 4H), 2.51-2.48 (m, 5H), 2.26-2.25 (m, 1H), 2.23-2.22 (m, 1H), 2.22-1.76 (m, 4H), 1.61-1.56 (m, 1H), 1.52-1.48 (m, 1H). LC/MS: (max plot) 99%; (220 nm) 98%; Rt 5.23 min; 316 (M+1).

Step 2: 4-[Cis-3-(4-{2-[3-(1-Methyl-1H-pyrazol-4-yl)-phenyl]-pyrimidin-5-yl}-pyrazol-1-yl)-cyclohexyl]-morpholine The title compound was obtained following procedure described for example 14, step 3, but starting from 2-[3-(1-Methyl-1H-pyrazol-4-yl)-phenyl]-5-(4,4,5,5-tetramethyl-[1,3,2]dioxaborolan-2-yl)-pyrimidine (95 mg; 0.25 mmol; 1.0 eq) and 4-[(cis)-3-(4-Bromo-pyrazol-1-yl)-cyclohexyl]-morpholine as a beige solid (30 mg, 25%). 1H NMR (400 MHz, DMSO) δ: 9.15 (s, 2H), 8.52 (s, 2H), 8.25 (s, 1H), 8.22-8.21 (m, 1H), 8.21 (s, 1H), 7.91-7.91 (m, 1H), 7.71-7.69 (m, 1H), 7.52-7.48 (m, 1H), 4.28-4.22 (m, 1H), 3.88 (s, 3H), 3.56 (t, J=4.36 Hz, 4H), 2.50-2.48 (m, 4H), 2.32-2.31 (m, 1H), 2.07-2.04 (m, 1H), 1.90-1.86 (m, 2H), 1.74-1.60 (m, 2H), 1.42-1.39 (m, 1H), 1.35-1.27 (m, 1H). HPLC: (max plot) 98%; (254 nm) 97%; Rt 3.07 min. LC/MS: 470.2 (M+1).

Example 18: 4-[Trans-3-(4-{2-[3-(1-Methyl-1H-pyrazol-4-yl)-phenyl]-pyrimidin-5-yl}-pyrazol-1-yl)-cyclohexyl]-morpholine (5)

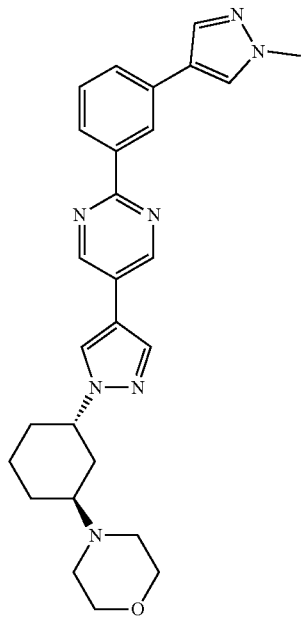 [SMILES: Cn1cc(-c2cccc(-c3ncc(-c4cnn([C@H]5CCC[C@H](N6CCOCC6)C5)c4)cn3)c2)cn1]

The title compound was obtained following the procedure described for example 14, step 3, but starting from 4-[(trans)-3-(4-Bromo-pyrazol-1-yl)-cyclohexyl]-morpholine (110 mg; 0.35 mmol; 1.0 eq.) and 2-[3-(1-Methyl-1H-pyrazol-4-yl)-phenyl]-5-(4,4,5,5-tetramethyl-[1,3,2]dioxaborolan-2-yl)-pyrimidine (144 mg; 0.38 mmol; 1.1 eq.) as a brown gum (10 mg, 5%). 1H NMR (400 MHz, MeOD) δ 9.09 (s, 2H), 8.59-8.58 (m, 1H), 8.37 (s, 1H), 8.26 (d, J=7.9 Hz, 1H), 8.06-8.05 (m, 2H), 7.91 (s, 1H), 7.70-7.68 (m, 1H), 7.52-7.48 (m, 1H), 4.61 (s, 2H), 3.97 (s, 3H), 3.77-3.76 (m, 4H), 2.34-2.30 (m, 2H), 2.11-2.10 (m, 3H), 2.06-1.92 (m, 1H), 1.66-1.61 (m, 3H). HPLC: (max plot) 86%; (254 nm) 87%; Rt 3.1 min. LC/MS: 470.2 (M+1).

Example 19: 5-{1-[3-(4,4-Difluoro-piperidin-1-yl)-cyclohexyl]-1H-pyrazol-4-yl}-2-[3-(1-methyl-1H-pyrazol-4-yl)-phenyl]-pyrimidine (11)

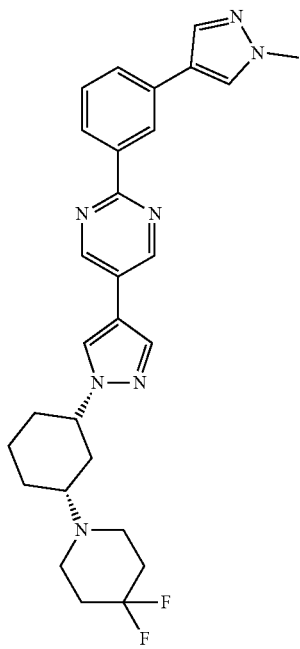

Step 1: 1-[3-(4-Bromo-pyrazol-1-yl)-cyclohexyl]-4,4-difluoro-piperidine

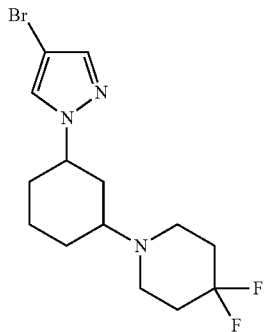 [SMILES: FC1(F)CCN(C2CCCC(n3cc(Br)cn3)C2)CC1]

A solution of 3-(4-Bromo-pyrazol-1-yl)-cyclohexanone (1.00 g; 3.45 mmol; 1.00 eq.), 4,4-Difluoro-piperidine.hydrochloride (0.83 g; 5.18 mmol; 1.50 eq.) and Ethyl-diisopropyl-amine (1.21 mL; 6.90 mmol; 2.00 eq.) in DCE (10 mL) was stirred at 50° C. for 30 min. Then Sodium triacetoxyborohydride (1.16 g; 5.18 mmol; 1.50 eq.) was added and the reaction mixture was stirred for 15 h at 50° C. The reaction mixture was then allowed to cool to RT, diluted with DCM (50 mL) and poured into a saturated solution of NaHCO$_3$. The organic layer was separated and washed with brine. The aqueous layers were back extracted with DCM and the combined organic layers were dried over anhydrous Na$_2$SO$_4$, filtered and concentrated to give the title product as a brown gum (2 g; 83%; mixture of isomers, 7:3).

Step 2: 5-{Cis-1-[3-(4,4-Difluoro-piperidin-1-yl)-cyclohexyl]-1H-pyrazol-4-yl}-2-[3-(1-methyl-1H-pyrazol-4-yl)-phenyl]-pyrimidine The title compound was obtained following procedure described for example 14, step 3, but starting from 1-[3-(4-Bromo-pyrazol-1-yl)-cyclohexyl]-4,4-difluoro-piperidine (250 mg; 0.48 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (201 mg; 0.53 mmol; 1.10 eq.) as an off-white solid (50 mg, 20%). Correspond to the major isomer which was assigned as the cis. 1H NMR (400 MHz, DMSO) δ: 9.15 (s, 2H), 8.52 (s, 2H), 8.25 (s, 1H), 8.21 (d, J=8.0 Hz, 1H), 8.12 (s, 1H), 7.91 (s, 1H), 7.70 (d, J=8.1 Hz, 1H), 7.50 (t, J=7.8 Hz, 1H), 4.28-4.23 (m, 1H), 3.89 (s, 3H), 2.69-2.64 (m, 5H), 2.19-2.16 (m, 1H), 2.08-2.04 (m, 1H), 1.96-1.86 (m, 5H), 1.80-1.72 (m, 2H), 1.64-1.60 (m, 1H), 1.43-1.40 (m, 1H), 1.33-1.25 (m, 1H). HPLC: (max plot) 97%; (254 nm) 92%; Rt 3.35 min. LC/MS: 504.2 (M+1).

Example 20: [3-Cis-(4-{2-[3-(1-Methyl-1H-pyrazol-4-yl)-phenyl]-pyrimidin-5-yl}-pyrazol-1-yl)-cyclohexyl]-(tetrahydro-furan-3-yl)-amine (12)

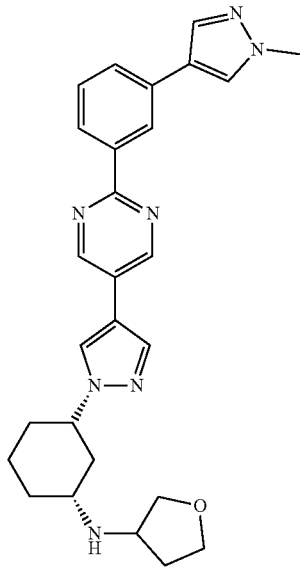

Step 1: [3-(4-Bromo-pyrazol-1-yl)-cyclohexyl]-(tetrahydro-furan-3-yl)-amine

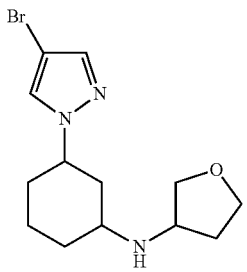 [SMILES: Brc1cnn(C2CCCC(NC3CCOC3)C2)c1]

The title compound was obtained following procedure described for example 19, step 1, but starting from 3-(4-Bromo-pyrazol-1-yl)-cyclohexanone (1.00 g; 3.45 mmol; 1.00 eq.) and tetrahydro-furan-3-ylamine (0.47 g; 5.18 mmol; 1.50 eq.) as a brown gum (1.2 g, 76%, 1:1 mixture of cis and trans isomer). LC/MS: 316 (M+1).

Step 2: [3-Cis-(4-{2-[3-(1-Methyl-1H-pyrazol-4-yl)-phenyl]-pyrimidin-5-yl}-pyrazol-1-yl)-cyclohexyl]-(tetrahydro-furan-3-yl)-amine The title compound was obtained following procedure described for example 14, step 3, but starting from [3-(4-Bromo-pyrazol-1-yl)-cyclohexyl]-(tetrahydro-furan-3-yl)-amine (250 mg; 0.55 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (230 mg; 0.60 mmol; 1.10 eq.) as a brown solid (38 mg, 14%). Correspond to the major isomer which was assigned as the cis. 1H NMR (400 MHz, DMSO) δ: 9.15 (s, 2H), 8.51 (d, J=9.8 Hz, 2H), 8.26 (s, 1H), 8.21 (d, J=7.8 Hz, 1H), 8.12 (s, 1H), 7.91 (s, 1H), 7.70 (d, J=7.8 Hz, 1H), 7.50 (t, J=7.8 Hz, 1H), 4.24-4.21 (m, 1H), 3.88 (s, 3H), 3.77-3.71 (m, 2H), 3.65-3.60 (m, 1H), 3.51-3.46 (m, 1H), 2.50-2.49 (m, 2H), 2.36-2.32 (m, 1H), 2.06-2.00 (m, 1H), 1.99-1.94 (m, 2H), 1.90-1.81 (m, 1H), 1.66-1.60 (m, 2H), 1.52-1.41 (m, 2H), 1.04-1.01 (m, 1H). HPLC: (max plot) 97%; (254 nm) 96%; Rt 3.06 min. LC/MS: 470.2 (M+1).

Example 21: 2-Fluoro-3-(4-{2-[3-(1-methyl-1H-pyrazol-4-yl)-phenyl]-pyrimidin-5-yl}-pyrazol-1-yl)-8-aza-bicyclo[3.2.1]octane (19)

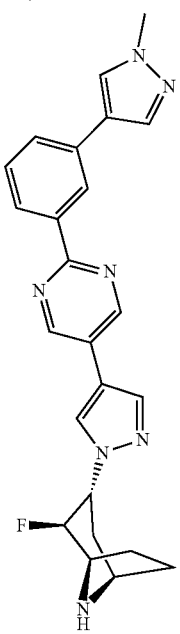 [SMILES: Cn1cc(-c2cccc(-c3ncc(-c4cnn([C@@H]5C[C@H]6CC[C@@H](N6)[C@H]5F)c4)cn3)c2)cn1]

Step 1: 3-Triethylsilanyloxy-8-aza-bicyclo[3.2.1]oct-2-ene-8-carboxylic acid tert-butyl ester

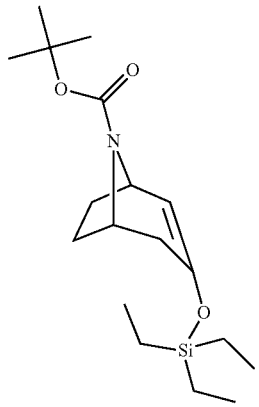 [SMILES: CC[Si](CC)(CC)OC1=CC2CCC(C1)N2C(=O)OC(C)(C)C]

To a solution of Diisopropyl-amine (2.18 m; 15.45 mmol; 1.20 eq.) in THF (70.00 mL) at −78° C. was added Butyl Lithium (9.65 mL of a 1.6 M solution in hexanes; 15.45 mmol; 1.20 eq.). The solution was warmed to 0° C., stirred for 20 min and cooled again at −78° C. 3-Oxo-8-aza-bicyclo[3.2.1]octane-8-carboxylic acid tert-butyl ester (2.9 g; 12.9 mmol; 1.00 eq.) in THF (70 mL) was added dropwise. After 30 min, the solution was warmed at −20° C. and a saturated solution of NaHCO$_3$ (25 mL) was added. The mixture was extracted with petrol ether (3×75 mL). Combined organic layers were dried over MgSO$_4$, filtered and concentrated. Purification by flash chromatography on silica (n-heptane:EtOAc, 85:15) afforded the title compound as a pale yellow oil (4.17 g, 95%). 1H NMR (400 MHz, CDCl3) δ 5.16 (t, J=6.6 Hz, 1H), 4.39-4.19 (m, 2H), 2.88-2.63 (m, 1H), 2.23-2.04 (m, 1H), 1.99-1.57 (m, 3H), 1.45 (s, 9H), 1.31-1.22 (m, 1H), 1.00-0.85 (m, 9H), 0.69-0.58 (m, 6H).

Step 2: 2-Fluoro-3-oxo-8-aza-bicyclo[3.2.1]octane-8-carboxylic acid tert-butyl ester

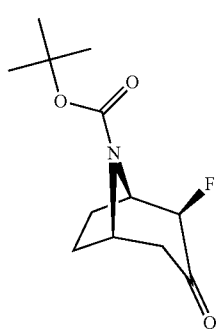 [SMILES: CC(C)(C)OC(=O)N1[C@@H]2CC[C@@H]1[C@@H](F)C(=O)C2]

Select Fluor (8.7 g, 24.5 mmol, 2 eq.) was added in one portion to a solution of 3-Triethylsilanyloxy-8-aza-bicyclo[3.2.1]oct-2-ene-8-carboxylic acid tert-butyl ester (4.17 g, 12.28 mol, 1.00 eq.) in dry CH$_3$CN (80 mL) under nitrogen. The reaction mixture was stirred at RT for 1 h. It was then poured into EtOAc (250 mL) and washed with water (3×50 mL). The organic phase was dried over MgSO$_4$, filtered and evaporated to give the title compound (2.7 g, 90%). 1H NMR (400 MHz, CDCl3) δ 4.94-4.24 (m, 3H), 3.17-2.89 (m, 1H), 2.35 (ddq, J=15.1, 2.0, 1.0 Hz, 1H), 2.21-1.92 (m, 2H), 1.70-1.36 (m, 11H).

Step 3: 3-(N'-tert-Butoxycarbonyl-hydrazino)-2-fluoro-8-aza-bicyclo[3.2.1]octane-8-carboxylic acid tert-butyl ester

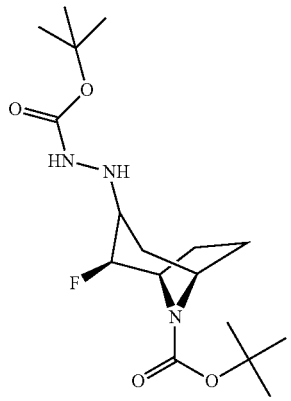 [SMILES: CC(C)(C)OC(=O)NNC1C[C@H]2CC[C@H]([C@H]1F)N2C(=O)OC(C)(C)C]

Hydrazinecarboxylic acid tert-butyl ester (1.20 g; 8.86 mmol; 1.10 eq.) was added to a solution of 2-Fluoro-3-oxo-8-aza-bicyclo[3.2.1]octane-8-carboxylic acid tert-butyl ester (2.0 g; 8.06 mmol; 1.00 eq.) in acetic acid. The reaction mixture was stirred at RT for 15 min, then cooled to 0° C. before the addition of sodium cyanoborohydride (0.53 g; 8.06 mmol; 1.00 eq.). It was stirred at RT for 15 h and basified with 5N NaOH (pH adjusted to 9) while maintaining the internal temperature below 20° C. by adding crushed ice. Reaction mixture was finally extracted with DCM (2×100 mL). Combined organic layers were dried over anhydrous Na$_2$SO$_4$, filtrated and concentrated to give the title compound as a white solid (2.30 g; 76.0%). LC/MS: (max plot) 96%; (ELSD, 23+73 (mixture of isomers); Rt 4.07-4.88 min; 260 (M=1−tBu).

Step 4: 3-(4-Bromo-pyrazol-1-yl)-2-fluoro-8-aza-bicyclo[3.2.1]octane

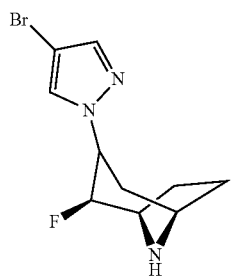 [SMILES: F[C@H]1C(n2cc(Br)cn2)C[C@H]2CC[C@H]1N2]

Hydrobromic acid in water (1.38 mL; 12.25 mmol; 2.00 eq.) was added to a solution of 3-(N'-tert-Butoxycarbonyl-hydrazino)-2-fluoro-8-aza-bicyclo[3.2.1]octane-8-carboxylic acid tert-butyl ester (2.30 g; 6.13 mmol; 1.00 eq.) and 2-Bromo-malonaldehyde (1.05 g; 6.74 mmol; 1.10 eq.) in Acetic acid (4.60 mL; 2.00 V) maintained at 0° C. The reaction mixture was then stirred at RT for 6 h. It was cooled by adding crushed ice and basified to pH 13 by addition of a 5N NaOH solution. The aqueous layer was extracted with DCM (2×100 mL) and the combined organic layers were dried over anhydrous Na$_2$SO$_4$, filtered and concentrated to give the title compound as a brown solid (1.50 g; 32.3%). LC/MS: 276.0 (M=1).

Step 5: 2-Fluoro-3-(4-{2-[3-(1-methyl-1H-pyrazol-4-yl)-phenyl]-pyrimidin-5-yl}-pyrazol-1-yl)-8-aza-bicyclo[3.2.1]octane The title compound was obtained following the procedure described for example 14, step 3, but starting from 3-(4-Bromo-pyrazol-1-yl)-2-fluoro-8-aza-bicyclo[3.2.1]octane (500 mg; 0.66 mmol; 1.00 eq) and 2-[3-(1-Methyl-1H-pyrazol-4-yl)-phenyl]-5-(4,4,5,5-tetramethyl-[1,3,2]dioxaborolan-2-yl)-pyrimidine (278 mg; 0.73 mmol; 1.10 eq.) as a brown solid (90 mg, 32%). 1H NMR (DMSO; 1H) δ 9.16 (t, J=4.9 Hz, 2H), 8.59-8.49 (m, 2H), 8.26 (s, 1H), 8.22-8.15 (m, 2H), 7.91 (s, 1H), 7.70 (d, J=7.7 Hz, 1H), 7.51 (t, J=7.8 Hz, 1H), 4.81-4.68 (m, 2H), 3.88 (s, 3H), 3.64-3.56 (m, 2H), 2.50-2.49 (m, 1H), 1.99-1.94 (m, 1H), 1.78-1.69 (m, 3H), 1.55-1.53 (m, 1H). HPLC: (max plot) 100%; (74:22; mixture of isomers); Rt 2.86; 3.16 min. LC/MS: 430.0 (M+1).

Example 22: 2-Fluoro-8-methyl-3-(4-{2-[3-(1-methyl-1H-pyrazol-4-yl)-phenyl]-pyrimidin-5-yl}-pyrazol-1-yl)-8-aza-bicyclo[3.2.1]octane (20)

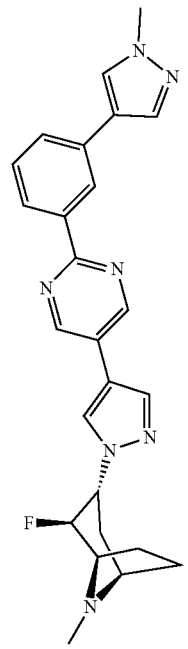 [SMILES: CN1[C@@H]2CC[C@@H]1[C@@H](F)[C@H](n1cc(-c3cnc(-c4cccc(-c5cnn(C)c5)c4)nc3)cn1)C2]

A solution of 2-Fluoro-3-(4-{2-[3-(1-methyl-1H-pyrazol-4-yl)-phenyl]-pyrimidin-5-yl}-pyrazol-1-yl)-8-aza-bicyclo[3.2.1]octane (40 mg; 0.09 mmol; 1.00 eq.) in THF (4 mL) was added dropwise to a suspension of sodium hydride (7.44 mg; 0.19 mmol; 2.00 eq.) in THF (1.20 mL) maintained at 0° C. The reaction mixture was stirred for 30 minutes before the addition of Iodomethane (10 uL; 0.14 mmol; 1.50 eq.). It was stirred for an additional 4 h at RT, quenched with ice and extracted with ethyl acetate (30 mL×2). Combined organic layers were dried over anhydrous sodium sulfate, filtered and concentrated. Purification by flash chromatography on silica (CHCl3:MeOH, 95:5) afforded the title compound as a brown solid (20 mg, 45.5%). 1H NMR (DMSO; 1H) b 9.14 (s, 2H), 8.57-8.52 (m, 2H), 8.25-8.18 (m, 3H), 7.91 (s, 1H), 7.70 (d, J=7.8 Hz, 1H), 7.51 (t, J=7.8 Hz, 1H), 4.79-4.64 (m, 1H), 4.58-4.49 (m, 1H), 3.88 (s, 3H), 3.50-3.32 (m, 2H), 2.19-2.03 (m, 4H), 2.02-1.97 (m, 1H), 1.68-1.61 (m, 1H), 1.55-1.49 (m, 1H), 1.44-1.39 (m, 1H). HPLC: (max plot) 94%; (254 nm) 93%; Rt 3.05 min. LC/MS: 444.0 (M+1).

Example 23: {(R)-1-[3-(4-{2-[3-(1-Methyl-1H-pyrazol-4-yl)-phenyl]-pyrimidin-5-yl}-imidazol-1-yl)-cyclohexyl]-pyrrolidin-2-yl}-methanol (21)

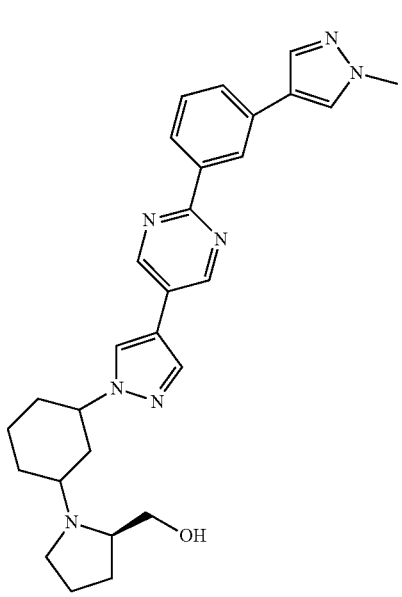 [SMILES: Cn1cc(-c2cccc(-c3ncc(-c4cnn(C5CCCC(N6CCC[C@@H]6CO)C5)c4)cn3)c2)cn1]

Step 1: {(R)-1-[3-(4-Bromo-pyrazol-1-yl)-cyclohexyl]-pyrrolidin-2-yl}-methanol

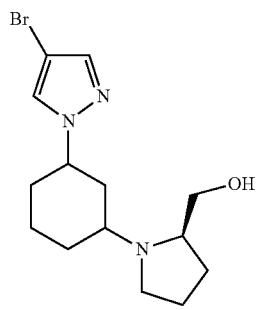 [SMILES: OC[C@H]1CCCN1C1CCCC(n2cc(Br)cn2)C1]

The title compound was obtained following procedure described for example 19, step 1, but starting from 3-(4-Bromo-pyrazol-1-yl)-cyclohexanone (1.0 g; 3.45 mmol; 1.00 eq.) and (R)-1-Pyrrolidin-2-yl-methanol (0.40 g; 3.80 mmol; 1.10 eq.) as a brown gum (1.20 g; 53%). LC/MS: 330 (M+1).

Step 2: {(R)-1-[3-(4-{2-[3-(1-Methyl-1H-pyrazol-4-yl)-phenyl]-pyrimidin-5-yl}-imidazol-1-yl)-cyclohexyl]-pyrrolidin-2-yl}-methanol The title compound was obtained following the procedure described for example 14, step 3, but starting from {(R)-1-[3-(4-Bromo-pyrazol-1-yl)-cyclohexyl]-pyrrolidin-2-yl}-methanol (150 mg; 0.23 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (109 mg; 0.25 mmol; 1.10 eq.) as a brown gum (19 mg, 16%). 1H NMR (DMSO) δ 9.16 (s, 2H), 8.54 (s, 2H), 8.25 (s, 1H), 8.22 (d, J=Hz, 1H), 8.12 (s, 1H), 7.91 (s, 1H), 0.71 (d, J=Hz, 1H), 7.52 (t, J=Hz, 1H), 4.46-0.00 (m, 1H), 4.27-4.23 (m, 2H), 3.88 (s, 3H), 3.04-0.00 (m, 1H), 2.84-2.83 (m, 3H), 2.06-2.03 (m, 3H), 1.87 (s, 2H), 1.74-1.67 (m, 8H). HPLC: (max plot) 95%; (254 nm) 95%; Rt 3.04 min. LC/MS: 484.2 (M+1).

Example 24: 1-[3-Hydroxymethyl-4-(4-{2-[3-(1-methyl-1H-pyrazol-4-yl)-phenyl]-pyrimidin-5-yl}-pyrazol-1-yl)-piperidin-1-yl]-ethanone (26)

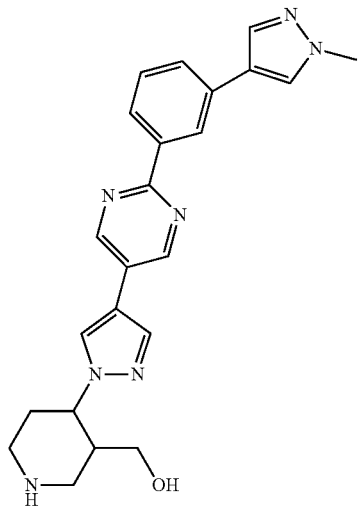 [SMILES: Cn1cc(-c2cccc(-c3ncc(-c4cnn(C5CCNCC5CO)c4)cn3)c2)cn1]

Step 1: 4-(N'-tert-Butoxycarbonyl-hydrazino)-3-(tert-butyl-dimethyl-silanyloxymethyl)-piperidine-1-carboxylic acid tert-butyl ester

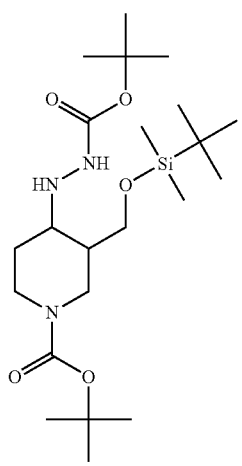 [SMILES: CC(C)(C)OC(=O)NNC1CCN(C(=O)OC(C)(C)C)CC1CO[Si](C)(C)C(C)(C)C]

The title compound was obtained following the procedure described for example 21, step 3, but starting from 3-(tert-Butyl-dimethyl-silanyloxymethyl)-4-oxo-piperidine-1-carboxylic acid tert-butyl ester (2.0 g; 5.59 mmol; 1.00 eq.) as a yellow gum (2.30 g; 11.6%, mixture of isomers). LC/MS (M+H) 460.0 (M+1).

Step 2: [4-(4-Bromo-pyrazol-1-yl)-piperidin-3-yl]-methanol

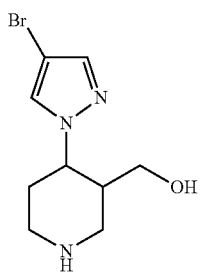

The title compound was obtained following the procedure described for example 21, step 4, but starting from 4-(N'-tert-Butoxycarbonyl-hydrazino)-3-(tert-butyl-dimethyl-silanyloxymethyl)-piperidine-1-carboxylic acid tert-butyl ester (2.30 g; 4.0 mmol; 1.00 eq.) as a yellow gum (900 mg; 25.9%). Mixture of isomers. LC/MS: 262.0 (M+1).

Step 3: [4-(4-{2-[3-(1-Methyl-1H-pyrazol-4-yl)-phenyl]-pyrimidin-5-yl}-pyrazol-1-yl)-piperidin-3-yl]-methanol The title compound was obtained following the procedure described for example 14, step 3, but starting from [4-(4-Bromo-pyrazol-1-yl)-piperidin-3-yl]-methanol (600 mg; 0.69 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (318 mg; 0.83 mmol; 1.20 eq.) as a white solid (280 mg, 95%). 1H NMR (DMSO; 1H) δ 9.15 (s, 2H), 8.52 (d, J=1.6 Hz, 1H), 8.46 (d, J=9.3 Hz, 1H), 8.26 (s, 1H), 8.21 (d, J=7.9 Hz, 1H), 8.12 (d, J=7.2 Hz, 1H), 7.91 (s, 1H), 7.70 (d, J=7.8 Hz, 1H), 7.52-7.50 (m, 1H), 4.34-4.31 (m, 1H), 4.19-4.16 (m, 1H), 4.11-4.09 (m, 2H), 3.88 (s, 3H), 3.19-3.02 (m, 3H), 2.50-2.48 (m, 1H), 2.10-2.10 (m, 1H), 1.91-1.85 (m, 3H). HPLC: (max plot) 98%; (mixture of isomers, 1:1); (254 nm) 98%; Rt 2.56-2.62 min. LC/MS: 416.2 (M+1).

Example 25: 1-[3-Hydroxymethyl-4-(4-{2-[3-(1-methyl-1H-pyrazol-4-yl)-phenyl]-pyrimidin-5-yl}-pyrazol-1-yl)-piperidin-1-yl]-ethanone (22)

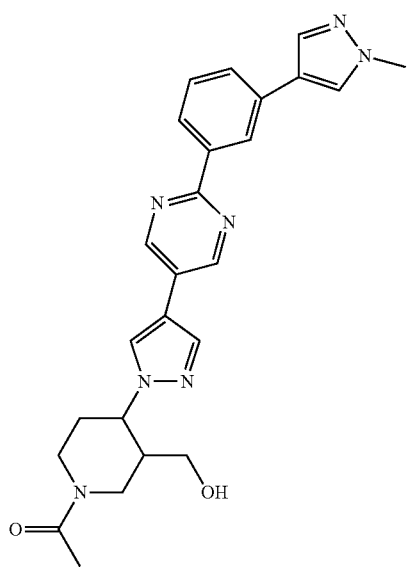 [SMILES: CC(=O)N1CCC(n2cc(-c3cnc(-c4cccc(-c5cnn(C)c5)c4)nc3)cn2)C(CO)C1]

Acetyl chloride (0.03 mL; 0.35 mmol; 1.50 eq.) was added to a solution of [4-(4-{2-[3-(1-Methyl-1H-pyrazol-4-yl)-phenyl]-pyrimidin-5-yl}-pyrazol-1-yl)-piperidin-3-yl]-methanol (100 mg; 0.24 mmol; 1.00 eq.) and Et₃N (0.09 mL; 0.71 mmol; 3.00 eq.) in dry DCM (5.00 mL) maintained at 0° C. The reaction mixture was then stirred at RT for 10 h. It was then washed with water and the organic layer was dried over anhydrous Na₂SO₄, filtered and concentrated. Purification by flash chromatography on silica (DCM: MeOH, 90:10) afforded the title compound as a white solid (70 mg, 62%). 1H NMR (DMSO; 1H) δ 9.16 (d, J=5.0 Hz, 2H), 8.52-8.48 (m, 2H), 8.25 (s, 1H), 8.22-8.16 (m, 1H), 7.91 (d, J=0.5 Hz, 1H), 7.71-7.69 (m, 1H), 7.51 (t, J=7.8 Hz, 1H), 4.71-4.66 (m, 1H), 4.65-4.64 (m, 1H), 4.41-4.40 (m, 1H), 4.00-3.98 (m, 1H), 3.89 (s, 3H), 3.50-3.32 (m, 1H), 3.22-3.21 (m, 1H), 3.20-3.08 (m, 1H), 3.00-2.86 (m, 1H), 2.32-2.31 (m, 1H), 2.07-1.96 (m, 5H). HPLC: (max plot) 97%; (254 nm) 96%; Rt 3.064 min. LC/MS: 458.0 (M+1). Mixture of isomers.

Example 26: 4-(4-{2-[3-(1-Methyl-1H-pyrazol-4-yl)-phenyl]-pyrimidin-5-yl}-pyrazol-1-yl)-azepan-2-one (23)

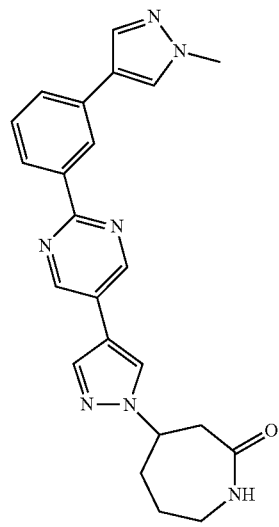 [SMILES: Cn1cc(-c2cccc(-c3ncc(-c4cnn(C5CCCNC(=O)C5)c4)cn3)c2)cn1]

Step 1: N'-(2-Oxo-azepan-4-yl)-hydrazinecarboxylic acid tert-butyl ester

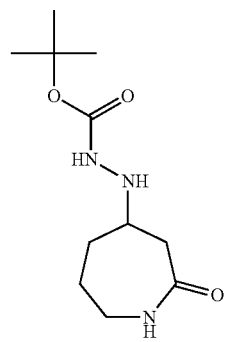 [SMILES: CC(C)(C)OC(=O)NNC1CCCNC(=O)C1]

The title compound was obtained following the procedure described for example 21 step 3, but starting from Azepane-2,4-dione (400 mg; 3.08 mmol; 1.00 eq.) and hydrazinecarboxylic acid tert-butyl ester (457 mg; 3.39 mmol; 1.10 eq.) as a yellow gum (750 mg, 97%). 1H NMR (DMSO; 1H) δ 8.24 (s, 1H), 7.46 (t, J=5.20 Hz, 1H), 4.33 (s, 1H), 3.10-2.94 (m, 2H), 2.90-2.78 (m, 1H), 2.37-2.27 (m, 2H), 1.84-1.74 (m, 2H), 1.38 (s, 9H), 1.33-1.26 (m, 2H).

Step 2: 4-(4-Bromo-pyrazol-1-yl)-azepan-2-one

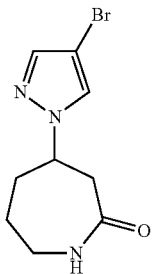 [SMILES: O=C1CC(n2cc(Br)cn2)CCCN1]

The title compound was obtained following the procedure described for example 21 step 4, but starting from N'-(2-Oxo-azepan-4-yl)-hydrazinecarboxylic acid tert-butyl ester (750 mg; 2.98 mmol; 1.00 eq.), 2-Bromo-malonaldehyde (556 mg; 3.57 mmol; 1.20 eq.) as a pale yellow gum (435 mg, 44%). 1H NMR (DMSO; 400 MHz) δ 8.02 (s, 1H), 7.75 (t, J=5.80 Hz, 1H), 7.55 (s, 1H), 4.43-4.37 (m, 1H), 3.22-3.15 (m, 4H), 3.10-3.05 (m, 2H), 2.41-2.39 (m, 1H), 2.36-2.20 (m, 1H), 2.11-2.05 (m, 3H), 1.87-1.82 (m, 2H), 1.50-1.48 (m, 1H), 1.46-1.43 (m, 1H), 1.38-1.37 (m, 1H).

Step 3: 4-(4-{2-[3-(1-Methyl-1H-pyrazol-4-yl)-phenyl]-pyrimidin-5-yl}-pyrazol-1-yl)-azepan-2-one The title compound was obtained following the procedure described for example 14 step 3, but starting from 4-(4-Bromo-pyrazol-1-yl)-azepan-2-one (430 mg; 1.49 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (895 mg; 2.23 mmol; 1.50 eq.), as a brown solid (420 mg, 68%). 1H NMR (DMSO; 400 MHz) δ 9.15 (s, 2H), 8.53-8.51 (m, 2H), 8.26 (s, 1H), 8.22-8.20 (m, 1H), 8.15 (s, 1H), 7.92-7.91 (m, 1H), 7.86-7.77 (m, 1H), 7.72-7.69 (m, 1H), 7.51 (t, J=7.72 Hz, 1H), 4.50-4.43 (m, 1H), 3.88 (s, 3H), 3.32-3.23 (m, 2H), 3.17-3.10 (m, 1H), 2.50-2.48 (m, 1H), 2.21-2.15 (m, 2H), 1.94-1.89 (m, 1H), 1.60-1.54 (m, 1H). HPLC: (max plot) 100%; (254 nm) 99%; Rt 3.28 min. LC/MS: 4314.0 (M+1).

Example 27: 1-Methyl-4-(4-{2-[3-(1-methyl-1H-pyrazol-4-yl)-phenyl]-pyrimidin-5-yl}-pyrazol-1-yl)-azepan-2-one (24)

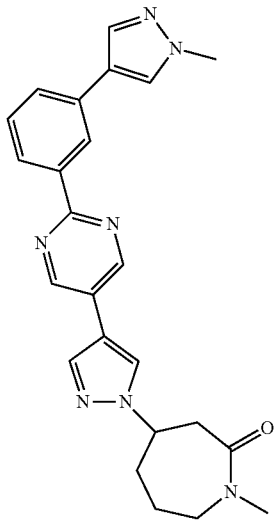 [SMILES: CN1CCCC(n2cc(-c3cnc(-c4cccc(-c5cnn(C)c5)c4)nc3)cn2)CC1=O]

A solution of 4-(4-{2-[3-(1-Methyl-1H-pyrazol-4-yl)-phenyl]-pyrimidin-5-yl}-pyrazol-1-yl)-azepan-2-one (150 mg; 0.36 mmol; 1.00 eq.) in THF (5 mL) was added in drop wise to a suspension of Sodium hydride (14.5 mg; 0.36 mmol; 1.00 eq.) in THF (5.00 mL) maintained under nitrogen atmosphere at 0° C. After 30 minutes, Iodomethane (50 uL; 0.72 mmol; 2.00 eq.) was added and the reaction mixture was stirred at RT for 4 h. It was quenched by addition of ice and extracted with ethyl acetate (30 mL×2). The combined organic layers were dried over anhydrous sodium sulfate, filtered and concentrated. Purification by flash column chromatography on silica (CHCl$_3$: MeOH, gradient from 95:5 to 90:10) afforded the title compound as a brown solid (120 mg; 0.27 mmol; 75%). 1H NMR (400 MHz, DMSO-d6) δ 9.15 (s, 2H), 8.53-8.52 (m, 1H), 8.49 (s, 1H), 8.26 (s, 1H), 8.22-8.20 (m, 1H), 8.15 (s, 1H), 7.91-7.91 (m, 1H), 7.72-7.69 (m, 1H), 7.51 (t, J=7.76 Hz, 1H), 4.46-4.40 (m, 1H), 3.88 (s, 3H), 3.71-3.64 (m, 1H), 3.60-3.54 (m, 1H), 3.40-3.20 (m, 1H), 2.90 (s, 3H), 2.62-2.48 (m, 1H), 2.19-2.13 (m, 2H), 1.92-1.90 (m, 1H), 1.82-1.63 (m, 1H). HPLC: (max plot) 96.4%; (254 nm) 98.6%; Rt 3.29 min. LC/MS: 428.0 (M+1).

Example 28: 5-{1-[3-(3,3-Difluoro-piperidin-1-yl)-cyclohexyl]-1H-pyrazol-4-yl}-2-[3-(1-methyl-1H-pyrazol-4-yl)-phenyl]-pyrimidine (25)

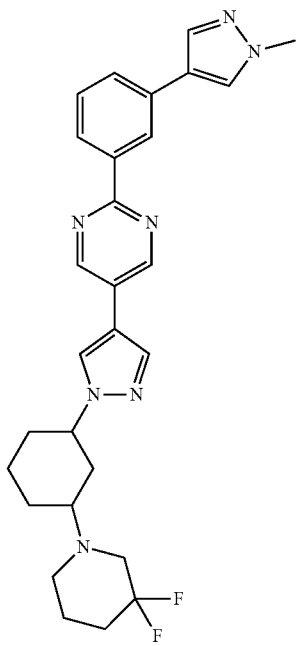 [SMILES: Cn1cc(-c2cccc(-c3ncc(-c4cnn(C5CCCC(N6CCCC(F)(F)C6)C5)c4)cn3)c2)cn1]

Step 1: 1-[3-(4-Bromo-pyrazol-1-yl)-cyclohexyl]-3,3-difluoro-piperidine

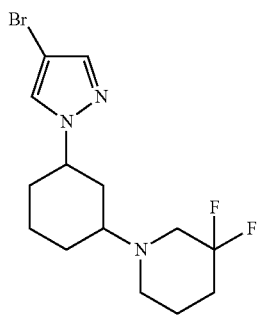 [SMILES: FC1(F)CCCN(C2CCCC(n3cc(Br)cn3)C2)C1]

The title compound was obtained following the procedure described for example 19, step 1, but starting from 3-(4-Bromo-pyrazol-1-yl)-cyclohexanone (250 mg; 0.86 mmol; 1.00 eq.) and 3,3-Difluoro-piperidine hydrochloride (204 mg; 1.29 mmol; 1.50 eq.) as a brown solid (200 mg, 59%). LC/MS: 350.0 (M+1).

Step 2: 5-{1-[3-(3,3-Difluoro-piperidin-1-yl)-cyclohexyl]-1H-pyrazol-4-yl}-2-[3-(1-methyl-1H-pyrazol-4-yl)-phenyl]-pyrimidine The title compound was obtained following the procedure described for example 14 step 3, but starting from 1-[3-(4-Bromo-pyrazol-1-yl)-cyclohexyl]-3,3-difluoro-piperidine (150 mg; 0.38 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (180 mg; 0.42 mmol; 1.10 eq.) as a brown gum (20 mg, 10%). 1H NMR (DMSO, 400 MHz) δ 9.08 (s, 2H), 8.59 (s, 1H), 8.36 (s, 1H), 8.27 (d, J=Hz, 2H), 8.11 (s, 1H), 8.06 (s, 1H), 7.91 (s, 1H), 7.70 (d, J=Hz, 1H), 7.52 (t, J=Hz, 1H), 4.48-4.46 (m, 1H), 3.97 (s, 3H), 3.68-3.66 (m, 2H), 3.56-3.53 (m, 1H), 3.32-0.00 (m, 1H), 2.59 (d, J=Hz, 1H), 2.17-2.14 (m, 8H), 1.91-1.90 (m, 1H), 1.90-1.90 (m, 3H). HPLC: (max plot) 98%; (254 nm) 99%; Rt 3.29 min. LC/MS: 504.0 (M+1).

Example 29: N-[(1S,3S)-3-(4-{2-[3-(1-Methyl-1H-pyrazol-4-yl)-phenyl]-pyrimidin-5-yl}-pyrazol-1-yl)-cyclohexyl]-methanesulfonamide (27)

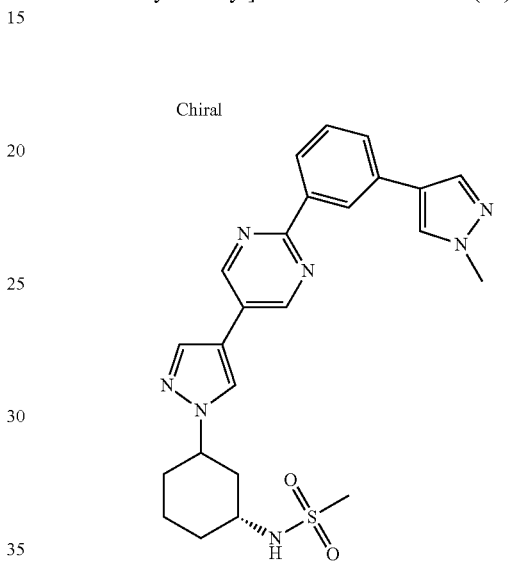

Step 1: N'—((R)-3-tert-Butoxycarbonylamino-cyclohexyl)-hydrazinecarboxylic acid tert-butyl ester

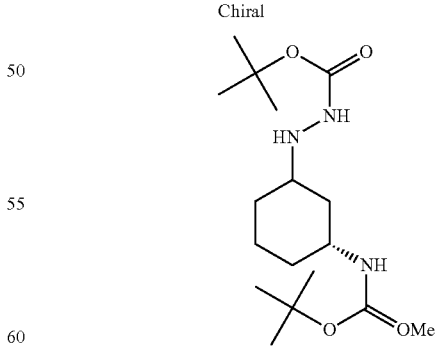

The title compound was obtained following the procedure described for example 21 step 3, but starting from (R)-3-Oxo-cyclohexyl)-carbamic acid tert-butyl ester (2.00 g; 8.91 mmol; 1.00 eq.) as a yellow solid (2.90 g; 96.6%). LC/MS: (max plot) 98%; Rt 3.51 min; 230.0 (M+1-Boc).

Step 2: (R)-3-(4-Bromo-pyrazol-1-yl)-cyclohexylamine

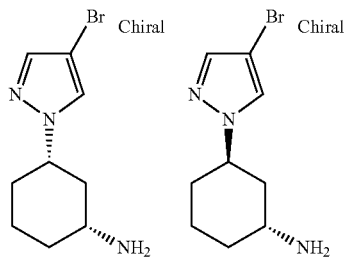 [SMILES: N[C@@H]1CCC[C@H](n2cc(Br)cn2)C1 ; N[C@@H]1CCC[C@@H](n2cc(Br)cn2)C1]

The title compound was obtained following the procedure described for example 21 step 4, but starting from N'—((R)-3-tert-Butoxycarbonylamino-cyclohexyl)-hydrazinecarboxylic acid tert-butyl ester (3.00 g; 8.90 mmol; 1.00 eq.) as a yellow gum (1 g, 34%). LC/MS: (max plot) 99%; (220 nm) 99%; Rt 2.2 min; 244.0 (M+1). The two isomers obtained were separated by preparative HPLC (chiralpak IA, hexane: EtOH: DEA; 80:20:0.1).

First eluting fraction: (1R,3S)-3-(4-Bromo-pyrazol-1-yl)-cyclohexylamine (200 mg) (configuration attributed based on NOE experiments conducted on racemic mixture, see example 30). HPLC: (max plot) 98.8%; (254 nm) 98.4%; Rt 2.25 min. Second eluting fraction: (1R,3R)-3-(4-Bromo-pyrazol-1-yl)-cyclohexylamine (200 mg). 1H NMR (DMSO; 400 MHz) δ 8.01 (s, 1H), 7.54 (s, 1H), 4.26-4.22 (m, 1H), 3.07-2.84 (m, 1H), 2.21-2.18 (m, 1H), 1.95-1.80 (m, 3H), 1.70-1.56 (m, 2H), 1.42-1.39 (m, 1H), 1.23-1.11 (m, 1H). HPLC: (max plot) 98.3%; (254 nm) 98.2%; Rt 2.27 min.

Step 3: (1R,3R)-3-(4-{2-[3-(1-Methyl-1H-pyrazol-4-yl)-phenyl]-pyrimidin-5-yl}-pyrazol-1-yl)-cyclohexylamine

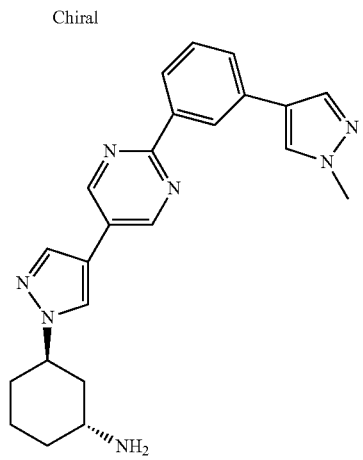 [SMILES: Cn1cc(-c2cccc(-c3ncc(-c4cnn([C@@H]5CCC[C@@H](N)C5)c4)cn3)c2)cn1]

The title compound was obtained following the procedure described for example 14 step 3, but starting from (1R,3R)-3-(4-Bromo-pyrazol-1-yl)-cyclohexylamine (200 mg; 0.81 mmol; 1.00 eq.) as a white solid (180 mg, 35%). LC/MS: (max plot) 95%; (254 nm) 97%; Rt 3.02 min; 400.00 (M+1).

Step 4: N-[(1R,3R)-3-(4-{2-[3-(1-Methyl-1H-pyrazol-4-yl)-phenyl]-pyrimidin-5-yl}-pyrazol-1-yl)-cyclohexyl]-methanesulfonamide Methanesulfonyl chloride (53.37 mg; 0.46 mmol; 1.20 eq.) was added dropwise to a solution of (1S,3S)-3-(4-{2-[3-(1-Methyl-1H-pyrazol-4-yl)-phenyl]-pyrimidin-5-yl}-pyrazol-1-yl)-cyclohexylamine (160 mg; 0.38 mmol; 1.00 eq.) and Triethylamine (0.11 mL; 0.76 mmol; 2.00 eq.) in DCM (1.60 mL) at 0° C. The reaction mixture was stirred for 2 h at RT, quenched with water (50 mL) and extracted with DCM (2×100 mL). The combined organic layers were dried over anhydrous sodium sulfate, filtrated and concentrated to give the title compound as a white solid (45 mg, 24%). 1H NMR (DMSO; 1H) δ 9.16 (s, 2H), 8.52 (t, J=1.60 Hz, 1H), 8.49 (s, 1H), 8.25 (s, 1H), 8.22-8.20 (m, 1H), 8.13 (s, 1H), 7.91-7.91 (m, 1H), 7.71-7.69 (m, 1H), 7.69-7.51 (m, 1H), 7.22 (d, J=7.48 Hz, 1H), 4.35-4.29 (m, 1H), 3.89 (s, 3H), 2.94 (s, 3H), 2.50-2.49 (m, 1H), 2.33-2.30 (m, 1H), 2.02 (d, J=10.80 Hz, 1H), 1.94 (d, J=12.32 Hz, 1H), 1.84 (d, J=13.60 Hz, 1H), 1.76-1.60 (m, 2H), 1.52-1.42 (m, 1H), 1.27 (t, J=12.52 Hz, 1H). HPLC: (max plot) 99%; (254 nm) 97%; Rt 3.7 min; LC/MS: 478.00 (M+1).

Example 30: N-[(1R,3S)-3-(4-{2-[3-(1-Methyl-1H-pyrazol-4-yl)-phenyl]-pyrimidin-5-yl}-pyrazol-1-yl)-cyclohexyl]-methanesulfonamide (28)

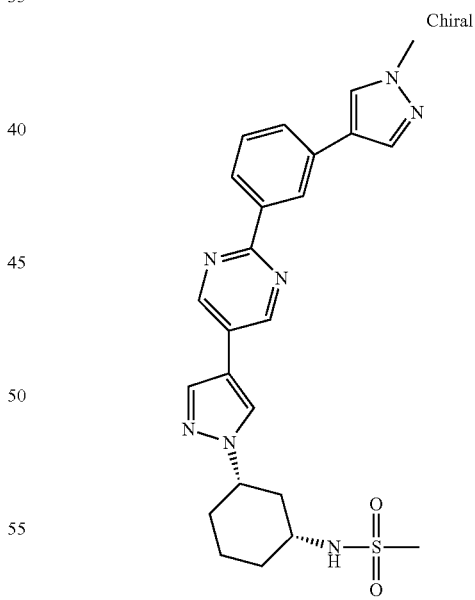

The title compound was prepared following similar procedures as for example 29, but using first eluting isomer from step 2 as a white solid. HPLC: (max plot) 98.6%; (254 nm) 96.1%; Rt 3.7 min; LC/MS: 478.3 (M+1).

Example 31: 5-[1-(3-Methoxymethyl-piperidin-4-yl)-1H-pyrazol-4-yl]-2-[3-(1-methyl-1H-pyrazol-4-yl)-phenyl]-pyrimidine (29)

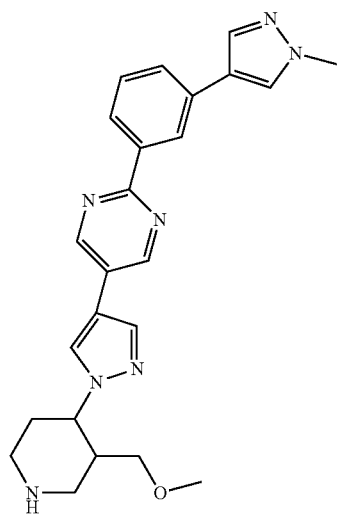 [SMILES: COCC1CNCCC1n1cc(-c2cnc(-c3cccc(-c4cnn(C)c4)c3)nc2)cn1]

Step 1: 1-[3-Methoxymethyl-4-(4-{2-[3-(1-methyl-1H-pyrazol-4-yl)-phenyl]-pyrimidin-5-yl}-pyrazol-1-yl)-piperidin-1-yl]-ethanone

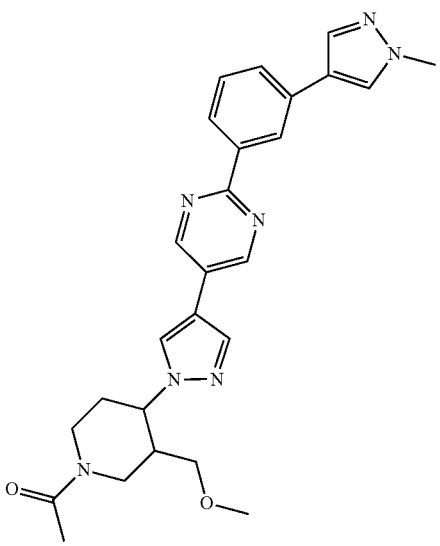 [SMILES: COCC1CN(C(C)=O)CCC1n1cc(-c2cnc(-c3cccc(-c4cnn(C)c4)c3)nc2)cn1]

A solution of 1-[3-Hydroxymethyl-4-(4-{2-[3-(1-methyl-1H-pyrazol-4-yl)-phenyl]-pyrimidin-5-yl}-pyrazol-1-yl)-piperidin-1-yl]-ethanone (200 mg; 0.41 mmol; 1.00 eq.) in THF (3 mL) was added dropwise to a suspension of Sodium hydride (60% in mineral oil) (32.57 mg; 0.81 mmol; 2.00 eq.) in THF (6.00 mL) maintained at 0° C. under nitrogen atmosphere. After 30 min, Iodomethane (0.04 mL; 0.61 mmol; 1.50 eq.) was added dropwise and the reaction mixture was stirred at RT for 4 h. It was quenched by addition of ice and extracted with ethyl acetate (20 mL×2). Combined organic layers were dried over anhydrous sodium sulfate, filtered and concentrated to give the title compound as a white solid (150 mg, 50%). LC/MS: 472.0 (M+1).

Step 2: 5-[1-(3-Methoxymethyl-piperidin-4-yl)-1H-pyrazol-4-yl]-2-[3-(1-methyl-1H-pyrazol-4-yl)-phenyl]-pyrimidine A solution of 1-[3-Methoxymethyl-4-(4-{2-[3-(1-methyl-1H-pyrazol-4-yl)-phenyl]-pyrimidin-5-yl}-pyrazol-1-yl)-piperidin-1-yl]-ethanone (150 mg; 0.20 mmol; 1.00 eq.) in Methanol (3.00 mL) was treated with an aqueous sodium hydroxide solution (15%, 6.00 mL). Reaction mixture was stirred at 60° C. for 6 h. It was evaporated, diluted with water and extracted with DCM (2×20 mL). The combined organic layers were washed with brine, dried over magnesium sulfate, filtered and concentrated. Purification by flash chromatography (CHCl₃/MeOH, 8:2) afforded the title compound as a white solid (20 mg; 22.4%). 1H NMR (DMSO, 400 Mhz) δ 9.17 (d, J=6.3 Hz, 2H), 8.52 (s, 1H), 8.47 (s, 1H), 8.25 (s, 1H), 8.21 (d, J=7.8 Hz, 1H), 8.16 (s, 1H), 7.91 (s, 1H), 7.70 (d, J=7.5 Hz, 1H), 7.50 (t, J=7.6 Hz, 1H), 3.88 (s, 3H), 3.32-3.15 (m, 6H), 2.20-2.00 (m, 2H), 1.94-1.92 (m, 1H). HPLC: (max plot) 97%; (254 nm) 95%; Rt 3.02 min. LC/MS: 430.0 (M+1).

Example 32: (1r,4r)-4-[4-(2-{3-[1-(2-Morpholin-4-yl-ethyl)-1H-pyrazol-4-yl]-phenyl}-pyrimidin-5-yl)-pyrazol-1-yl]-cyclohexanol (30)

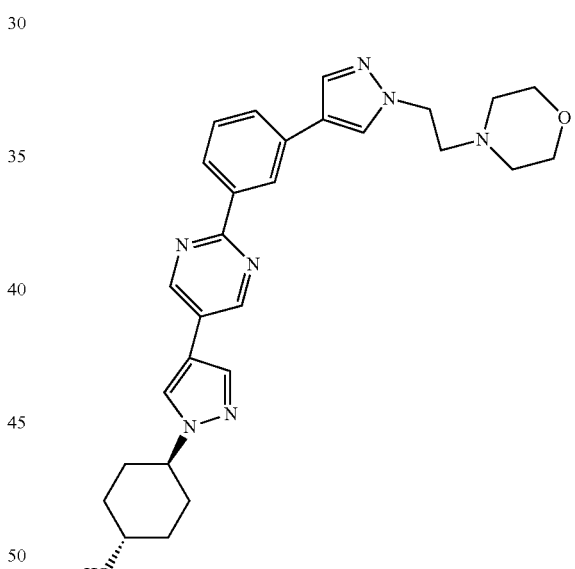

Step 1: 4-{2-[4-(3-Bromo-phenyl)-pyrazol-1-yl]-ethyl}-morpholine

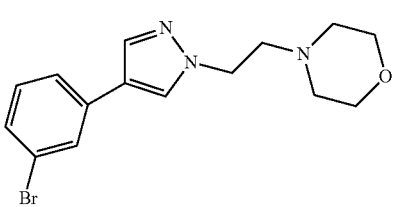 [SMILES: Brc1cccc(-c2cnn(CCN3CCOCC3)c2)c1]

A mixture of 4-{2-[4-(4,4,5,5-Tetramethyl-[1,3,2]dioxaborolan-2-yl)-pyrazol-1-yl]-ethyl}-morpholine (1.14 g; 3.64 mmol; 1.05 eq.), 1-Bromo-3-iodo-benzene (1.00 g; 3.46 mmol; 1.00 eq.), sodium carbonate (solution in 4 mL water, 0.74 g; 6.93 mmol; 2.00 eq.) in Toluene (10 mL) and EtOH (10 mL) was degassed before the addition of Tetrakis (triphenylphosphine)palladium (0.20 g; 0.17 mmol; 0.05 eq.) and heated to 100° C. for 4 h. It was then filtered through a celite p ad and the filtrate was concentrated under reduced pressure. Water (150 mL) was added to the residue and the mixture was extracted with ethyl acetate (2×150 mL). The organic layers were dried over anhydrous $Na_2SO_4$, filtered and concentrated to give the title compound as a yellow liquid (1.50 g; 93.7). LC/MS: (max plot) 73%; (254 nm) 88%; Rt 3.14 min; 338.0 (M+1).

Step 2: 4-(2-{4-[3-(4,4,5,5-Tetramethyl-[1,3,2]dioxaborolan-2-yl)-phenyl]-pyrazol-1-yl}-ethyl)-morpholine

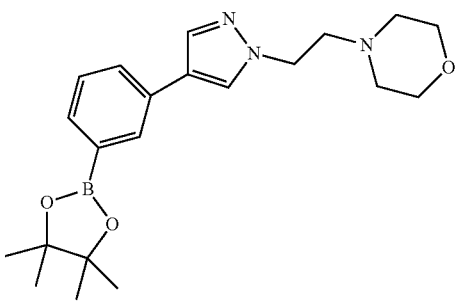 [SMILES: CC1(C)OB(c2cccc(-c3cnn(CCN4CCOCC4)c3)c2)OC1(C)C]

A mixture of 4-{2-[4-(3-Bromo-phenyl)-pyrazol-1-yl]-ethyl}-morpholine (1.50 g; 3.25 mmol; 1.00 eq.), 4,4,5,5,4',4',5',5'-Octamethyl-[2,2']bi[[1,3,2]dioxaborolanyl] (0.92 g; 3.57 mmol; 1.10 eq.) and Potassium; acetate (0.64 g; 6.49 mmol; 2.00 eq.) in DMF (15.00 mL), was degassed before the addition of 1,1'-Bis(diphenylphosphino)ferrocene]dichloropalladium(II).DCM (0.14 g; 0.16 mmol; 0.05 eq.). The reaction mixture was then heated to 80° C. for 16 h. It was then filtered through a celite pad and the filtrate was concentrated under reduced pressure. Water (150 mL) was added to the residue and the mixture was extracted with ethyl acetate (2×150 mL). The organic layers were dried over anhydrous $Na_2SO_4$, filtered and concentrated. Purification by flash chromatography on silica (Pet.Ether/EtOAc, 50:50) afforded the title compound as a brown liquid (0.75 g; 48.9%). LC/MS: (max plot) 81%; (254 nm) 79%; Rt 3.68 min; 384.0 (M+1).

Step 3: 4-(2-{4-[3-(5-Bromo-pyrimidin-2-yl)-phenyl]-pyrazol-1-yl}-ethyl)-morpholine

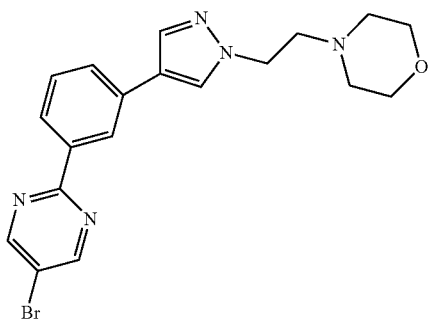 [SMILES: Brc1cnc(-c2cccc(-c3cnn(CCN4CCOCC4)c3)c2)nc1]

A mixture of 4-(2-{4-[3-(4,4,5,5-Tetramethyl-[1,3,2]dioxaborolan-2-yl)-phenyl]-pyrazol-1-yl}-ethyl)-morpholine (750 mg; 1.59 mmol; 1.00 eq.), 5-Bromo-2-iodo-pyrimidine (571 mg; 1.91 mmol; 1.20 eq.) and Potassium carbonate (452 mg; 3.18 mmol; 2.00 eq.) in Dioxane-1,4 (7.5 mL) and Water (7.50 mL) was degassed before the addition of Bis(triphenylphosphine)palladium (II) dichloride (45 mg; 0.06 mmol; 0.04 eq.). It was the heated to 100° C. for 12 h. It was then filtered through a celite pad and the filtrate was concentrated under reduced pressure. Water (100 mL) was added to the residue and the mixture was extracted with ethyl acetate (2×100 mL). The organic layers were dried over anhydrous $Na_2SO_4$, filtered and concentrated. Purification by flash chromatography on silica (Pet.Ether/EtOAc, 20:80) afforded the title compound as a yellow liquid (530 mg, 77%). 1H NMR (DMSO; 400 MHz) δ 9.09 (s, 2H), 8.49 (s, 1H), 8.30 (s, 1H), 8.17 (d, J=7.8 Hz, 1H), 7.92 (s, 1H), 7.75 (d, J=8.2 Hz, 1H), 7.52 (t, J=7.8 Hz, 1H), 4.25 (t, J=6.6 Hz, 2H), 3.55-3.53 (m, 4H), 2.75 (t, J=6.5 Hz, 2H), 2.42-2.39 (m, 4H). LC/MS: (max plot) 95%; (254 nm) 97%; Rt 3.34 min; 416.0 (M+1).

Step 4: 4-[2-(4-{3-[5-(4,4,5,5-Tetramethyl-[1,3,2]dioxaborolan-2-yl)-pyrimidin-2-yl]-phenyl}-pyrazol-1-yl)-ethyl]-morpholine

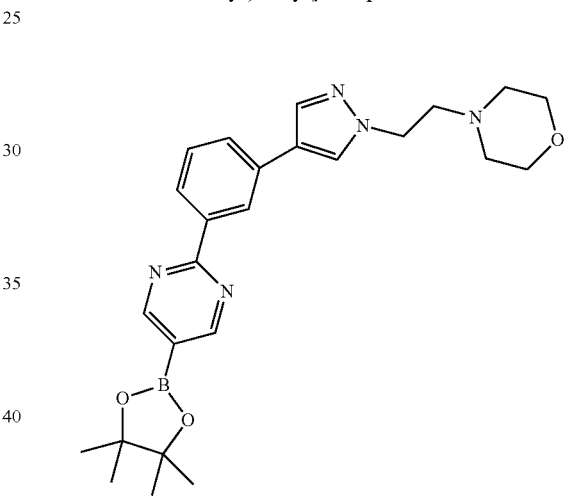

A mixture of 4-(2-{4-[3-(5-Bromo-pyrimidin-2-yl)-phenyl]-pyrazol-1-yl}-ethyl)-morpholine (530 mg; 1.22 mmol; 1.00 eq.), 4,4,5,5,4',4',5',5'-Octamethyl-[2,2']bi[[1,3,2]dioxaborolanyl] (347.21 mg; 1.34 mmol; 1.10 eq.), and Potassium acetate (241 mg; 2.44 mmol; 2.00 eq.) in Dioxane-1,4 (10.60 mL) was degassed before the addition to 1,1'-Bis(diphenylphosphino)ferrocene]dichloropalladium(II). DCM (51 mg; 0.06 mmol; 0.05 eq.) and heated to 100° C. for 6 h. It was then filtered through a celite pad and the filtrate was concentrated under reduced pressure. Water (100 mL) was added to the residue and the mixture was extracted with ethyl acetate (2×100 mL). The combined organic layers were dried over anhydrous $Na_2SO_4$, filtered and concentrated to give the title compound as a brown solid (590 mg; 1.11 mmol; 91.2%). LC/MS: (max plot) 87%; Rt 2.34 min; 380.2 (Boronate Ester Cleaved mass).

Step 5: Trans-4-[4-(2-{3-[1-(2-Morpholin-4-yl-ethyl)-1H-pyrazol-4-yl]-phenyl}-pyrimidin-5-yl)-pyrazol-1-yl]-cyclohexanol The title compound was obtained following the procedure described for example 14 step 3, but starting from 4-[2-(4-

{3-[5-(4,4,5,5-Tetramethyl-[1,3,2]dioxaborolan-2-yl)-pyrimidin-2-yl]-phenyl}-pyrazol-1-yl)-ethyl]-morpholine (200 mg; 0.38 mmol; 1.00 eq.) and 4-(4-Iodo-pyrazol-1-yl)-cyclohexanol (121 mg; 0.41 mmol; 1.10 eq.) as a white solid (75 mg; 37.3). 1H NMR (DMSO; 400 MHz) δ 9.14 (s, 2H), 8.52 (s, 1H), 8.48 (s, 1H), 8.31 (s, 1H), 8.20 (d, J=7.8 Hz, 1H), 8.10 (s, 1H), 7.92 (s, 1H), 7.70 (d, J=7.6 Hz, 1H), 7.50 (t, J=7.8 Hz, 1H), 4.70 (s, 1H), 4.26 (t, J=6.48 Hz, 2H), 4.21-4.15 (m, 1H), 3.55 (d, J=8.20 Hz, 4H), 3.51-3.50 (m, 1H), 2.75 (d, J=6.52 Hz, 2H), 2.49-2.42 (m, 4H), 2.07-2.04 (m, 2H), 1.95-1.93 (m, 2H), 1.86-1.76 (m, 2H), 1.41-1.33 (m, 2H). HPLC: (max plot) 94%; (254 nm) 95%; Rt 2.8 min. LC/MS: 500.3 (M+1).

Example 33: 1-(2-Hydroxy-ethyl)-8-(4-{2-[3-(1-methyl-1H-pyrazol-4-yl)-phenyl]-pyrimidin-5-yl}-pyrazol-1-yl)-1-aza-spiro[4.5]decan-2-one (31)

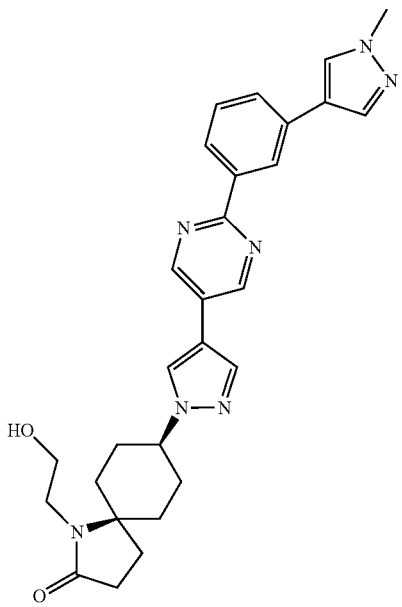 [SMILES: Cn1cc(-c2cccc(-c3ncc(-c4cnn([C@H]5CC[C@]6(CCC(=O)N6CCO)CC5)c4)cn3)c2)cn1]

Step 1: N'-(2-Oxo-1-aza-spiro[4.5]dec-8-yl)-hydrazinecarboxylic acid tert-butyl ester

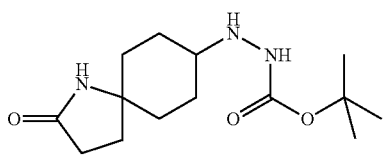 [SMILES: CC(C)(C)OC(=O)NNC1CCC2(CCC(=O)N2)CC1]

The title compound was obtained following the procedure described for example 21, step 3, but starting from 1-Aza-spiro[4.5]decane-2,8-dione (5.00 g; 28.41 mmol; 1.00 eq.) as a white gum (8 g, 78%). LC/MS: 284.2 (M+1). Mixture of isomers 1:1.

Step 2: 8-(4-Bromo-pyrazol-1-yl)-1-aza-spiro[4.5]decan-2-one

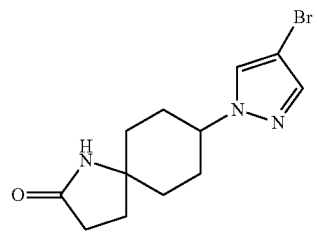 [SMILES: O=C1CCC2(CCC(n3cc(Br)cn3)CC2)N1]

The title compound was obtained following procedure described for example 21, step 4, but starting from N'-(2-Oxo-1-aza-spiro[4.5]dec-8-yl)-hydrazinecarboxylic acid tert-butyl ester (3.50 g; 12.30 mmol; 1.00 eq.) as a mixture of two isomers. Recrystallisation afforded the first isomer (cis isomer) as a white solid (500 mg). Concentration of the filtrate afforded the second isomer (trans) as a white solid (300 mg).

Step 3: [8-(4-Bromo-pyrazol-1-yl)-2-oxo-1-aza-spiro[4.5]dec-1-yl]-acetic acid ethyl ester

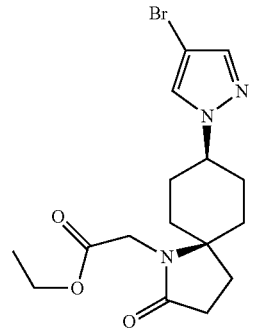 [SMILES: CCOC(=O)CN1C(=O)CC[C@]12CC[C@H](n1cc(Br)cn1)CC2]

A solution of cis-8-(4-bromo-1H-pyrazol-1-yl)-1-azaspiro[4.5]decan-2-one (100 mg; 0.26 mmol; 1.00 eq.) was added to a suspension of sodium hydride (60% in mineral oil) (21 mg; 0.52 mmol; 2.00 eq.) in dry Toluene (2.0 mL) maintained at 0° C. under nitrogen atmosphere. The reaction mixture was then refluxed at 110° C. for 1 h and cooled to RT before the addition of Tetrabutyl-ammonium bromide (4.3 mg; 0.01 mmol; 0.05 eq.) and Bromo-acetic acid ethyl ester (30 ul; 0.31 mmol; 1.20 eq.). It was stirred at RT for 18 h. Water was added and the mixture was extracted with ethyl acetate (2×30 mL). The combined organic layers were dried over anhydrous Na$_2$SO$_4$, filtered and concentrated to give the title compound as a yellow gum (120 mg, 28%). LC/MS: 384.0 (M+1).

Step 4: 8-(4-Bromo-pyrazol-1-yl)-1-(2-hydroxy-ethyl)-1-aza-spiro[4.5]decan-2-one

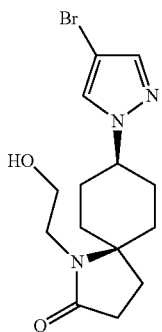 [SMILES: O=C1CC[C@]2(CC[C@H](n3cc(Br)cn3)CC2)N1CCO]

Sodium borohydride (5.6 mg; 0.15 mmol; 2.00 eq.) was added to a suspension of [8-(4-Bromo-pyrazol-1-yl)-2-oxo-1-aza-spiro[4.5]dec-1-yl]-acetic acid ethyl ester (120 mg; 0.07 mmol; 1.00 eq.) in Ethanol (3.60 mL) maintained at 0° C. The reaction mixture was stirred at 0° C. for 2 h, and then at RT for 16 h. A solution of citric acid (3N) was added dropwise until the mixture was completely soluble. The aqueous phase was extracted with DCM (2×15 mL) and the combined organic layers were dried over anhydrous Na$_2$SO$_4$, filtered and concentrated to give the title compound as a colourless gum (180 mg, 22%).

Step 5: 1-(2-Hydroxy-ethyl)-8-(4-{2-[3-(1-methyl-1H-pyrazol-4-yl)-phenyl]-pyrimidin-5-yl}-pyrazol-1-yl)-1-aza-spiro[4.5]decan-2-one The title compound was obtained following the procedure described for example 14 step 3, but starting from 8-(4-Bromo-pyrazol-1-yl)-1-(2-hydroxy-ethyl)-1-aza-spiro[4.5]decan-2-one (180 mg; 0.02 mmol; 1.00 eq.) and 2-[3-(1-Methyl-1H-pyrazol-4-yl)-phenyl]-5-(4,4,5,5-tetramethyl-[1,3,2]dioxaborolan-2-yl)-pyrimidine (6.7 mg; 0.02 mmol; 1.10 eq.) as a white solid (3 mg, 25%). LC/MS: 498.2 (M+1).

Example 34: 4-(4-{2-[3-(1-Piperidin-4-yl-1H-pyrazol-4-yl)-phenyl]-pyrimidin-5-yl}-pyrazol-1-yl)-cyclohexanol (32)

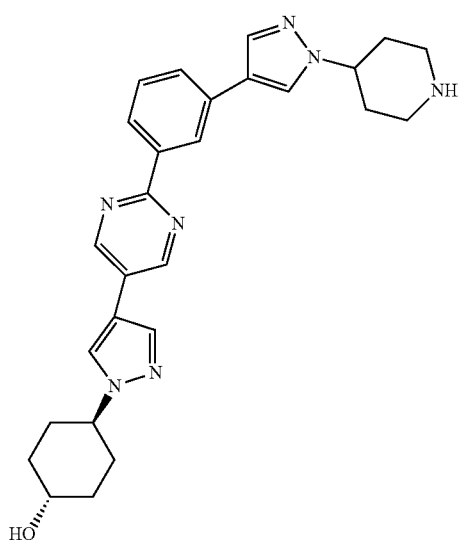 [SMILES: O[C@H]1CC[C@H](n2cc(-c3cnc(-c4cccc(-c5cnn(C6CCNCC6)c5)c4)nc3)cn2)CC1]

Step 1: 4-[4-(3-Bromo-phenyl)-pyrazol-1-yl]-piperidine-1-carboxylic acid tert-butyl ester

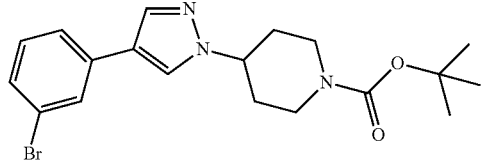 [SMILES: CC(C)(C)OC(=O)N1CCC(n2cc(-c3cccc(Br)c3)cn2)CC1]

The title compound was obtained following the procedure described for example 30 step 1, but starting from 4-[4-(4,4,5,5-Tetramethyl-[1,3,2]dioxaborolan-2-yl)-pyrazol-1-yl]-piperidine-1-carboxylic acid tert-butyl ester (1.40 g; 3.64 mmol; 1.05 eq.) as a yellow liquid (2.0 g, 91%). LC/MS: (max plot) 82%; (254 nm) 91%; Rt 5.51 min; 408.0 (M+1).

Step 2: 4-{4-[3-(4,4,5,5-Tetramethyl-[1,3,2]dioxa-borolan-2-yl)-phenyl]-pyrazol-1-yl}-piperidine-1-carboxylic acid tert-butyl ester

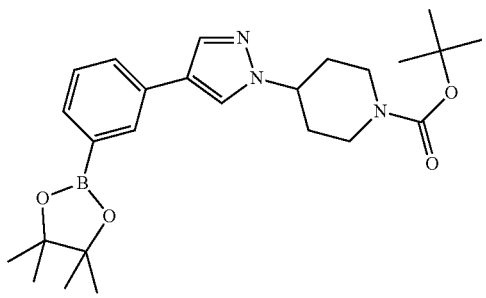 [SMILES: CC(C)(C)OC(=O)N1CCC(n2cc(-c3cccc(B4OC(C)(C)C(C)(C)O4)c3)cn2)CC1]

The title compound was obtained following the procedure described for example 30 step 2, but starting from 4-[4-(3-Bromo-phenyl)-pyrazol-1-yl]-piperidine-1-carboxylic acid tert-butyl ester (1.55 g; 3.15 mmol; 1.00 eq.) as a gum (2.0 g, 92%). LC/MS: 454.2 (M+1).

Step 3: 4-{4-[3-(5-Bromo-pyrimidin-2-yl)-phenyl]-pyrazol-1-yl}-piperidine-1-carboxylic acid tert-butyl ester

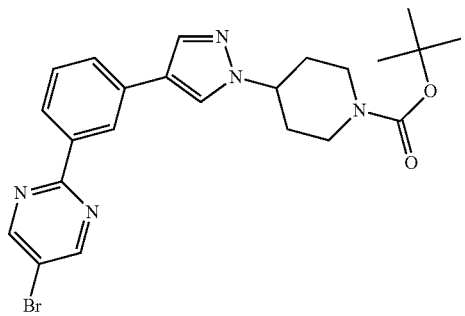 [SMILES: CC(C)(C)OC(=O)N1CCC(n2cc(-c3cccc(-c4ncc(Br)cn4)c3)cn2)CC1]

The title compound was obtained following the procedure described for example 30 step 3, but starting from 4-{4-[3-(4,4,5,5-Tetramethyl-[1,3,2]dioxaborolan-2-yl)-phenyl]-pyrazol-1-yl}-piperidine-1-carboxylic acid tert-butyl ester (1.78 g; 2.91 mmol; 1.00 eq) as a white solid (1.1 g, 75%). LC/MS: (max plot) 96%; (254 nm) 96%; Rt 5.57 min, 486 (M+1).

Step 4: 4-(4-{3-[5-(4,4,5,5-Tetramethyl-[1,3,2]dioxaborolan-2-yl)-pyrimidin-2-yl]-phenyl}-pyrazol-1-yl)-piperidine-1-carboxylic acid tert-butyl ester

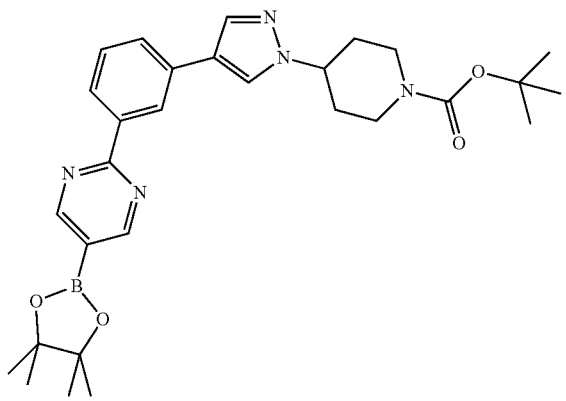 [SMILES: CC(C)(C)OC(=O)N1CCC(n2cc(-c3cccc(-c4ncc(B5OC(C)(C)C(C)(C)O5)cn4)c3)cn2)CC1]

The title compound was obtained following the procedure described for example 30 step 4, but starting from 4-{4-[3-(5-Bromo-pyrimidin-2-yl)-phenyl]-pyrazol-1-yl}-piperidine-1-carboxylic acid tert-butyl ester (1.10 g; 2.18 mmol; 1.00 eq.) as a Grey solid (1.1 g, 88%). LC/MS: (max plot) 93%; (254 nm) 87%; Rt 4.15 min; 452.2 (Boronate ester cleaved mass).

Step 5: 4-[4-(3-{5-[1-(4-Hydroxy-cyclohexyl)-1H-pyrazol-4-yl]-pyrimidin-2-yl}-phenyl)-pyrazol-1-yl]-piperidine-1-carboxylic acid tert-butyl ester

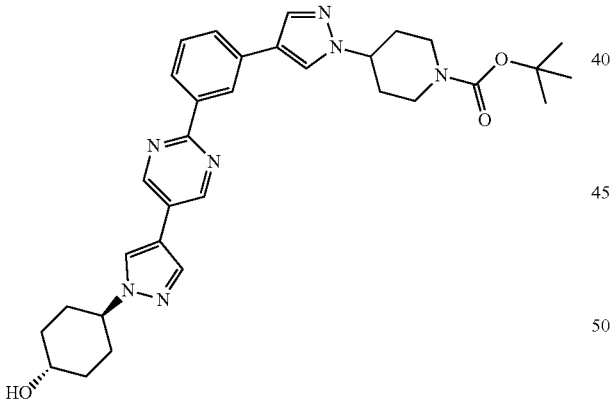

The title compound was obtained following the procedure described for example 14 step 3, but starting from 4-(4-{3-[5-(4,4,5,5-Tetramethyl-[1,3,2]dioxaborolan-2-yl)-pyrimidin-2-yl]-phenyl}-pyrazol-1-yl)-piperidine-1-carboxylic acid tert-butyl ester (400 mg; 0.70 mmol; 1.00 eq.) as a white solid (300 mg, 71%). LC/MS: (max plot) 94%; (254 nm) 92%; Rt 4.6 min; 570.2 (M+1).

Step 6: 4-(4-{2-[3-(1-Piperidin-4-yl-1H-pyrazol-4-yl)-phenyl]-pyrimidin-5-yl}-pyrazol-1-yl)-cyclohexanol A solution of HCl in Dioxane (3.00 mL; 12.00 mmol; 60.59 eq.) was added slowly to a solution of 4-[4-(3-{5-[1-(4-Hydroxy-cyclohexyl)-1H-pyrazol-4-yl]-pyrimidin-2-yl}-phenyl)-pyrazol-1-yl]-piperidine-1-carboxylic acid tert-butyl ester (120 mg; 0.20 mmol; 1.00 eq.) in Dioxane-1,4 (1.20 mL) maintained at 0° C. under nitrogen atmosphere. The reaction mixture was allowed to warm to RT and stirred for 3 h. A solution of NaHCO₃ (10%, 25 mL) was added and the mixture was extracted with DCM (2×50 mL). The combined organic layers were dried over anhydrous sodium sulfate, filtered and concentrated to give the title compound as a white solid (65 mg; 64%). 1H NMR (DMSO; 400 MHz) δ 9.14 (s, 2H), 8.53 (s, 1H), 8.48 (s, 1H), 8.31 (s, 1H), 8.20 (d, J=7.8 Hz, 1H), 8.10 (s, 1H), 7.92 (s, 1H), 7.72 (d, J=7.9 Hz, 1H), 7.50 (t, J=7.8 Hz, 1H), 4.69 (s, 1H), 4.24-4.15 (m, 2H), 3.52-3.47 (m, 1H), 3.07-3.04 (m, 2H), 2.66-2.62 (m, 2H), 2.07-2.04 (m, 2H), 2.00-1.93 (m, 4H), 1.88-1.76 (m, 4H), 1.41-1.33 (m, 2H), 1.06-1.01 (m, 1H). HPLC: (max plot) 91%; (254 nm) 90%; Rt 2.85 min. LC/MS: 470.2 (M+1).

Example 35: Ethenesulfonic acid Cis-[3-4-{2-[3-(1-methyl-1H-pyrazol-4-yl)-phenyl]-pyrimidin-5-yl}-pyrazol-1-yl)-cyclohexyl]-amide (33)

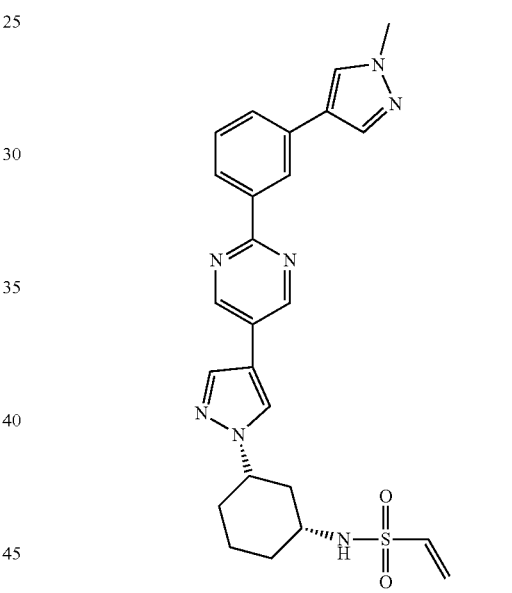

Step 1: N'-(3-tert-Butoxycarbonylamino-cyclohexyl)-hydrazinecarboxylic acid tert-butyl ester

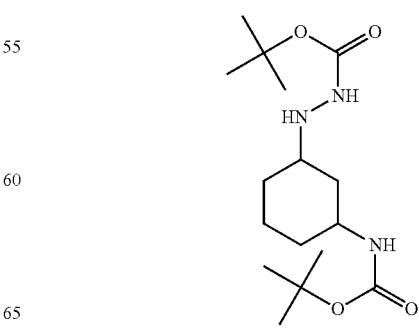

The title compound was obtained following the procedure described for example 21 step 3, but starting from (3-Oxo-cyclohexyl)-carbamic acid tert-butyl ester (3.00 g; 13.36 mmol; 1.00 eq.) as a white solid (4.0 g, 96%). LC/MS: (max plot) 98%; Rt 3.5 min; 330.2 (M+1).

Step 2: Cis-3-(4-Bromo-pyrazol-1-yl)-cyclohexylamine and Trans-3-(4-Bromo-pyrazol-1-yl)-cyclohexylamine (racemic)

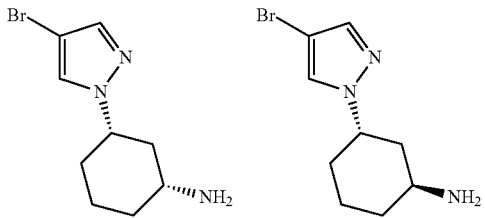 [SMILES: N[C@@H]1CCC[C@H](n2cc(Br)cn2)C1 ; N[C@H]1CCC[C@H](n2cc(Br)cn2)C1]

The title compound was obtained following the procedure described for example 21 step 4, but starting from N'-(3-tert-Butoxycarbonylamino-cyclohexyl)-hydrazinecarboxylic acid tert-butyl ester (4.30 g; 12.80 mmol; 1.00 eq.). The crude (1.9 g, mixture of isomers) was purified by preparative HPLC (CHIRALPAK IA, 0.1% DEA in hexane:EtOH: 80:20) and yielded to the title compound as a brown gum (first eluting, Cis, 500 mg, 32%). 1H NMR (DMSO; 400 MHz) δ 8.01 (s, 1H), 7.54 (s, 1H), 4.26-4.22 (m, 1H), 3.16-3.05 (m, 1H), 2.21-2.18 (m, 1H), 1.95-1.80 (m, 3H), 1.71-1.56 (m, 2H), 1.42-1.39 (m, 1H), 1.22-1.14 (m, 1H). Cis isomer structure was attributed based on NOE experiments (irradiation of 3.1 ppm and 4.2 ppm protons). HPLC: (max plot) 97%; (220 nm) 97%; Rt 2.25 min. The second eluting fraction contained the Trans isomer (170 mg, 11%).

Step 3: Cis-3-(4-{2-[3-(1-Methyl-1H-pyrazol-4-yl)-phenyl]-pyrimidin-5-yl}-pyrazol-1-yl)-cyclohexylamine

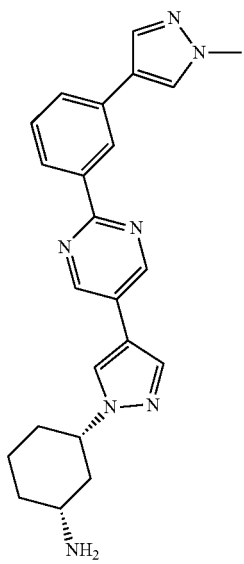 [SMILES: Cn1cc(-c2cccc(-c3ncc(-c4cnn([C@H]5CCC[C@@H](N)C5)c4)cn3)c2)cn1]

The title compound was obtained following the procedure described for example 14 step 3, but starting from 2-[3-(1-Methyl-1H-pyrazol-4-yl)-phenyl]-5-(4,4,5,5-tetramethyl-[1,3,2]dioxaborolan-2-yl)-pyrimidine (303 mg; 0.79 mmol; 1.10 eq.) and Cis-3-(4-Bromo-pyrazol-1-yl)-cyclohexylamine (180 mg, 0.72 mmol, 1.0 eq) as a brown solid (120 mg, 41%). LC/MS: (max plot) 99%; (254 nm) 99%; Rt 2.93 min; 400.2 (M+1).

Step 4: Ethenesulfonic acid Cis-[-3-4-{2-[3-(1-methyl-1H-pyrazol-4-yl)-phenyl]-pyrimidin-5-yl}-pyrazol-1-yl)-cyclohexyl]-amide A solution of vinylsulfonyl chloride (25. mg; 0.20 mmol; 2.00 eq.) in DCM (5 mL) was added slowly to a solution of Cis-3-(4-{2-[3-(1-Methyl-1H-pyrazol-4-yl)-phenyl]-pyrimidin-5-yl}-pyrazol-1-yl)-cyclohexylamine (40 mg; 0.10 mmol; 1.00 eq.) and TEA (30 uL, 0.20 mmol; 2.00 eq.) in DCM (10 mL) maintained at 0° C. The reaction mixture was then stirred at RT for 1 h before the addition of water. The aqueous layer was further extracted with DCM (25 mL) and the combined organic layers were washed with brine, dried over anhydrous sodium sulphate, filtered and concentrated. Purification by flash chromatography on silica (DCM: MeOH; 95:5) afforded the title compound as a white solid (30 mg, 62%). 1H NMR (DMSO; 400 MHz) δ 9.15 (s, 2H), 8.52 (s, 1H), 8.47 (s, 1H), 8.25 (s, 1H), 8.20 (d, J=7.8 Hz, 1H), 8.12 (s, 1H), 7.91 (s, 1H), 7.70 (d, J=7.6 Hz, 1H), 7.50 (t, J=7.7 Hz, 2H), 6.77 (dd, J=9.9, 16.5 Hz, 1H), 6.05 (d, J=16.44 Hz, 1H), 5.93 (d, J=9.92 Hz, 1H), 4.33-4.27 (m, 1H), 3.88 (s, 3H), 3.23-3.20 (m, 1H), 2.27-2.24 (m, 1H), 2.07-1.98 (m, 1H), 1.90-1.81 (m, 2H), 1.76-1.59 (m, 2H), 1.49-1.39 (m, 1H), 1.28-1.25 (m, 1H). HPLC: (max plot) 100%; (254 nm) 99%; Rt 3.95 min. LC/MS: 490.0 (M+1).

Example 36: imino(methyl)(Cis-3-(4-(2-(3-(1-methyl-1H-pyrazol-4-yl)phenyl)pyrimidin-5-yl)-1H-pyrazol-1-yl)cyclohexyl)-l6-sulfanone (34)

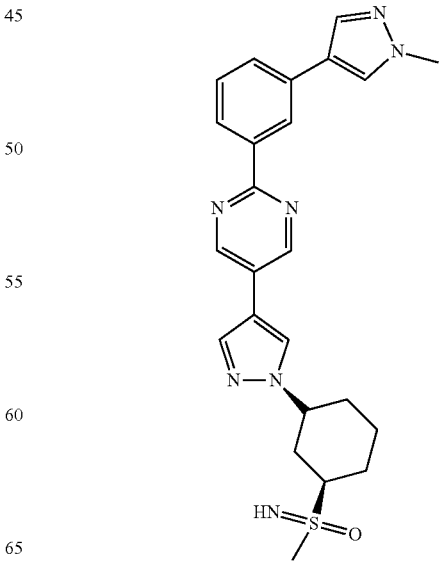

Step 1: N'-(3-Methylsulfanyl-cyclohexyl)-hydrazinecarboxylic acid tert-butyl ester

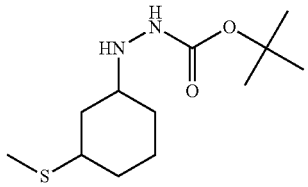 [SMILES: CSC1CCCC(NNC(=O)OC(C)(C)C)C1]

The title compound was obtained following the procedure described for example 21 step 3, but starting from 3-Methylsulfanyl-cyclohexanone (10 g; 65.86 mmol; 1.00 eq.) as a yellow solid (17 g, 98%). LC/MS: (max plot) 93%; (ELSD, mixture of isomers 1:1); Rt 3.08-3.16 min; 205 (t-butyl ester cleaved mass).

Step 2: 4-Bromo-1-Cis-3-methylsulfanyl-cyclohexyl)-1H-pyrazole and 4-Bromo-1-Trans-3-methylsulfanyl-cyclohexyl)-1H-pyrazole

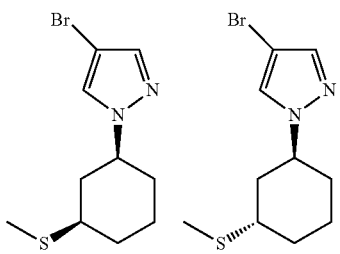

The title compounds were obtained following the procedure described for example 21 step 4, but starting from N'-(3-Methylsulfanyl-cyclohexyl)-hydrazinecarboxylic acid tert-butyl ester (17 g; 60.47 mmol; 1.00 eq.). The crude was purified by preparative HPLC (XBridge C8). First eluting isomer: colorless gum, 450 mg, cis isomer. 1H NMR (DMSO, 400 MHz) δ 8.02 (s, 1H), 7.51 (s, 1H), 4.24-4.18 (m, 1H), 2.73-2.48 (m, 1H), 2.28-2.05 (m, 1H), 1.98 (s, 3H), 1.95-1.91 (m, 2H), 1.87-1.82 (m, 1H), 1.71-1.61 (m, 2H), 1.45-1.41 (m, 1H), 1.21-1.17 (m, 1H). HPLC (Column: Symmetry C18 (75×4.6) mm, 3.5 µm; A: 0.1% TFA in H2O, B: ACN; Flow Rate: 0.8 mL/min): (max plot) 98%; Rt 8.713 min. LC/MS: 277.0 (M+1). Second eluting isomer: colorless gum, 350 mg, trans isomer. 1H NMR (DMSO, 400 MHz) δ 8.05 (s, 1H), 4.45-4.42 (m, 1H), 3.18-3.16 (m, 1H), 2.23-2.22 (m, 1H), 2.21-2.16 (m, 4H), 1.92-1.90 (m, 1H), 1.80-1.59 (m, 5H). HPLC (Column: Symmetry C18 (75×4.6) mm, 3.5 µm; A: 0.1% TFA in H2O, B: ACN; Flow Rate: 0.8 mL/min): (max plot) 97%; Rt 9.043 min. LC/MS: 277.0 (M+1). Cis and trans isomers were attributed based on NOE experiments.

Step 3: N-(Cis-3-(3-bromo-1H-pyrazol-1-yl)cyclohexyl)(methyl)-I4-sulfanylidene)-4-methylbenzenesulfonamide

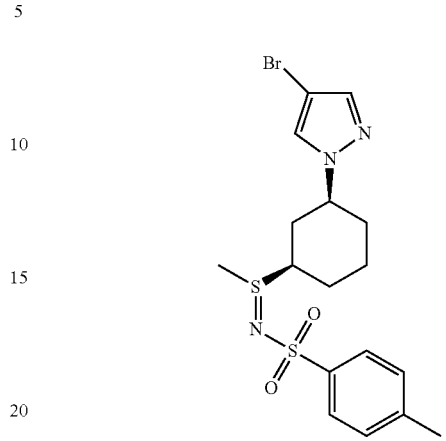

A mixture of 4-Bromo-1-(Cis-3-methylsulfanyl-cyclohexyl)-1H-pyrazole (450 mg; 1.61 mmol; 1.00 eq.) and chloramine T (Trihydrate) (554 mg; 1.93 mmol; 1.20 eq.) in Acetonitrile (9 mL) was stirred at RT for 16 h. Acetonitrile was removed under reduced pressure and the residue was diluted with DCM (50 mL), washed with water, dried over anhydrous sodium sulfate, filtered and concentrated to give the title compound as a colorless gum (400 mg, 35%). LC/MS: 445.0 (M+1).

Step 4: N-((Cis-3-(3-bromo-1H-pyrazol-1-yl)cyclohexyl)(methyl)(oxo)-I6-sulfanylidene)-4-methylbenzenesulfonamide

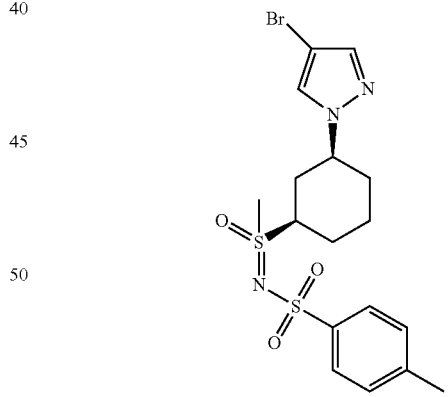

A mixture of N-(Cis-3-(3-bromo-1H-pyrazol-1-yl)cyclohexyl)(methyl)-I4-sulfanylidene)-4-methylbenzenesulfonamide (400 mg; 0.57 mmol; 1.00 eq.), Potassium carbonate (161.76 mg; 1.14 mmol; 2.00 eq.) and Hydrogen peroxide, 30% solution (290 ul; 2.84 mmol; 5.00 eq.), in EtOH (8.00 mL) and Acetonitrile (2.00 mL; 5.00 V) was stirred at RT for 16 h. Water (30 mL) was added and the reaction mixture was extracted with DCM (2×30 mL). Combined organic layers were dried over anhydrous Na2SO4, filtered and concentrated to give the title compound as a colorless gum (250 mg, 58%).

Step 5: Cis-3-(3-bromo-1H-pyrazol-1-yl)cyclohexyl)(imino)(methyl)-l6-sulfanone

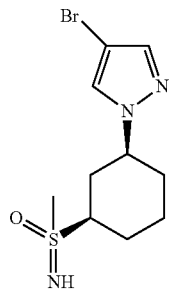 [SMILES: CS(=N)(=O)[C@@H]1CCC[C@H](n2cc(Br)cn2)C1]

A solution of sodium anthracenide (prepared by adding Metallic sodium (91 mg; 3.93 mmol; 15.00 eq.) to Anthracene (723 mg; 3.93 mmol; 15.00 eq.) in 1,2-Dimethoxyethane (6.0 mL) and subsequently stirred approximately 15 h until the dark brown color develops indicating the complete formation of anion) was added to a solution of N-((Cis-3-(3-bromo-1H-pyrazol-1-yl)cyclohexyl)(methyl)(oxo)-l6-sulfanylidene)-4-methylbenzenesulfonamide (200 mg; 0.26 mmol; 1.00 eq.) in 1,2-dimethoxyethane until decolorization no longer occurred. The reaction mixture was then made acidic by addition of a 1.5N HCl solution (5 mL). It was extracted with DCM (20 mL). The aqueous layer was basified with $Na_2CO_3$, evaporated under reduced pressure and DCM (30 mL) was added to the residue. The suspension obtained was stirred at RT and filtered. The filtrate was finally concentrated under reduced pressure to afford the title compound as a brown gum (70 mg, 81%). LC/MS: 306.0 (M+1).

Step 6: imino(methyl)(Cis-3-(4-(2-(3-(1-methyl-1H-pyrazol-4-yl)phenyl)pyrimidin-5-yl)-1H-pyrazol-1-yl)cyclohexyl)-l6-sulfanone The title compound was obtained following the procedure described for example 14 step 3, but starting from (Cis-3-(3-bromo-1H-pyrazol-1-yl)cyclohexyl)(imino)(methyl)-l6-sulfanone (70 mg; 0.21 mmol; 1.00 eq.) as a brown solid (10 mg, 10%). 1H NMR (DMSO; 400 MHz) δ 9.16 (s, 2H), 8.60 (s, 1H), 8.55 (s, 1H), 8.25 (s, 1H), 8.21 (d, J=7.9 Hz, 1H), 8.15 (s, 1H), 7.91 (s, 1H), 7.70 (d, J=7.9 Hz, 1H), 7.50 (t, J=7.8 Hz, 1H), 4.4-4.37 (m, 1H), 3.88 (s, 3H), 3.68 (d, J=6.28 Hz, 1H), 3.32 (s, 1H), 3.32 (s, 3H), 2.49 (t, J=1.76 Hz, 1H), 2.18-2.07 (m, 2H), 1.92-1.89 (m, 1H), 1.88-1.85 (m, 1H), 1.78-1.73 (m, 1H), 1.54-1.34 (m, 2H). HPLC: (max plot) 94%; (254 nm) 94%; Rt 3.09 min. LC/MS: 462.0 (M+1).

Example 37: imino(methyl)(Trans)-3-(4-(2-(3-(1-methyl-1H-pyrazol-4-yl)phenyl)pyrimidin-5-)-1H-pyrazol-1-yl)cyclohexyl)-l6-sulfanone (35)

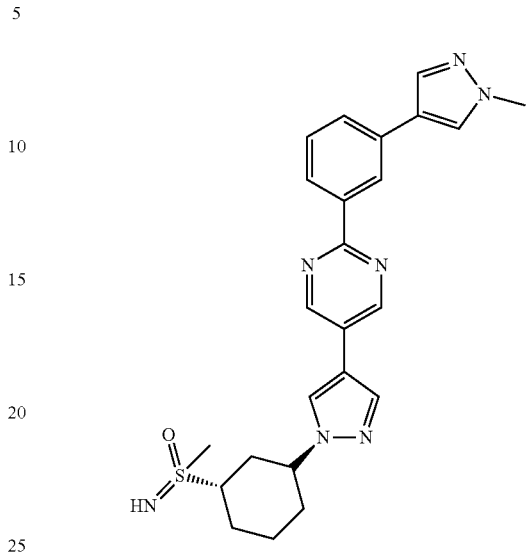

The title compound was obtained following procedure described for example 36, but starting from the trans isomer obtained in step 2. 1H NMR (MeOD; 400 MHz) δ 9.08 (s, 2H), 8.59 (t, J=1.6 Hz, 1H), 8.37 (s, 1H), 8.27-8.24 (m, 1H), 8.07 (d, J=11.0 Hz, 1H), 7.91 (d, J=0.6 Hz, 1H), 7.70-7.68 (m, 1H), 7.50 (t, J=7.8 Hz, 1H), 4.44-4.40 (m, 1H), 3.97 (s, 3H), 3.32 (s, 3H), 2.69-2.66 (m, 1H), 2.32-2.30 (m, 1H), 2.24-2.20 (m, 1H), 2.16-2.10 (m, 1H), 2.02-1.85 (m, 2H), 1.68-1.61 (m, 2H). HPLC: (max plot) 93%; (254 nm) 92%; Rt 3.1 min. LC/MS: 462.3 (M+1).

Example 38: Cis-N-[-3-4-{2-[3-(1-Methyl-1H-pyrazol-4-yl)-phenyl]-pyrimidin-5-yl}-pyrazol-1-yl)-cyclohexyl]-acrylamide (36)

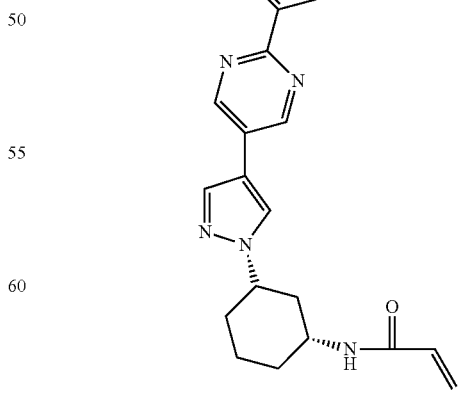

A solution of Acryloyl chloride (20 uL; 0.30 mmol; 2.00 eq.) in DCM (5 mL) was slowly added to a solution of Cis-3-(4-{2-[3-(1-Methyl-1H-pyrazol-4-yl)-phenyl]-pyrimidin-5-yl}-pyrazol-1-yl)-cyclohexylamine (60 mg; 0.15 mmol; 1.00 eq.) and TEA (40 uL, 2 eq.) in DCM (15 mL) maintained at 0° C. The reaction mixture was then stirred at RT for 1 h before the addition of water. The aqueous layer was further extracted with DCM (25 mL) and the combined organic layers were washed with brine, dried over anhydrous sodium sulphate, filtered and concentrated. Purification by flash chromatography on silica (DCM:MeOH; 95:5) afforded the title compound as a white solid (40 mg, 59%). 1H NMR (DMSO; 400 MHz) δ 9.15 (s, 2H), 8.52 (s, 1H), 8.49 (s, 1H), 8.25 (s, 1H), 8.20 (d, J=7.9 Hz, 1H), 8.16 (bs, 1H), 8.13 (s, 1H), 7.91 (s, 1H), 7.70 (d, J=7.8 Hz, 1H), 7.50 (t, J=7.8 Hz, 1H), 6.20 (dd, J=9.96, 17.08 Hz, 1H), 6.08 (dd, J=2.36, 17.08 Hz, 1H), 5.57 (d, J=7.60 Hz, 1H), 4.37-4.31 (m, 1H), 3.88 (s, 3H), 3.88-3.84 (m, 1H), 2.30-2.24 (m, 1H), 2.08-2.05 (m, 1H), 1.88-1.85 (m, 2H), 1.73-1.64 (m, 2H), 1.55-1.49 (m, 1H), 1.27-1.18 (m, 1H). HPLC: (max plot) 100%; (254 nm) 99%; Rt 3.63 min. LC/MS: 454.2 (M+1).

Example 39: Ethenesulfonic acid [Trans-3-(4-{2-[3-(1-methyl-1H-pyrazol-4-yl)-phenyl]-pyrimidin-5-yl}-pyrazol-1-yl)-cyclohexyl]-amide (37)

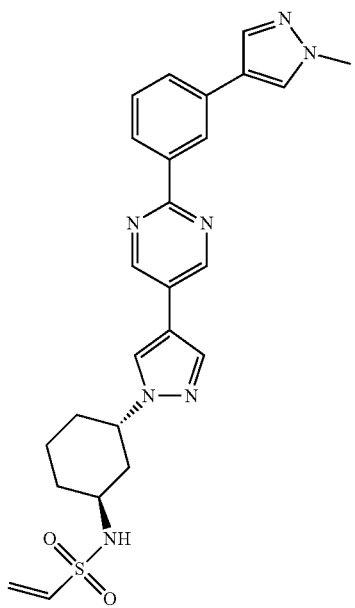 [SMILES: C=CS(=O)(=O)N[C@H]1CCC[C@H](n2cc(-c3cnc(-c4cccc(-c5cnn(C)c5)c4)nc3)cn2)C1]

The title compound was obtained following the procedure described for example 32 but using the trans isomer from step 2 as a white solid (25 mg, 51%). 1H NMR (DMSO; 400 MHz) δ 9.16 (s, 2H), 8.52 (s, 1H), 8.46 (s, 1H), 8.25 (s, 1H), 8.21 (d, J=8.0 Hz, 1H), 8.13 (s, 1H), 7.91 (s, 1H), 7.70 (d, J=8.2 Hz, 1H), 7.52-7.48 (m, 2H), 6.74 (dd, J=10.0, 16.5 Hz, 1H), 6.04 (d, J=16.44 Hz, 1H), 5.96 (d, J=9.96 Hz, 1H), 4.58-4.53 (m, 1H), 3.88 (s, 3H), 3.63-3.60 (m, 1H), 2.13-2.07 (m, 2H), 2.04-1.97 (m, 1H), 1.85-1.73 (m, 2H), 1.63-1.58 (m, 3H). HPLC: (max plot) 99%; (254 nm) 97%; Rt 4.01 min. LC/MS: 490.2 (M+1).

Example 40: N-[(1S,3S)-3-(4-{2-[3-(1-Methyl-1H-pyrazol-4-yl)-phenyl]-pyrimidin-5-yl}-pyrazol-1-yl)-cyclohexyl]-acrylamide (38)

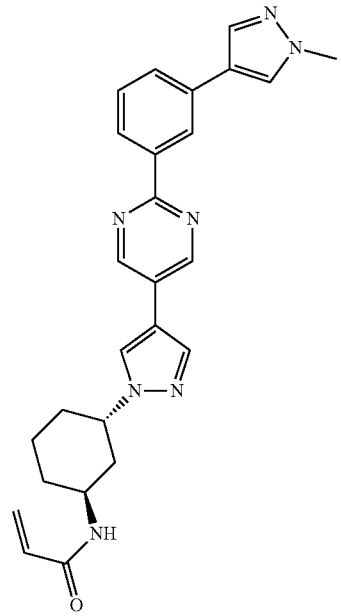 [SMILES: C=CC(=O)N[C@H]1CCC[C@H](n2cc(-c3cnc(-c4cccc(-c5cnn(C)c5)c4)nc3)cn2)C1]

The title compound was obtained following the procedure described for example 35 but using the trans isomer prepared in example 32, step 2 as a white solid (35 mg, 52%). 1H NMR (DMSO; 400 MHz) δ 9.16 (s, 2H), 8.52 (s, 2H), 8.25 (s, 1H), 8.21 (d, J=8.0 Hz, 1H), 8.16 (d, J=7.4 Hz, 1H), 8.13 (s, 1H), 7.91 (s, 1H), 7.70 (d, J=8.0 Hz, 1H), 7.50 (t, J=7.8 Hz, 1H), 6.35 (dd, J=10.2, 17.0 Hz, 1H), 6.10 (dd, J=2.24, 17.04 Hz, 1H), 5.60 (d, J=7.88 Hz, 1H), 4.57-4.52 (m, 1H), 4.22-4.20 (m, 1H), 3.88 (s, 3H), 2.11-2.02 (m, 3H), 1.88-1.86 (m, 1H), 1.74-1.59 (m, 4H). HPLC: (max plot) 99%; (254 nm) 99%; Rt 3.71 min. LC/MS: 454.2 (M+1).

Example 41: 2-[3-(1-Methyl-1H-pyrazol-4-yl)-phenyl]-5-{1-[(S)-1-(3-methyl-tetrahydro-pyran-4-yl)-piperidin-3-yl]-1H-pyrazol-4-yl}-pyrimidine (39)

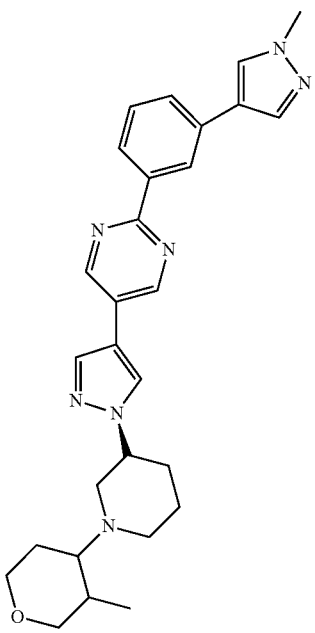

Step 1: (S)-3-(4-Bromo-pyrazol-1-yl)-piperidine-1-carboxylic acid tert-butyl ester

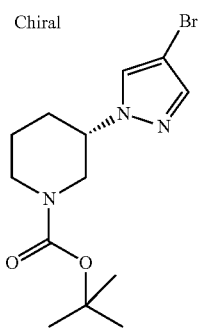 [SMILES: CC(C)(C)OC(=O)N1CCC[C@H](n2cc(Br)cn2)C1]

Diisopropyl azodicarboxylate (5.97 g; 28.92 mmol; 1.20 eq.) was added drop wise to a solution of (R)-3-Hydroxy-piperidine-1-carboxylic acid tert-butyl ester (5.00 g; 24.10 mmol; 1.00 eq.), 4-Bromo-1H-pyrazole (3.65 g; 24.10 mmol; 1.00) and Triphenylphosphine (7.74 g; 28.92 mmol; 1.20 eq.) in Tetrahydrofuran (25.00 mL) maintained at 0° C. The reaction mixture was allowed to warm to RT and stirred for 14 h. THF was removed under reduced pressure, the residue was dissolved in water and extracted with ethylacetate (2×200 mL). The combined organic layers were dried over anhydrous Na$_2$SO$_4$, filtrated and concentrated to give the title compound as a yellow liquid (2 g, 10%). LC/MS: 230 (boc cleaved mass).

Step 2: (S)-3-(4-Bromo-pyrazol-1-yl)-piperidine hydrochloride

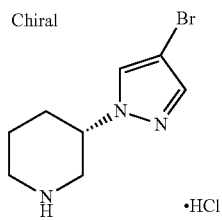 [SMILES: Brc1cnn([C@H]2CCCNC2)c1 ; Cl]

A solution of HCl in 1,4-dioxane (4N, 0.30 mL; 1.21 mmol; 10.00 eq.) was added to a solution of (S)-3-(4-Bromo-pyrazol-1-yl)-piperidine-1-carboxylic acid tert-butyl ester (2.1 g, 3.8 mmol, 1.0 eq.) in dioxane (21 mL) maintained at 0° C. under nitrogen atmosphere. The reaction mixture was allowed to warm to RT and stirred for 18 h. Dioxane was removed under reduced pressure to afford the title compound as a yellow liquid. LC/MS: 230.0 (M+1).

Step 3: 2-[3-(1-Methyl-1H-pyrazol-4-yl)-phenyl]-5-((S)-1-piperidin-3-yl-1H-pyrazol-4-yl)-pyrimidine

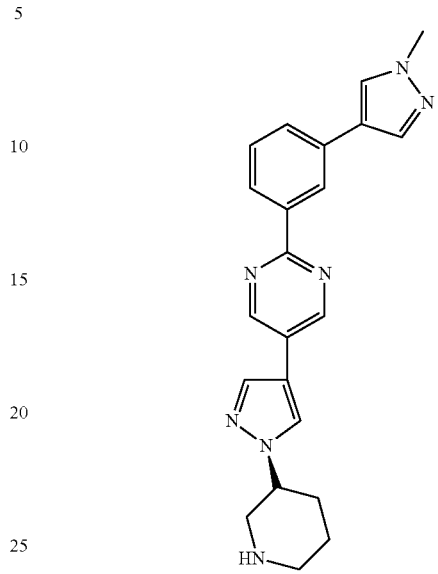

The title compound was obtained following the procedure described for example 14 step 3, but starting from (S)-3-(4-Bromo-pyrazol-1-yl)-piperidine (1.00 g; 1.44 mmol; 1.00 eq.) as a brown solid (200 mg; 34.3%). LC/MS: (max plot) 95%; (254 nm) 97%; Rt 2.87 min; 386.2 (M+1).

Step 4: 2-[3-(1-Methyl-1H-pyrazol-4-yl)-phenyl]-5-{1-[(S)-1-(3-methyl-tetrahydro-pyran-4-yl)-piperidin-3-yl]-1H-pyrazol-4-yl}-pyrimidine Titanium(4)isopropoxide (161 mg; 0.56 mmol; 1.50 eq.) was added to a stirred suspension of 2-[3-(1-Methyl-1H-pyrazol-4-yl)-phenyl]-5-((S)-1-piperidin-3-yl-1H-pyrazol-4-yl)-pyrimidine (150 mg; 0.37 mmol; 1.00 eq.), 3-Methyl-tetrahydro-pyran-4-one (51 mg; 0.45 mmol; 1.20 eq.) and TEA (260 uL; 1.86 mmol; 5.00 eq.) in Toluene (7.50 mL) maintained at 0° C. under N$_2$ atmosphere. The reaction mixture was then heated at reflux overnight. It was cooled to 0° C. be fore the addition of Sodium cyanoborohydride (49 mg; 0.74 mmol; 2.00 eq.) and stirred at RT for another 12 h. Toluene was removed under reduced pressure, water was added to the residue and the mixture was extracted with ethyl acetate (2×30 mL). The combined organic layers were washed with brine, dried over anhydrous Na2SO4, filtrated and concentrated. Purification by preparative HPLC afforded the title compound as a white solid (20 mg, 11%). 1H NMR (MeOD; 400 MHz) δ 9.09 (s, 2H), 8.60 (s, 1H), 8.43 (s, 1H), 8.27 (d, J=7.8 Hz, 1H), 8.13 (s, 1H), 8.06 (s, 1H), 7.91 (s, 1H), 7.70 (d, J=7.8 Hz, 1H), 7.51 (t, J=7.8 Hz, 1H), 4.88 (s, 1H), 4.68-4.11 (m, 3H), 3.97 (s, 3H), 3.86-3.60 (m, 2H), 3.57-3.49 (m, 2H), 3.32-3.31 (m, 1H), 2.50-2.29 (m, 4H), 2.10-1.94 (m, 4H), 1.32-1.17 (m, 3H). HPLC: (max plot) 97%; (254 nm) 95%; Rt 3.07 min. LC/MS: 484.2 (M+1).

Example 42: 2-[3-(1-Methyl-1H-pyrazol-4-yl)-phenyl]-5-{1-[(R)-1-(3-methyl-tetrahydro-pyran-4-yl)-piperidin-3-yl]-1H-pyrazol-4-yl}-pyrimidine (40)

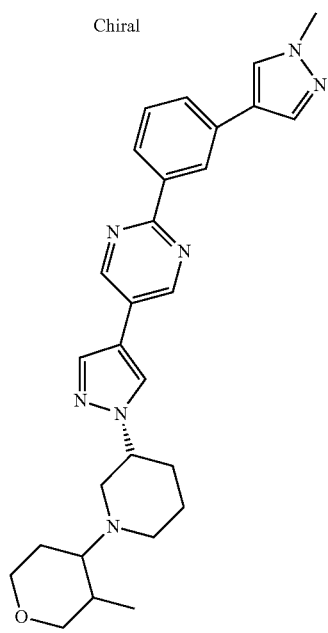

Step 1: (R)-3-(4-Bromo-pyrazol-1-yl)-piperidine-1-carboxylic acid tert-butyl ester

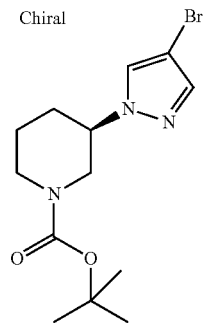 [SMILES: CC(C)(C)OC(=O)N1CCC[C@@H](n2cc(Br)cn2)C1]

The title compound was obtained following the procedure described for example 41, step 1 but starting from (S)-3-Hydroxy-piperidine-1-carboxylic acid tert-butyl ester (5.00 g; 24.10 mmol; 1.00 eq.) as a yellow gum (4 g, 13%). LC/MS: 230 (t-butyl ester cleaved mass).

Step 2: (R)-3-(4-Bromo-pyrazol-1-yl)-piperidine hydrochloride

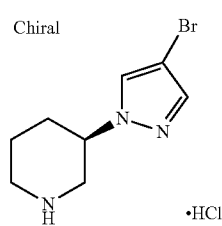 [SMILES: Brc1cnn([C@@H]2CCCNC2)c1 ; Cl]

The title compound was obtained following the procedure described for example 10, step 2 but starting from (R)-3-(4-Bromo-pyrazol-1-yl)-piperidine-1-carboxylic acid tert-butyl ester (4.77 g; 14.46 mmol; 1.00 eq.) as a yellow gum (4 g, 30%). LC/MS: 230.0 (M+1).

Step 3: 2-[3-(1-Methyl-1H-pyrazol-4-yl)-phenyl]-5-((R)-1-piperidin-3-yl-1H-pyrazol-4-yl)-pyrimidine

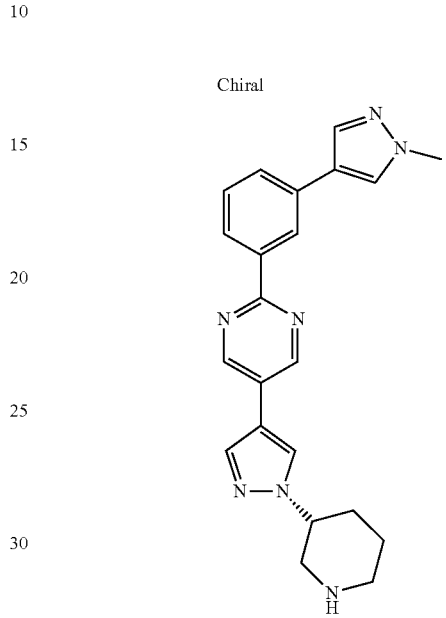

The title compound was obtained following the procedure described for example 14, step 3 but starting from (R)-3-(4-Bromo-pyrazol-1-yl)-piperidine (4.10 g; 4.29 mmol; 1.00 eq.) as a brown solid (260 mg, 15%). LC/MS: (max plot) 93%; (254 nm) 93%; Rt 4.63 min; 386.2 (M+1).

Step 4: 2-[3-(1-Methyl-1H-pyrazol-4-yl)-phenyl]-5-{1-[(R)-1-(3-methyl-tetrahydro-pyran-4-yl)-piperidin-3-yl]-1H-pyrazol-4-yl}-pyrimidine The title compound was obtained following the procedure described for example 41, step 4 but starting from 2-[3-(1-Methyl-1H-pyrazol-4-yl)-phenyl]-5-((R)-1-piperidin-3-yl-1H-pyrazol-4-yl)-pyrimidine (150 mg; 0.36 mmol; 1.00 eq.) as a yellow solid (25 mg, 13%). 1H NMR (DMSO; 400 MHz) δ 9.19 (s, 2H), 8.59-8.57 (m, 1H), 8.53 (s, 1H), 8.25-8.21 (m, 3H), 7.91-0.00 (m, 1H), 7.71 (d, J=7.7 Hz, 1H), 7.51 (t, J=7.8 Hz, 1H), 4.69-0.00 (m, 1H), 4.70-4.69 (m, 1H), 4.10-3.90 (m, 1H), 3.89 (s, 3H), 3.73-3.66 (m, 4H), 3.50-3.44 (m, 2H), 3.42-3.26 (m, 3H), 3.16-2.90 (m, 1H), 2.23-2.08 (m, 2H), 1.90-1.79 (m, 5H), 1.09-1.08 (m, 3H). HPLC: (max plot) 92%; (254 nm) 89%; Rt 3.06 min. LC/MS: 484.2 (M+1).

Example 43: Lithium 3-(4-{2-[3-(1-Methyl-1H-pyrazol-4-yl)-phenyl]-pyrimidin-5-yl}-pyrazol-1-yl)-cyclohexanecarboxylate (41)

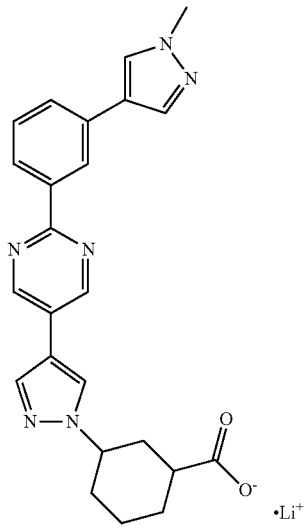 [SMILES: Cn1cc(-c2cccc(-c3ncc(-c4cnn(C5CCCC(C(=O)[O-])C5)c4)cn3)c2)cn1 ; [Li+]]

Step 1: 3-(N'-tert-Butoxycarbonyl-hydrazino)-cyclohexanecarboxylic acid methyl ester

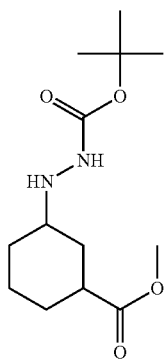 [SMILES: COC(=O)C1CCCC(NNC(=O)OC(C)(C)C)C1]

The title compound was obtained following the procedure described for example 21, step 3 but starting from 3-Oxo-cyclohexanecarboxylic acid methyl ester (3.00 g; 18.82 mmol; 1.00 eq.) as a colorless gum (5 g, 80%). LC/MS: (max plot) 82%; Rt 2.85 min; 273.0 (M+1)

Step 2: 3-(3-Bromo-pyrazol-1-yl)-cyclohexanecarboxylic acid methyl ester

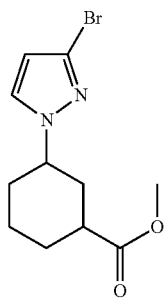 [SMILES: COC(=O)C1CCCC(n2ccc(Br)n2)C1]

The title compound was obtained following the procedure described for example 21, step 4 but starting from 3-(N'-tert-Butoxycarbonyl-hydrazino)-cyclohexanecarboxylic acid methyl ester (5.0 g; 15.05 mmol; 1.00 eq.) as a yellow oil. LC/MS: 287.0 (M+1).

Step 3: 3-(4-{2-[3-(1-Methyl-1H-pyrazol-4-yl)-phenyl]-pyrimidin-5-yl}-pyrazol-1-yl)-cyclohexanecarboxylic acid methyl ester

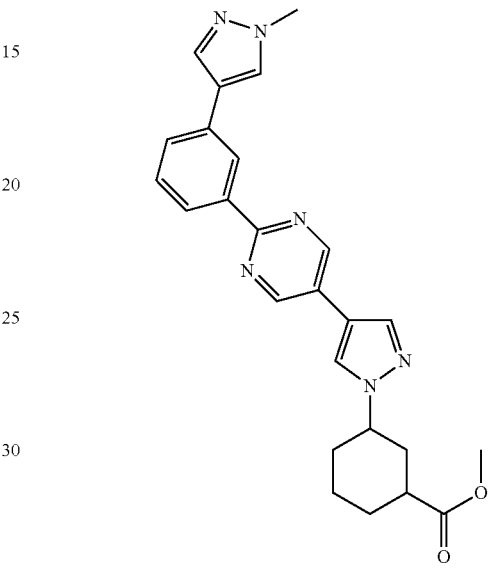

The title compound was obtained following the procedure described for example 14, step 3 but starting from 3-(3-Bromo-pyrazol-1-yl)-cyclohexanecarboxylic acid methyl ester (500 mg; 0.47 mmol; 1.00 eq.) as a brown solid (350 mg, 29%). LC/MS: 443.0 (M+1).

Step 4: Lithium 3-(4-{2-[3-(1-Methyl-1H-pyrazol-4-yl)-phenyl]-pyrimidin-5-yl}-pyrazol-1-yl)-cyclohexanecarboxylate A solution of 3-(4-{2-[3-(1-Methyl-1H-pyrazol-4-yl)-phenyl]-pyrimidin-5-yl}-pyrazol-1-yl)-cyclohexanecarboxylic acid methyl ester (400 mg; 0.21 mmol; 1.00 eq.) and Lithium Hydroxide Monohydrate (200 mg; 4.72 mmol; 23 eq.) in THF (8.00 mL)/Water (1.60 mL)/Methanol (8.00 mL) was stirred at room temperature for 1 h. The reaction mixture was then diluted with water (20 mL) and washed with ethyl acetate (2×20 mL). Aqueous layer was concentrated under reduced pressure and azotroped with toluene (4*20 mL) to afford the title compound as a brown solid (85 94.4%). 1H NMR (DMSO; 400 MHz) δ 12.50 (s, 1H), 9.16 (d, J=2.68 Hz, 2H), 8.55-8.52 (m, 2H), 8.26 (s, 1H), 8.21 (d, J=7.92 Hz, 1H), 8.13 (s, 1H), 7.92 (s, 1H), 7.71-7.69 (m, 1H), 7.50 (t, J=7.72 Hz, 1H), 4.44-4.43 (m, 1H), 3.88 (s, 3H), 3.32-2.83 (m, 1H), 2.50-2.32 (m, 1H), 2.32-1.98 (m, 4H), 1.92-1.79 (m, 1H), 1.73-1.48 (m, 2H), 1.18-1.15 (m, 1H). HPLC: (max plot) 99%; (Mixture of isomers 23: 76); (254 nm) 98%; Rt 3.7, 3.8 min; LC/MS: 429.2 (M+1).

Example 44: 3-(4-{2-[3-(1-Methyl-1H-pyrazol-4-yl)-phenyl]-pyrimidin-5-yl}-pyrazol-1-yl)-cyclopentanecarboxylic acid (42)

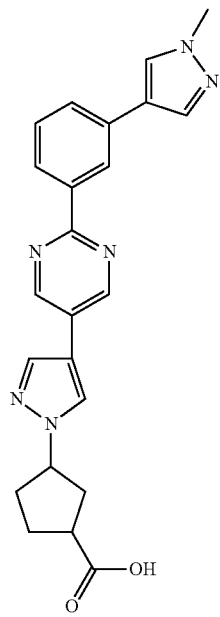 [SMILES: Cn1cc(-c2cccc(-c3ncc(-c4cnn(C5CCC(C(=O)O)C5)c4)cn3)c2)cn1]

The title compound was obtained following the procedure described for example 43, but starting from 3-Oxo-cyclopentanecarboxylic acid methyl ester. Reaction mixture after the saponification step was acidified to pH 2, affording the parent compound as a white solid (120 mg, 47%). 1H NMR (DMSO; 400 MHz) δ 12.24 (brs, 1H), 9.16 (s, 2H), 8.52 (s, 2H), 8.26 (s, 1H), 8.21 (d, J=7.96 Hz, 1H), 8.14 (s, 1H), 7.91 (s, 1H), 7.70 (d, J=7.84 Hz, 1H), 7.51 (t, J=7.76 Hz, 1H), 4.79-4.75 (m, 1H), 3.89 (s, 3H), 3.08-2.89 (m, 1H), 2.35-2.11 (m, 3H), 2.06-1.97 (m, 3H). HPLC: (max plot) 98%; (254 nm) 98%; Rt 3.71 min. LC/MS: 415.0 (M+1).

Example 45: 1-Methyl-8-((S)-4-{2-[3-(2-methyl-2H-pyrazol-3-yl)-phenyl]-pyrimidin-5-yl}-pyrazol-1-yl)-1-aza-spiro[4.5]decan-2-one (43)

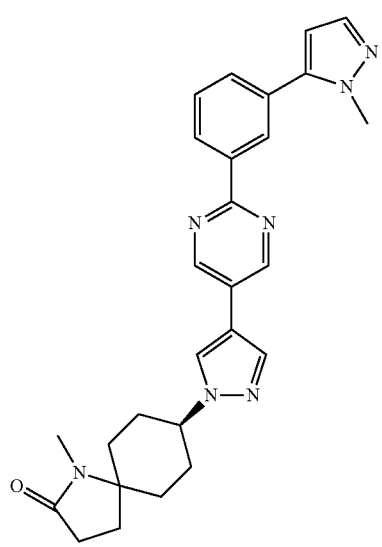

Step 1: 1-Methyl-5-[3-(4,4,5,5-tetramethyl-[1,3,2]dioxaborolan-2-yl)-phenyl]-1H-pyrazole

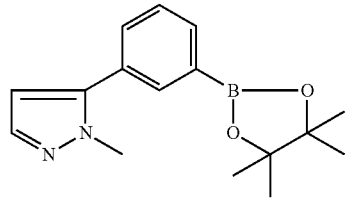 [SMILES: Cn1nccc1-c1cccc(B2OC(C)(C)C(C)(C)O2)c1]

The title compound was obtained following the procedure described for example 33, step 2, but starting from 5-(3-Bromo-phenyl)-1-methyl-1H-pyrazole (2.10 g; 8.73 mmol; 1.00 eq.) as a yellow liquid (1 g, 43%). LC/MS: 285.2 (M+1).

Step 2: 5-Bromo-2-[3-(2-methyl-2H-pyrazol-3-yl)-phenyl]-pyrimidine

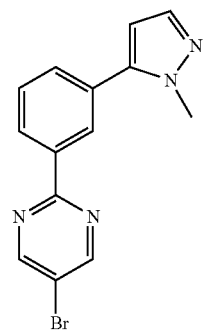 [SMILES: Cn1nccc1-c1cccc(-c2ncc(Br)cn2)c1]

The title compound was obtained following the procedure described for example 33, step 3, but starting from 1-Methyl-5-[3-(4,4,5,5-tetramethyl-[1,3,2]dioxaborolan-2-yl)-phenyl]-1H-pyrazole (1.40 g; 3.79 mmol; 1.00 eq.) as a yellow solid (1 g, 62%). LC/MS: (max plot) 93%; (254 nm) 95%; Rt 4.29 min; 317.0 (M+1).

Step 3: 2-[3-(2-Methyl-2H-pyrazol-3-yl)-phenyl]-5-(4,4,5,5-tetramethyl-[1,3,2]dioxaborolan-2-yl)-pyrimidine

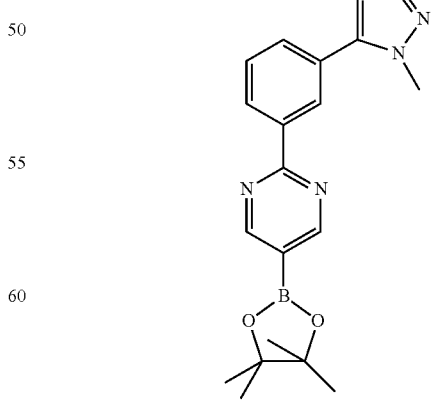

The title compound was obtained following the procedure described for example 30, step 4, but starting from 5-Bromo- 2-[3-(2-methyl-2H-pyrazol-3-yl)-phenyl]-pyrimidine (700 mg; 2.22 mmol; 1.00 eq.) as a brown oil (400 mg, 24%). LC/MS: 281 (Boronate ester of m/z 362 is cleaved to boronic acid 281).

Step 4: 1-Methyl-8-(Cis-4-{2-[3-(2-methyl-2H-pyrazol-3-yl)-phenyl]-pyrimidin-5-yl}-pyrazol-1-yl)-1-aza-spiro[4.5]decan-2-one The title compound was obtained following the procedure described for example 14, step 3 but starting from 2-[3-(2-Methyl-2H-pyrazol-3-yl)-phenyl]-5-(4,4,5,5-tetramethyl-[1,3,2]dioxaborolan-2-yl)-pyrimidine (350 mg; 0.47 mmol; 1.00 eq.) and Cis-(4-Bromo-pyrazol-1-yl)-1-methyl-1-aza-spiro[4.5]decan-2-one (148 mg; 0.42 mmol; 0.90 eq.) as a white solid (15 mg, 7%). 1H NMR (DMSO, 400 MHz) δ 9.19 (s, 2H), 8.55 (s, 1H), 8.47 (s, 1H), 8.45 (d, J=7.20 Hz, 1H), 8.14 (s, 1H), 7.67 (d, J=7.60 Hz, 2H), 7.52 (s, 1H), 6.50 (s, 1H), 4.27-4.26 (m, 1H), 3.90 (s, 3H), 2.66 (s, 3H), 2.29-2.25 (m, 2H), 2.09 (s, 2H), 2.00-1.95 (m, 5H), 1.54-1.52 (m, 2H). HPLC: (max plot) 96%; (254 nm) 99%; Rt 3.619 min; LC/MS: 468.0 (M+1).

Example 46: 1-Methyl-8-(4-{2-[3-(1-methyl-1H-pyrazol-3-yl)-phenyl]-pyrimidin-5-yl}-pyrazol-1-yl)-1-aza-spiro[4.5]decan-2-one (44)

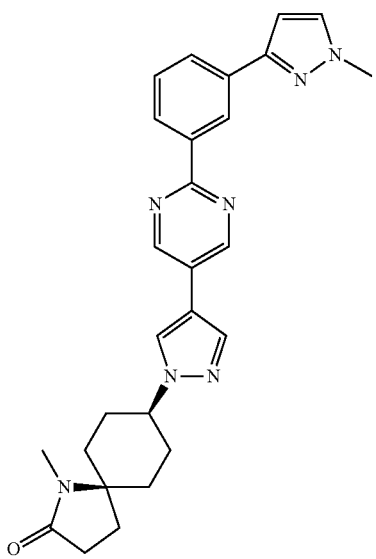 [SMILES: Cn1ccc(-c2cccc(-c3ncc(-c4cnn([C@H]5CC[C@]6(CCC(=O)N6C)CC5)c4)cn3)c2)n1]

Step 1: (E)-1-(3-Bromo-phenyl)-3-dimethylamino-propenone

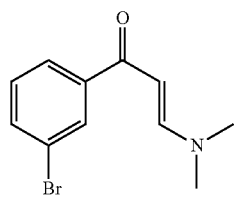

A solution of 1-(3-Bromo-phenyl)-ethanone (15 g; 73.85 mmol; 1.00 eq.) and N,N-dimethylformamide dimethyl acetal (31 mL; 221.56 mmol; 3.00 eq.) in Ethanol (225 mL) was refluxed at 80° for 12 h. The reaction mixture was then concentrated under reduced pressure to get (E)-1-(3-Bromo-phenyl)-3-dimethylamino-propenone (15 g; 42.20 mmol; 57.1%) as a Colourless gum. LC/MS: 256.0 (M+1).

Step 2: 3-(3-Bromo-phenyl)-1H-pyrazole

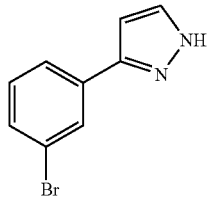 [SMILES: Brc1cccc(-c2cc[nH]n2)c1]

A solution of (E)-1-(3-Bromo-phenyl)-3-dimethylamino-propenone (15 g; 59.03 mmol; 1.00 eq.) and Hydrazine hydrate (5.80 mL; 118.05 mmol; 2.00 eq.) in Ethanol (150.00 mL) was refluxed to 85° C. for 14 h. Ethanol was removed under reduced pressure and the residue was diluted in DCM (50 mL) and washed with water, then brine. The organic layer was dried over Na$_2$SO$_4$, filtered and concentrated to give the title compound as a yellow liquid (17 g, 99%). 1H NMR (DMSO; 400 MHz) δ 13.00 (s, 1H), 7.99-7.97 (m, 1H), 7.82-7.80 (m, 2H), 7.48-7.41 (m, 1H), 7.39-7.33 (m, 1H), 6.79 (d, J=2.20 Hz, 1H). LC/MS: 224.9 (M+1).

Step 3: 3-(3-Bromo-phenyl)-1-methyl-1H-pyrazole

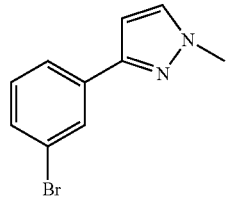

3-(3-Bromo-phenyl)-1H-pyrazole (17 g; 60.97 mmol; 1.00 eq.) dissolved in THF (5 mL) was added dropwise to a suspension of Sodium hydride (2.44 g; 60.97 mmol; 1.00 eq.) in THF (500 mL) maintained at 0° C. The reaction mixture was stirred for 30 min before the dropwise addition of Iodomethane (8.03 mL; 122 mmol; 2.00 eq.). It was then allowed to warm to RT and stirred for another 4 h. Ice was added to quench the reaction and the mixture was extracted with ethyl acetate (30 mL×2). Combined organic layers were dried over anhydrous sodium sulfate, filtered and concentrated to give the title compound as a brown liquid (14.5 g, 99%). LC/MS: (max plot) 99%; (254 nm) 99%; Rt 4.1 min; 239.0 (M+1).

Step 4: 1-Methyl-3-[3-(4,4,5,5-tetramethyl-[1,3,2]dioxaborolan-2-yl)-phenyl]-1H-pyrazole

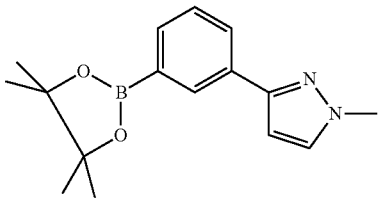

The title compound was obtained following the procedure described for example 33, step 2, but starting from 3-(3-Bromo-phenyl)-1-methyl-1H-pyrazole (3.50 g; 14.54 mmol; 1.00 eq.) in DMF (70 mL) as a yellow solid (3 g, 71%). LC/MS: 285 (M+1).

Step 5: 5-Bromo-2-[3-(1-methyl-1H-pyrazol-3-yl)-phenyl]-pyrimidine

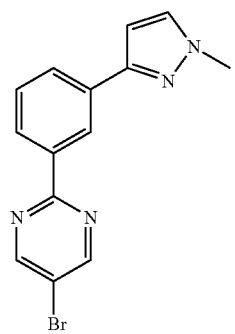 [SMILES: Cn1ccc(-c2cccc(-c3ncc(Br)cn3)c2)n1]

The title compound was obtained following the procedure described for example 33, step 3, but starting from 1-Methyl-3-[3-(4,4,5,5-tetramethyl-[1,3,2]dioxaborolan-2-yl)-phenyl]-1H-pyrazole (1.00 g; 3.42 mmol; 1.00 eq.) as a yellow solid (700 mg, 62%). LC/MS: (max plot) 95%; (254 nm) 95%; Rt 4.353 min; 317.0 (M+1).

Step 6: 2-[3-(1-Methyl-1H-pyrazol-3-yl)-phenyl]-5-(4,4,5,5-tetramethyl-[1,3,2]dioxaborolan-2-yl)-pyrimidine The title compound was obtained following the procedure described for example 33, step 4, but starting from 5-Bromo-2-[3-(1-methyl-1H-pyrazol-3-yl)-phenyl]-pyrimidine (700 mg; 2.11 mmol; 1.00 eq.) as an oil (400 mg, 35%). LC/MS: 281 (Boronic ester mass of 362 is cleaved to boronic acid m/z 280).

Step 7: 1-Methyl-8-(4-{2-[3-(1-methyl-1H-pyrazol-3-yl)-phenyl]-pyrimidin-5-yl}-pyrazol-1-yl)-1-aza-spiro[4.5]decan-2-one The title compound was obtained following the procedure described for example 14, step 3 but starting from 2-[3-(1-Methyl-1H-pyrazol-3-yl)-phenyl]-5-(4,4,5,5-tetramethyl-[1,3,2]dioxaborolan-2-yl)-pyrimidine (200 mg; 0.37 mmol; 1.00 eq.) and Cis-8-(4-Bromo-pyrazol-1-yl)-1-methyl-1-aza-spiro[4.5]decan-2-one (118 mg; 0.34 mmol; 0.90 eq.) as a white solid (15 mg, 8%). 1H NMR (DMSO, 400 MHz) δ 9.17 (s, 2H), 8.85 (s, 1H), 8.54 (s, 1H), 8.30 (d, J=8.00 Hz, 1H), 8.14 (s, 1H), 7.90 (d, J=8.00 Hz, 1H), 7.78 (s, 1H), 7.54 (t, J=7.60 Hz, 1H), 6.76 (s, 1H), 4.28-4.14 (m, 1H), 3.92 (s, 3H), 2.67 (s, 3H), 2.29-2.25 (m, 2H), 2.09-2.03 (m, 2H), 2.00-1.92 (m, 5H), 1.54-1.52 (m, 2H). HPLC: (max plot) 97%; (254 nm) 93%; Rt 3.66 min. LC/MS: 468.0 (M+1).

Example 47: (E)-4-Dimethylamino-1-[4-(4-{2-[3-(1-methyl-1H-pyrazol-4-yl)-phenyl]-pyrimidin-5-yl}-pyrazol-1-yl)-piperidin-1-yl]-but-2-en-1-one (47)

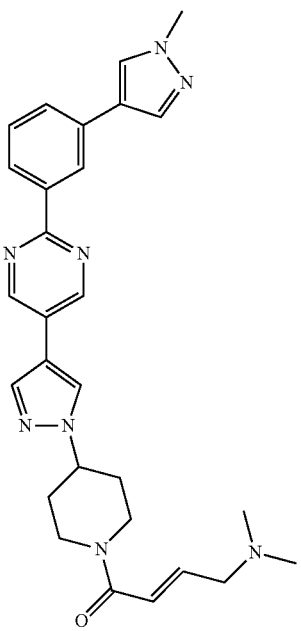 [SMILES: CN(C)C/C=C/C(=O)N1CCC(n2cc(-c3cnc(-c4cccc(-c5cnn(C)c5)c4)nc3)cn2)CC1]

T3P (177 µl; 0.30 mmol; 1.50 eq.) was added to a solution of 2-[3-(1-Methyl-1H-pyrazol-4-yl)-phenyl]-5-(1-piperidin-4-yl-1H-pyrazol-4-yl)-pyrimidine hydrochloride (99 mg; 0.20 mmol; 1.00 eq.) and DIEA (142 µl; 0.80 mmol; 4.00 eq.) in DCM (2.00 mL) and DMF (2 mL). The reaction mixture was stirred at RT for 10 min. It was concentrated and directly purified by preparative HPLC (C-18 (10 um), 30×150 mm, 0.1% HCO2H modified mobile phases (A=water, B=ACN), Method 15% ACN isocratic for 1 min then ramp to 60% ACN over 10 min at 60 mL/min) to give the title compound as a white powder (58 mg, 58%). $^1$H NMR (400 MHz, DMSO-d6) δ 9.16 (s, 2H), 8.60 (d, 2H), 8.26 (s, 1H), 8.22 (d, 1H), 8.15 (s, 1H), 7.92 (s, 1H), 7.71 (d, 1H), 7.52 (t, 1H), 6.75-6.58 (m, 2H), 4.55 (m, 1H), 4.20 (m, 1H), 3.90 (s, 3H), 3.11 (d, 2H), 2.86 (m, 1H), 2.21 (s, 6H), 2.14 (m, 2H), 1.84 (m, 2H), 1.63-1.42 (m, 1H), 1.06-0.88 (m, 1H). HPLC: (254 nm) 98.5%; Rt 2.99 min. LC/MS: 497.0 (M+1).

Example 48: 1-[4-(4-{2-[3-(1-Methyl-1H-pyrazol-4-yl)-phenyl]-pyrimidin-5-yl}-pyrazol-1-yl)-piperidin-1-yl]-but-2-yn-1-one (48)

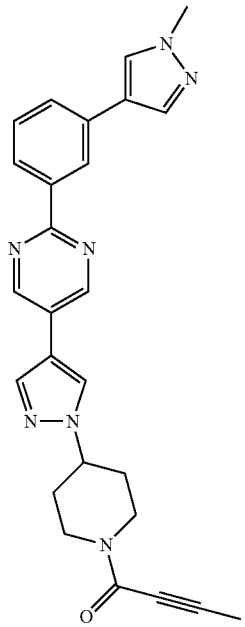 [SMILES: CC#CC(=O)N1CCC(n2cc(-c3cnc(-c4cccc(-c5cnn(C)c5)c4)nc3)cn2)CC1]

A mixture of 2-[3-(1-Methyl-1H-pyrazol-4-yl)-phenyl]-5-(1-piperidin-4-yl-1H-pyrazol-4-yl)-pyrimidine hydrochloride (51 mg; 0.10 mmol; 1.00 eq.), DIPEA (66.88 µl; 0.38 mmol; 4.00 eq.), 2-butynoic acid (8.88 mg; 0.11 mmol; 1.10 eq.) and pybop (60 mg; 0.12 mmol; 1.20 eq.) in DMA (2.0 mL) was stirred at RT for 30 min. The stirring reaction was then slowly treated with 15 mL of water. The resulting suspension was stirred for 1 hr and then filtered. The solid was washed with water (3×3 mL) and dried overnight to afford the title compound as a white solid (40 mg, 92%). $^1$H NMR (400 MHz, DMSO-d6) δ 9.16 (s, 2H), 8.61-8.51 (d, 2H), 8.26 (s, 1H), 8.25 (d, 1H), 8.16 (s, 1H), 7.92 (s, 1H), 7.72 (d, 1H), 7.52 (t, 1H), 4.63-4.48 (m, 1H), 4.40 (t, 2H), 3.90 (s, 3H), 3.43-3.33 (m, 1H), 2.98 (t, 1H), 2.25-2.09 (m, 2H), 2.06 (s, 3H), 1.86 (m, 2H). HPLC: (254 nm) 99.0%; Rt 3.78 min. LC/MS: 452.0 (M+1).

Example 49: Enzymatic Assays

IRAK1 Enzymatic Assay

IRAK1 is a human purified recombinant enzyme (His-TEV-IRAK1 (194-712)). In this assay, IRAK-1 hydrolyses ATP and autophosphorylates. Measurement of IRAK-1 inhibition was performed in streptavidin coated 384 well Flash-Plate (PerkinElmer #SMP410A).

His-TEV-IRAK-1 (15 ng/well), ATP (1 µM, [33P]ATP 0.25 µCi/well) and compounds in DMSO (range of concentrations from 20 µM to 1 nM) or controls (2% DMSO) were incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction was stopped by addition of EDTA. Supernatant was discarded, plates were washed three times with 150 mM NaCl and radioactivity was then measured in a Microbeta Trilux reader.

IRAK4 Enzymatic Assay

IRAK4 is a human purified recombinant enzyme (His-TEV-IRAK1 (194-712)). IRAK4 hydrolyses ATP, autophosphorylates and phosphorylates a Serine/Threonine generic peptidic substrate (STK: 61 ST1BLC from CisBio International based in Bagnols/Cèze FR).

Measurement of IRAK-4 inhibition was performed in streptavidin coated 384 well FlashPlate (PerkinElmer #SMP410A). His-TEV-IRAK4 (20 ng/well), ATP (2 µM, [$^{33}$P]ATP 0.25 µCi/well), STK1-biotin peptide (300 nM) and compounds in DMSO (range of concentrations from 20 µM to 1 nM) or controls (2% DMSO) were incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction was stopped by addition of EDTA. Supernatant was discarded, plates were washed three times with 150 mM NaCl and radioactivity was then measured in a Microbeta Trilux reader.

TLR7 Induced IL-6 in Human PBMC's

Human PBMC assay was used as one of the functional assays to monitor the activity of IRAK1 and IRAK4 small molecule inhibitors on TLR7 induced IL-6 secretion in human mononuclear cells (PBMC's). Human PBMCs were prepared from buffy coats (whole blood enriched with leukocytes and platelets) obtained from healthy volunteers used either fresh or frozen are plated in assay media (RPMI+ 2% P/S/L-glu+10% HI-FBS) and pre-treated with compounds in DMSO/media (range of concentrations from 25 uM to 0.4 nM) or controls (0.25% DMSO) for 30 minutes at 37° C. in assay media. Following pre-treatment with IRAK1 and IRAK4 inhibitors, PBMC's were stimulated with TLR7 specific ligand (2 uM) overnight (16-18 hrs) at 37° C. After incubation supernatant was transferred to 384 well PE AlphaPlate-384 (6005350) and IL-6 is quantified using Perkin Elmer IL-6 Alpha LISA kit (AL223C). Plates were read on an Envision® plate reader with Alpha Technology®.

Results are given in the following table:

| Compound | IRAK1 IC$_{50}$ | IRAK4 IC$_{50}$ | TLR7 induced IL-6 secretion in hPBMC's (IC50) |
|---|---|---|---|
| 1 | ** | *** | — |
| 2 | ** | *** | * |
| 3 | ** | *** | ** |
| 4 | ** | *** | ** |
| 5 | ** | ** | — |
| 6 | ** | ** | — |
| 7 | ** | ** | — |
| 8 | ** | ** | — |
| 9 | *** | *** | * |
| 10 | ** | *** | ** |
| 11 | ** | *** | ** |
| 12 | *** | *** | ** |
| 13 | ** | ** | — |
| 14 | ** | *** | ** |
| 15 | *** | *** | *** |
| 16 | ** | ** | — |
| 17 | *** | *** | *** |
| 18 | *** | *** | *** |
| 19 | *** | *** | — |
| 20 | ** | ** | — |
| 21 | *** | *** | — |
| 22 | ** | *** | — |
| 23 | ** | *** | — |
| 24 | ** | *** | — |
| 25 | ** | *** | — |
| 26 | ** | ** | * |
| 27 | ** | *** | ** |
| 28 | ** | ** | * |
| 29 | * | ** | — |

-continued

| Compound | IRAK1 IC$_{50}$ | IRAK4 IC$_{50}$ | TLR7 induced IL-6 secretion in hPBMC's (IC50) |
|---|---|---|---|
| 30 | * | ** | — |
| 31 | ** | *** | — |
| 32 | * | ** | — |
| 33 | *** | *** | ** |
| 34 | ** | *** | * |
| 35 | ** | *** | * |
| 36 | *** | *** | ** |
| 37 | *** | *** | ** |
| 38 | ** | *** | ** |
| 39 | ** | ** | — |
| 40 | ** | ** | — |
| 41 | * | ** | * |
| 42 | * | ** | — |
| 43 | * | *** | * |
| 44 | — | *** | — |
| 45 | ** | *** | ** |
| 46 | *** | *** | ** |
| 47 | ** | ** | — |
| 48 | *** | *** | * |

\* IC$_{50}$ ranges from >1 µM-20 µM
\*\* IC$_{50}$ ranges from 0.1 µM-1.0 µM
\*\*\* IC$_{50}$ < 0.1 µM

Example 50: Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of Formula (II):

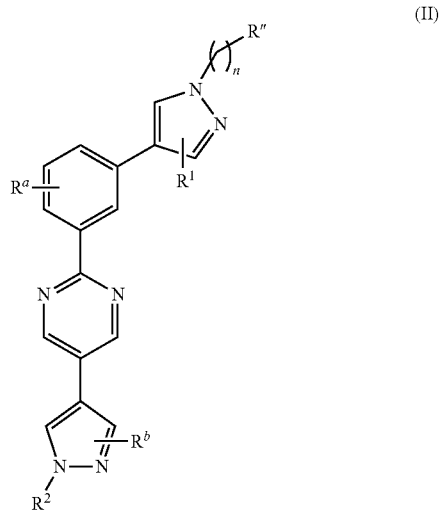

or a pharmaceutically acceptable salt, tautomer or stereoisomer thereof, wherein:

R" is H, C$_{1-6}$ aliphatic, C$_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted;

R$^1$ is absent or R$^1$ is A or Q-R;

R$^a$ is absent or R$^a$ is OR$^3$, CF$_3$, Hal, or NO$_2$;

R$^b$ is absent or R$^b$ is A or COR;

R$^2$ is

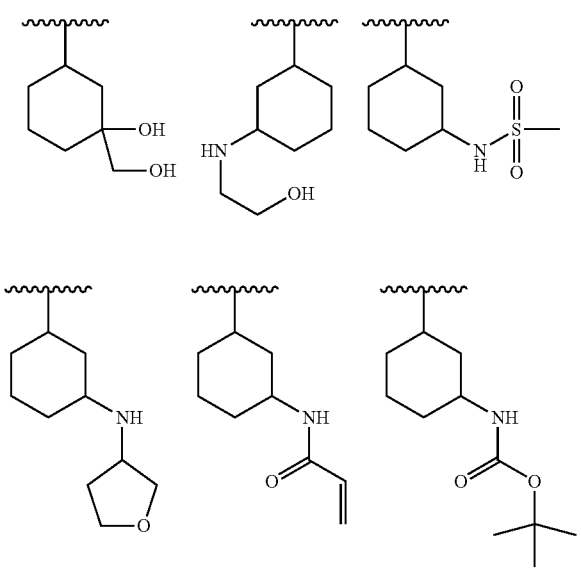

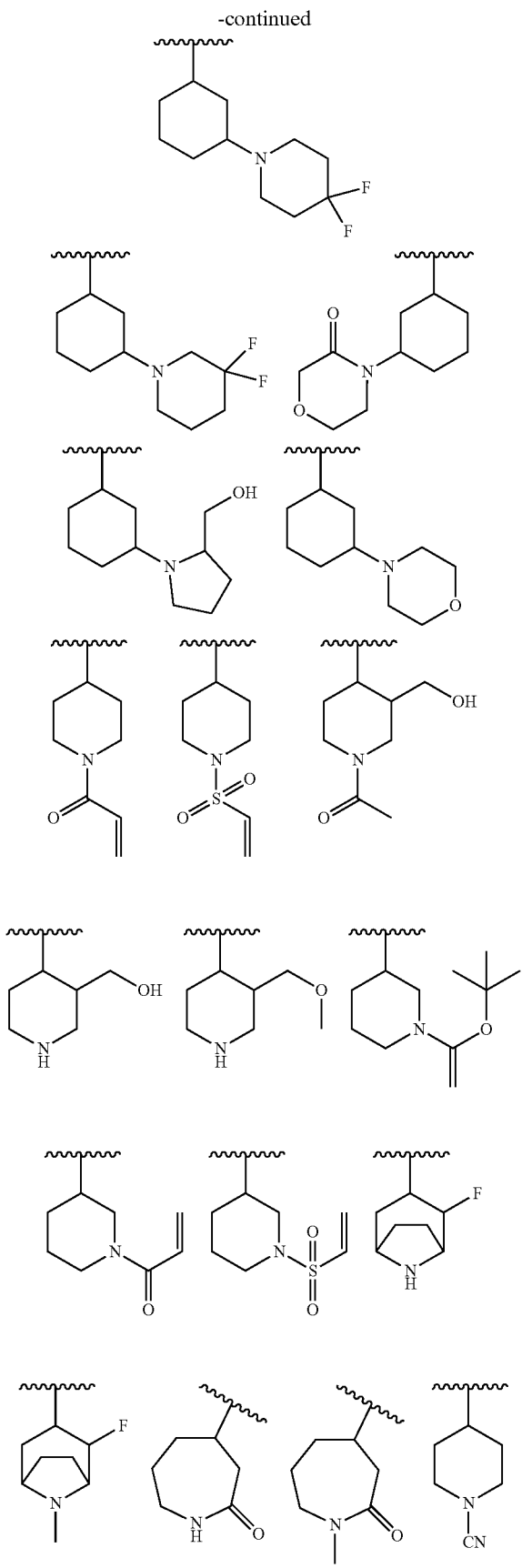

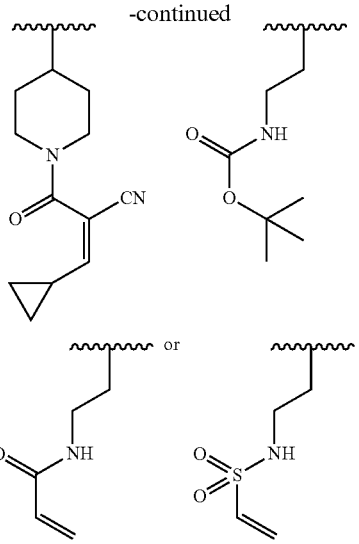

Q is a linear or branched alkylene, having 1 to 6 carbon atoms wherein 1-5 H atoms may be replaced by a group independently selected from $OR^3$, Hal, or $N(R^3)_2$, and wherein 1 or 2 $CH_2$ groups may be replaced by a group independently selected from CO, SO, $SO_2$ and $NR^3$, or Q denotes a 4-8-membered bivalent heterocyclic ring, which is saturated, unsaturated or aromatic and which contains 1 to 3 heteroatoms independently selected from nitrogen, oxygen and sulfur;

each A is independently a linear or branched alkyl having 1 to 10 carbon atoms wherein 1 to 7 H atoms may be replaced by a group independently selected from —$OR^3$, Hal, $NHSO_2A$, $SO_2A$, SOA, or $N(R^3)_2$, and wherein 1, 2 or 3 non-adjacent —$CH_2$— groups may be replaced by a group independently selected from —CO—, $NR^3$ and/or —O—;

each Hal is independently F, Cl, Br or I;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted;

each $R^3$ is H or $C_{1-6}$ alkyl wherein 1 H atom may be replaced by a group selected from OH, —O—$C_{1-6}$ alkyl, and Hal; and n is 0 or 1;

wherein optionally substituted for R" and R means substituted at each substitutable position of the group, and when more than one position is substituted the substituent is the same or different, and the substituent is selected from the group consisting of: deuterium;

halogen; —$(CH_2)_{0-4}R°$; —$(CH_2)_{0-4}OR°$; —$O(CH_2)_{0-4}$ $R°$, —O—$(CH_2)_{0-4}C(O)OR°$; —$(CH_2)_{0-4}CH(OR°)_2$; —$(CH_2)_{0-4}SR°$; —$(CH_2)_{0-4}$Ph which is optionally substituted with $R°$; —$(CH_2)_{0-4}O(CH_2)_{0-1}$Ph which is optionally substituted with $R°$; —CH=CHPh which is optionally substituted with $R°$; —$(CH_2)_{0-4}O(CH_2)_{0-1}$-pyridyl which is optionally substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)$ $NR°_2$; —$N(R°)C(S)NR°_2$; —$(CH_2)_{0-4}N(R°)C(O)OR°$;

—N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched)alkylene)O—N(R°)$_2$; and —(C$_{1-4}$ straight or branched alkylene)C(O)O—N(R°)$_2$; wherein each R° is optionally substituted as defined below and is independently selected from the group consisting of hydrogen, C$_{1-6}$ aliphatic alkyl, —CH$_2$Ph, —O(CH$_2$)$_{0-1}$Ph, —CH$_2$-(5-6 membered heteroaryl ring), and a 5-6-membered saturated, partially unsaturated, or aryl ring having 0-4 heteroatoms independently selected from nitrogen, oxygen, or sulfur, or, optionally, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur;

the optional substituents for R° or a ring formed by two independent occurrences of R° together with their intervening atoms are independently selected from the group consisting of: deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$, wherein each R$^\bullet$ is unsubstituted or where preceded by "halo" is substituted only with one or more halogens, and is independently selected from the group consisting of: C$_{1-4}$ aliphatic alkyl, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur;

or an optional substituent for R°, when on a saturated carbon atom of R°, is a divalent substituent =O or =S.

2. The compound of claim 1, or a pharmaceutically acceptable salt, tautomer or stereoisomer thereof, wherein R$^1$ is absent.

3. The compound of claim 1, or a pharmaceutically acceptable salt, tautomer or stereoisomer thereof, wherein R$^a$ is absent.

4. The compound of claim 1, or a pharmaceutically acceptable salt, tautomer or stereoisomer thereof, wherein R$^b$ is absent.

5. The compound of claim 1, wherein the compound is selected from the group consisting of:

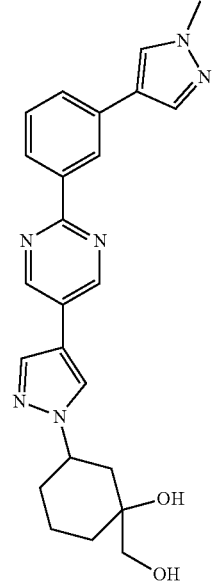

1

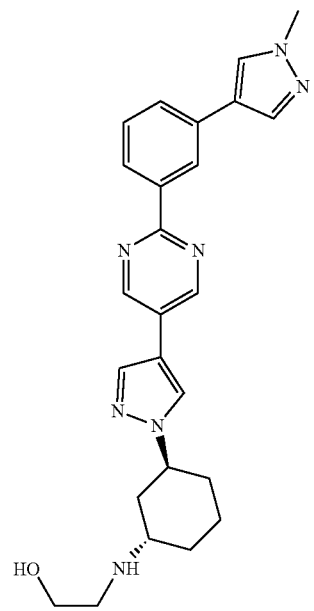

2

143
-continued
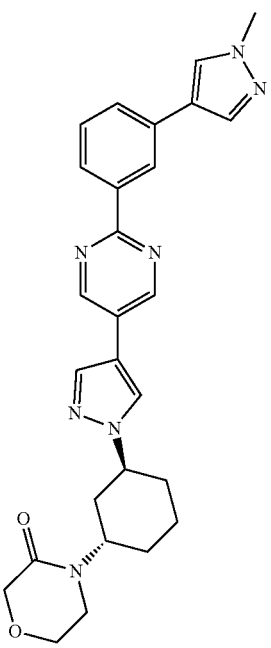
3
144
-continued
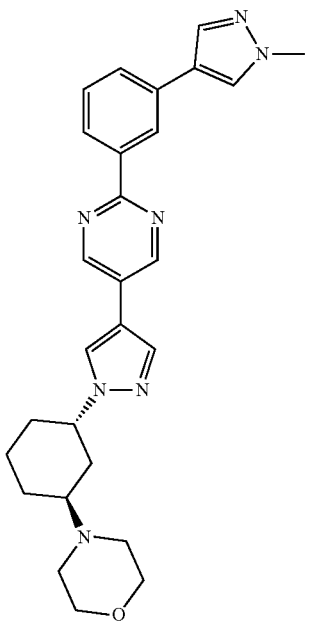
5
4
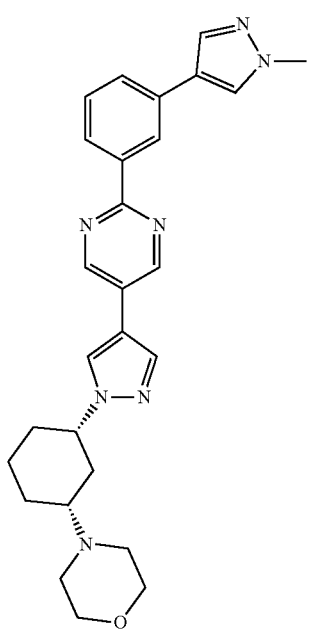
6

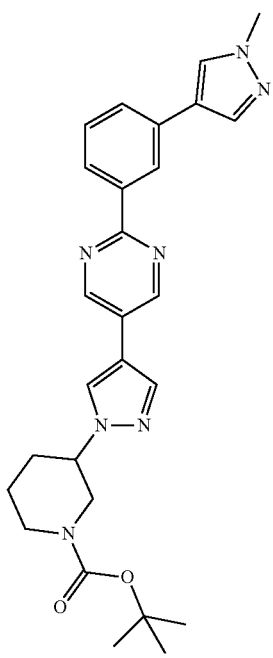
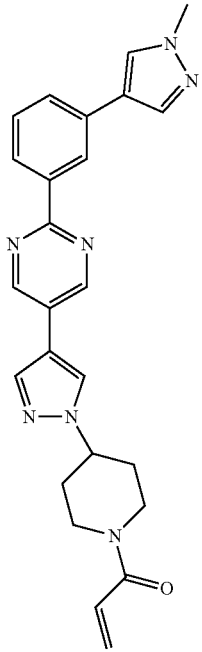
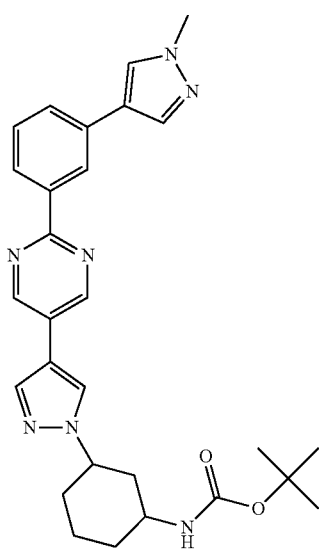
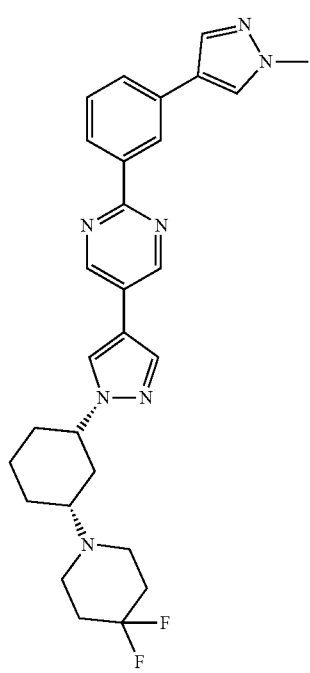

147
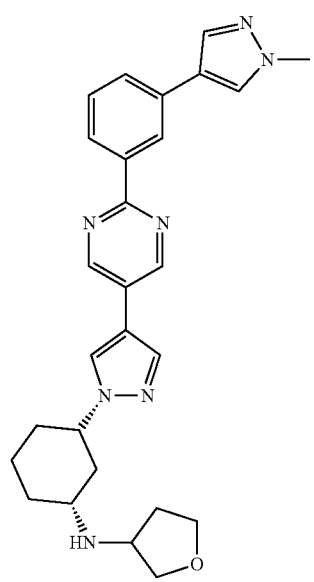
12
148
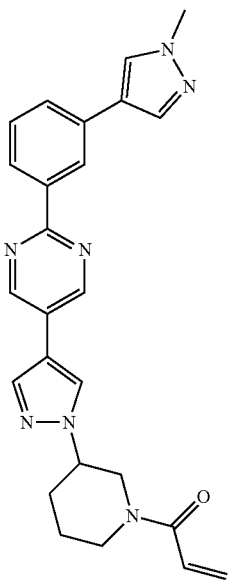
14
13
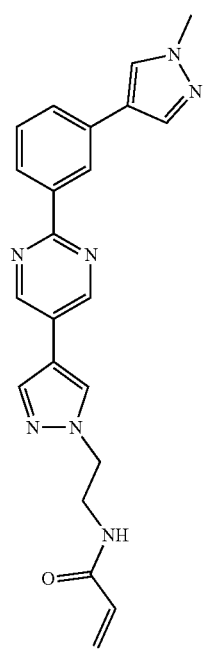
15
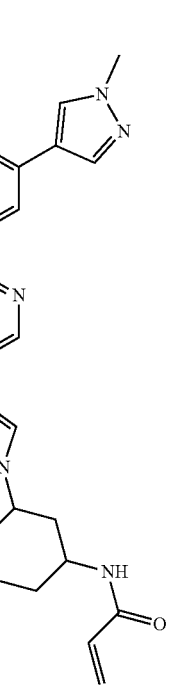

16
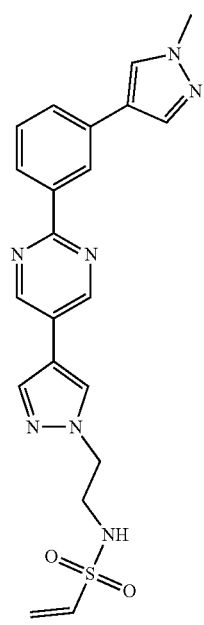
17
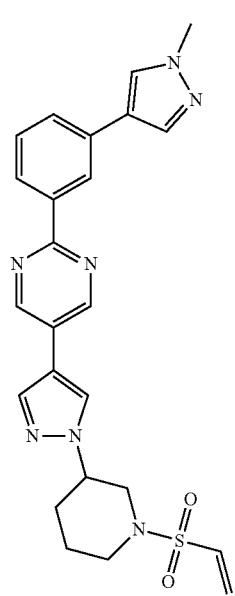
18
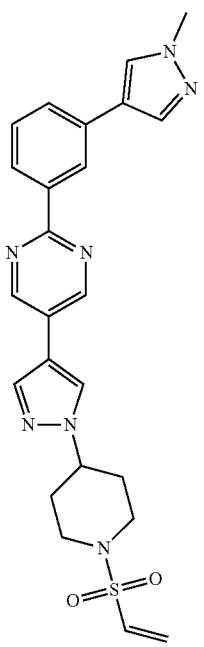
19
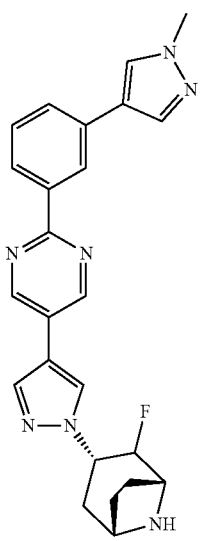

20
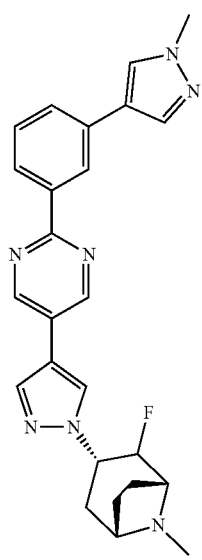
151-continued
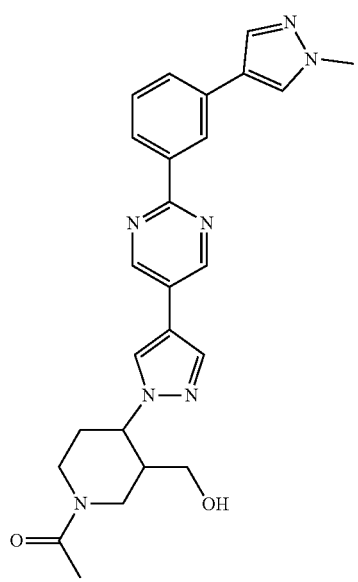
152-continued
21
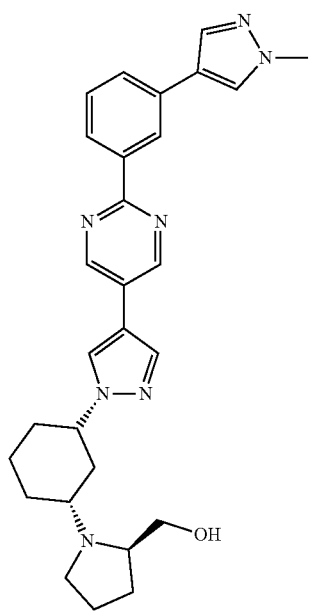
22
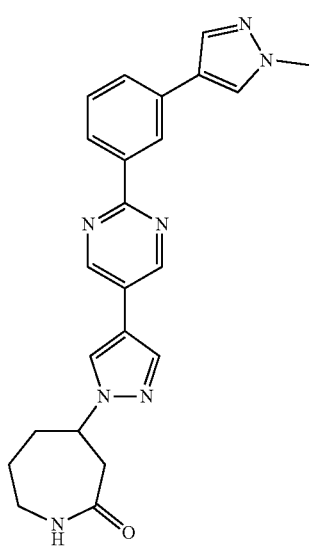
23

153
-continued
24
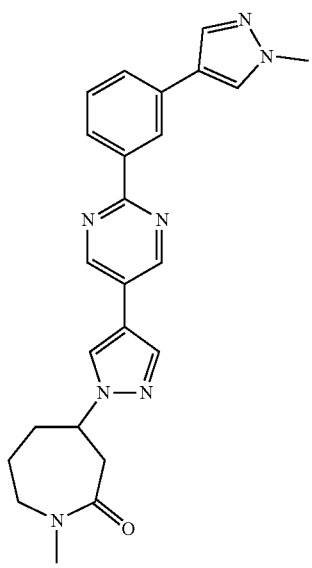
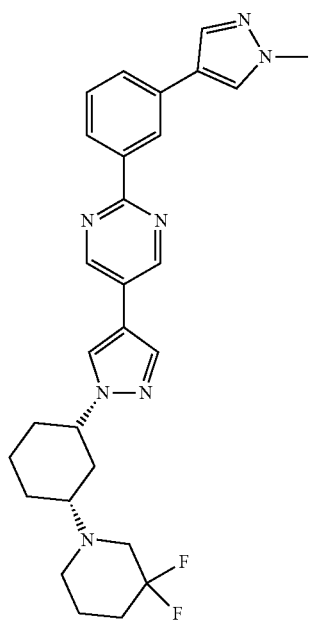
154
-continued
26
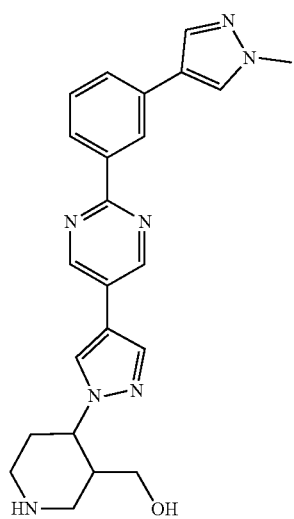
27
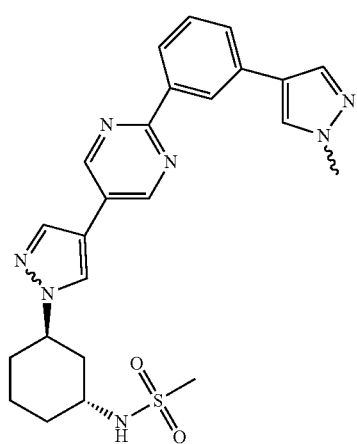
28
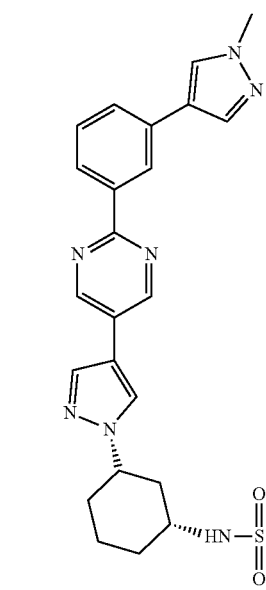

29 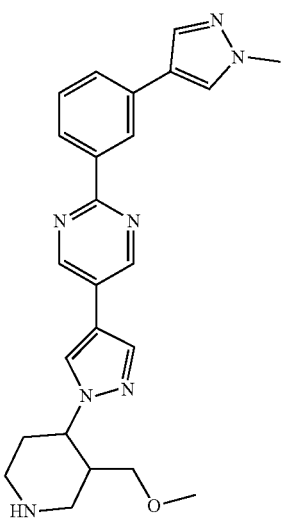

46 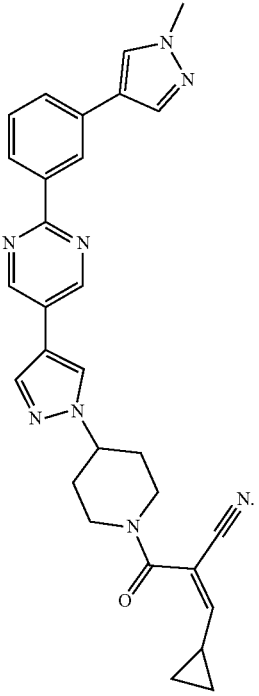

or a pharmaceutically acceptable salt, tautomer or stereoisomer thereof.

6. A pharmaceutical formulation comprising a pharmaceutically acceptable excipient or adjuvant and at least one compound of claim 1, or a pharmaceutically acceptable salt, tautomer or stereoisomer thereof.

7. The pharmaceutical formulation of claim 6, wherein the pharmaceutical formulation comprises at least one further medicament.

8. A kit consisting of separate packs of:
(a) an effective amount of a compound of claim 1, or a pharmaceutically acceptable salt, tautomer or stereoisomer thereof; and
(b) an effective amount of a further active medicament.

9. A method for inhibiting interleukin-1 receptor-associated kinase activity in a subject having a disease selected from the group consisting of an inflammatory disease, an autoimmune disorder, multiple sclerosis and cancer, comprising administering to the subject a compound of claim 1, or a pharmaceutically acceptable salt, tautomer or stereoisomer thereof.

10. The method of claim 9, wherein the subject has an inflammatory disease or an autoimmune disorder selected from the group consisting of rheumatoid arthritis, lupus nephritis and systemic lupus erythematosus.

11. The method of claim 9, wherein the autoimmune disorder is selected from the group consisting of acute disseminated encephalomyelitis, Addison's disease, alopecia areata, ankylosing spondylitis, antiphospholipid antibody syndrome, asthma, autoimmune hemolytic anemia, autoimmune hepatitis, autoimmune inner ear disease, bullous pemphigoid, Behcet's disease, Coeliac disease, antitransglutaminase, Chagas disease, chronic obstructive pulmonary disease, Crohn's disease, dermatomyositis, diabetes mellitus type 1, endometriosis, Goodpasture's syndrome, Graves' disease, Guillain-Barré syndrome, Hashimoto's disease, hidradenitis suppurativa, Kawasaki disease, immuno-

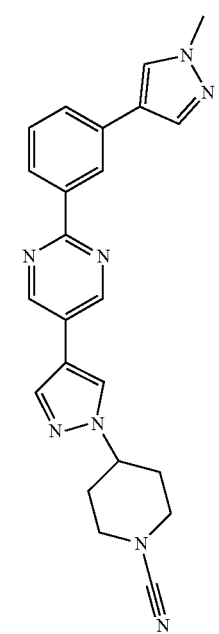 and globin A nephropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, rheumatoid arthritis, schizophrenia, scleroderma, Sjogren's syndrome, stiff person syndrome, systemic sclerosis, temporal arteritis, ulcerative colitis, vasculitis, vitiligo and Wegener's granulomatosis.

* * * * *